(12) United States Patent
Hada et al.

(10) Patent No.: US 9,034,556 B2
(45) Date of Patent: May 19, 2015

(54) COMPOUND AND METHOD OF PRODUCING THE SAME, ACID GENERATOR, RESIST COMPOSITION AND METHOD OF FORMING RESIST PATTERN

(75) Inventors: Hideo Hada, Kawasaki (JP); Yoshiyuki Utsumi, Kawasaki (JP); Keita Ishiduka, Kawasaki (JP); Kensuke Matsuzawa, Kawasaki (JP); Fumitake Kaneko, Kawasaki (JP); Kyoko Ohshita, Kawasaki (JP); Hiroaki Shimizu, Kawasaki (JP); Yasuhiro Yoshii, Kawasaki (JP)

(73) Assignee: Tokyo Ohka Kogyo Co., Ltd., Kawasaki-shi (JP)

( * ) Notice: Subject to any disclaimer, the term of this patent is extended or adjusted under 35 U.S.C. 154(b) by 1148 days.

(21) Appl. No.: 12/338,661

(22) Filed: Dec. 18, 2008

(65) Prior Publication Data
US 2009/0162788 A1 Jun. 25, 2009

(30) Foreign Application Priority Data

Dec. 21, 2007 (JP) ................................ 2007-330891
Dec. 21, 2007 (JP) ................................ 2007-331163
Mar. 6, 2008 (JP) ................................ 2008-056880

(51) Int. Cl.
| | |
|---|---|
| *G03F 7/004* | (2006.01) |
| *G03F 7/30* | (2006.01) |
| *C07C 303/32* | (2006.01) |
| *C07C 309/06* | (2006.01) |
| *C07C 309/12* | (2006.01) |
| *C07C 309/19* | (2006.01) |
| *C07C 381/12* | (2006.01) |
| *C07C 309/17* | (2006.01) |
| *C07D 333/46* | (2006.01) |
| *C07D 493/18* | (2006.01) |
| *G03F 7/038* | (2006.01) |
| *G03F 7/039* | (2006.01) |
| *C08K 5/19* | (2006.01) |
| *C08K 5/42* | (2006.01) |

(52) U.S. Cl.
CPC .............. *C07C 381/12* (2013.01); *C07C 309/19* (2013.01); *C07C 309/12* (2013.01); *C07C 309/06* (2013.01); *C07C 303/32* (2013.01); *C07C 309/17* (2013.01); *C07C 2103/74* (2013.01); *C07D 333/46* (2013.01); *C07D 493/18* (2013.01); *C08K 5/19* (2013.01); *C08K 5/42* (2013.01); *G03F 7/0045* (2013.01); *G03F 7/0046* (2013.01); *G03F 7/0382* (2013.01); *G03F 7/0397* (2013.01); *Y10S 430/111* (2013.01); *Y10S 430/12* (2013.01); *Y10S 430/122* (2013.01); *Y10S 430/123* (2013.01)

(58) Field of Classification Search
CPC ....... G03F 7/0045; G03F 7/0397; G03F 7/30; C07C 309/12; C07C 309/06; C07C 309/19; C07C 381/12; C07C 303/32

USPC .............. 430/270.1, 905, 910, 921, 922, 326, 430/919; 562/42, 100, 109, 113, 112
See application file for complete search history.

(56) References Cited

U.S. PATENT DOCUMENTS

| | | | |
|---|---|---|---|
| 5,945,517 A | 8/1999 | Nitta et al. | |
| 6,153,733 A | 11/2000 | Yukawa et al. | |
| 6,893,792 B2 * | 5/2005 | Miya et al. | .................. 430/270.1 |
| 7,301,047 B2 * | 11/2007 | Yoshida et al. | ............... 560/129 |
| 7,304,175 B2 * | 12/2007 | Harada et al. | .................. 560/129 |
| 7,323,287 B2 | 1/2008 | Iwai et al. | |

(Continued)

FOREIGN PATENT DOCUMENTS

| | | |
|---|---|---|
| CN | 1991585 A | 7/2007 |
| CN | 101003591 A | 7/2007 |

(Continued)

OTHER PUBLICATIONS

Office Action issued in corresponding Korean Patent Application No. 10-2010-0135554, dated Mar. 17, 2011.

(Continued)

*Primary Examiner* — John Chu
(74) *Attorney, Agent, or Firm* — Knobbe Martens Olson & Bear LLP

(57) ABSTRACT

A resist composition including a base component (A) which exhibits changed solubility in an alkali developing solution under action of acid and an acid-generator component (B) which generates acid upon exposure, the acid-generator component (B) including an acid generator (B1) consisting of a compound represented by general formula (b1-1) shown below:

[Chemical Formula 1]

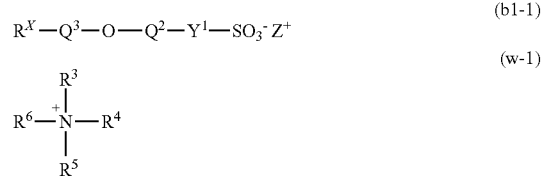

wherein $R^X$ represents a hydrocarbon group which may have a substituent exclusive of a nitrogen atom; each of $Q^2$ and $Q^3$ independently represents a single bond or a divalent linkage group; $Y^1$ represents an alkylene group or fluorinated alkyl group of 1 to 4 carbon atoms; and $Z^+$ represents an organic cation exclusive of an ion represented by general formula (w-1).

11 Claims, No Drawings

(56) References Cited

U.S. PATENT DOCUMENTS

| | | | |
|---|---|---|---|
| 7,531,686 B2* | 5/2009 | Harada et al. | 560/117 |
| 7,670,751 B2 | 3/2010 | Ohashi et al. | |
| 7,786,322 B2* | 8/2010 | Yamaguchi et al. | 560/150 |
| 7,812,105 B2 | 10/2010 | Nagai et al. | |
| 7,932,334 B2* | 4/2011 | Ando et al. | 526/243 |
| 2004/0002007 A1 | 1/2004 | Hitoshi et al. | |
| 2004/0053158 A1* | 3/2004 | Yamato et al. | 430/270.1 |
| 2005/0208420 A1 | 9/2005 | Ober et al. | |
| 2006/0194982 A1 | 8/2006 | Harada et al. | |
| 2007/0027336 A1 | 2/2007 | Yoshida et al. | |
| 2007/0078269 A1 | 4/2007 | Harada et al. | |
| 2007/0100096 A1 | 5/2007 | Harada et al. | |
| 2007/0100158 A1* | 5/2007 | Harada et al. | 560/149 |
| 2007/0100159 A1* | 5/2007 | Yoshida et al. | 560/149 |
| 2007/0122750 A1* | 5/2007 | Yamaguchi et al. | 430/311 |
| 2007/0149702 A1 | 6/2007 | Ando et al. | |
| 2007/0184382 A1 | 8/2007 | Yamaguchi et al. | |
| 2007/0264596 A1 | 11/2007 | Ohsawa et al. | |
| 2008/0032231 A1 | 2/2008 | Hatakeyama et al. | |
| 2008/0086014 A1 | 4/2008 | Shigematsu et al. | |
| 2008/0199806 A1 | 8/2008 | Hatakeyama et al. | |
| 2009/0061358 A1 | 3/2009 | Ohashi et al. | |
| 2011/0034721 A1 | 2/2011 | Hagiwara et al. | |

FOREIGN PATENT DOCUMENTS

| | | |
|---|---|---|
| EP | 1 780 199 A1 | 5/2007 |
| EP | 1897869 | 3/2008 |
| EP | 1 873 143 B1 | 4/2009 |
| EP | 2 073 060 | 6/2009 |
| GB | 2446273 A | 8/2008 |
| GB | 2446687 A | 8/2008 |
| GB | 2447789 A | 9/2008 |
| JP | A-06-247924 | 9/1994 |
| JP | H09-208554 | 8/1997 |
| JP | H11-035551 | 2/1999 |
| JP | H11-035552 | 2/1999 |
| JP | H11-035573 | 2/1999 |
| JP | H11-322707 | 11/1999 |
| JP | A-2001-133984 | 5/2001 |
| JP | A-2003-057825 | 2/2003 |
| JP | 2003-241385 | 8/2003 |
| JP | A-2004-075864 | 3/2004 |
| JP | A-2004-510189 | 4/2004 |
| JP | A-2006-257078 | 9/2006 |
| JP | A-2006-306856 | 11/2006 |
| JP | A-2007-145822 | 6/2007 |
| JP | A-2007-197432 | 8/2007 |
| JP | A-2007-197718 | 8/2007 |
| JP | A-2008-039815 | 2/2008 |
| JP | A-2008-074843 | 4/2008 |
| JP | A-2008-094835 | 4/2008 |
| JP | A-2008-096684 | 4/2008 |
| JP | 2009-007327 | 1/2009 |
| JP | A-2009-063989 | 3/2009 |
| JP | A-2009-091351 | 4/2009 |
| JP | A-2009-149586 | 7/2009 |
| KR | 10-2007-0053619 | 5/2007 |
| WO | WO 02/25376 A2 | 3/2002 |
| WO | WO 2004/074242 A2 | 9/2004 |
| WO | WO 2006/121096 A1 | 11/2006 |
| WO | WO 2008/099869 A1 | 8/2008 |

OTHER PUBLICATIONS

Office Action issued in corresponding European Patent Application No. 08172244.9, dated Dec. 17, 2010.
Decision for Grant of Patent issued in corresponding Korean Application No. 10-2008-0129260 dated May 27, 2011.
The European Search Report issued on the corresponding European Patent Application No. 08172244.9, dated May 8, 2009.
Office Action issued in corresponding Chinese Patent Application No. 200810185226.8, dated Apr. 13, 2011.
Office Action issued in Chinese Application No. 200810185226.8 on Nov. 30, 2011.
Notice of Allowance issued in Korean Application No. 10-2010-0135554 on Nov. 30, 2011.
Office Action issued on Oct. 17, 2013 in U.S. Appl. No. 13/410,613.
Investa Akademii nauk, SSSR. Seria himiceskaa, vol. 6, pp. 1289-1294, 1967.
Office Action issued on Dec. 18, 2012 for Japanese Patent Application No. 2007-331163.
Notice of Allowance issued on Dec. 21, 2012 for Japanese Patent Application No. 2008-056880.
Office Action issued in U.S. Appl. No. 13/410,613 on Feb. 20, 2014.
Office Action in corresponding Japanese Patent Application No. 2008-056880, mailed Apr. 24, 2012.

* cited by examiner

COMPOUND AND METHOD OF PRODUCING THE SAME, ACID GENERATOR, RESIST COMPOSITION AND METHOD OF FORMING RESIST PATTERN

TECHNICAL FIELD

The present invention relates to a novel compound useful as an acid generator for a resist composition, and the method of producing the same; an acid generator; a resist composition and a method of forming a resist pattern; and a novel compound useful as an intermediate of the compound useful as an acid generator for a resist composition, and the method of producing the same.

Priority is claimed on Japanese Patent Application No. 2007-330891, filed Dec. 21, 2007, Japanese Patent Application No. 2007-331163, filed Dec. 21, 2007 and Japanese Patent Application No. 2008-056880, filed Mar. 6, 2008, the contents of which are incorporated herein by reference.

BACKGROUND ART

In lithography techniques, for example, a resist film composed of a resist material is formed on a substrate, and the resist film is subjected to selective exposure of radial rays such as light or electron beam, followed by development, thereby forming a resist pattern having a predetermined shape on the resist film. A resist material in which the exposed portions become soluble in a developing solution is called a positive-type, and a resist material in which the exposed portions become insoluble in a developing solution is called a negative-type.

In recent years, in the production of semiconductor elements and liquid crystal display elements, advances in lithography techniques have lead to rapid progress in the field of pattern miniaturization.

Typically, these miniaturization techniques involve shortening the wavelength of the exposure light source. Conventionally, ultraviolet radiation typified by g-line and i-line radiation has been used, but nowadays KrF excimer lasers and ArF excimer lasers are now starting to be introduced in mass production. Furthermore, research is also being conducted into lithography techniques that use exposure light source having a wavelength shorter than these excimer lasers, such as $F_2$ excimer lasers, electron beam, extreme ultraviolet radiation (EUV), and X ray.

As the wavelength of the exposure source have been shortened, resist materials for use with these types of exposure light sources required improvement in lithography properties such as a high resolution capable of reproducing patterns of minute dimensions, and a high level of sensitivity to these types of exposure light sources. As a resist material which satisfies these conditions, a chemically amplified resist is used, which includes a base component that exhibits a changed solubility in an alkali developing solution under action of acid and an acid generator that generates acid upon exposure.

Conventionally, as the base component for these chemically amplified resists, resins have been mainly used. For example, polyhydroxystyrene (PHS) or derivative resins thereof in which the hydroxyl groups are protected with acid dissociable, dissolution inhibiting groups (PHS-based resins), a copolymer derived from (meth)acrylate ester and a resin in which a part of the carboxy groups within such a copolymer are protected with acid dissociable, dissolution inhibiting groups, and the like have been used.

Here, the term "(meth)acrylate ester" is a generic term that includes either or both of the acrylate ester having a hydrogen atom bonded to the α-position and the methacrylate ester having a methyl group bonded to the α-position. The term "(meth)acrylate" is a generic term that includes either or both of the acrylate having a hydrogen atom bonded to the α-position and the methacrylate having a methyl group bonded to the α-position. The term "(meth)acrylic acid" is a generic term that includes either or both of acrylic acid having a hydrogen atom bonded to the α-position and methacrylic acid having a methyl group bonded to the α-position.

As acid generators usable in a chemically amplified resist, various types have been proposed including, for example, onium salt-based acid generators such as iodonium salts and sulfonium salts (see for example, Patent Document 1).

[Patent Document 1] Japanese Unexamined Patent Application, First Publication No. 2003-241385

DISCLOSURE OF INVENTION

Problems to be Solved by the Invention

Currently, as the anion moiety for the aforementioned onium salt-based acid generators, a perfluoroalkylsulfonic acid ion is generally used.

However, due to its structures such an onium salt-based acid generator exhibits low affinity for an alkali developing solution. Further, such an onium salt-based acid generator is hard to be uniformly diffused within the resist film. As a result, lithography properties such as resolution and the like are likely to be harmfully affected.

Further, it is considered that the perfluoroalkyl chain within the anion moiety is preferably long, as diffusion of acid after exposure can be suppressed. However, a perfluoroalkyl chain of 6 to 10 carbon atoms is hardly decomposable, and hence, for minimizing bioaccumulation to improve safety in handling, a perfluoroalkylsulfonic acid ion of no more than 4 carbon atoms such as a nonafluorobutanesulfonic acid ion or the like has been used.

Therefore, development of an onium salt-based compound having an anion moiety which is more suitable as an acid generator for a resist composition has been demanded, and an intermediate useful in the production of such a compound has also been demanded.

The present invention takes the above circumstances into consideration, with an object of providing a novel compound useful as an acid generator for a resist composition, and the method of producing the same; an acid generator; a resist composition and a method of forming a resist pattern; and a novel compound useful as an intermediate of the compound useful as an acid generator for a resist composition, and the method of producing the same.

Means to Solve the Problems

For solving the above-mentioned problems, the present invention employs the following aspects.

Specifically, a first aspect of the present invention is a resist composition including a base component (A) which exhibits changed solubility in an alkali developing solution under action of acid and an acid-generator component (B) which generates acid upon exposure, the acid-generator component (B) including an acid generator (B1) consisting of a compound represented by general formula (b1-1) shown below.

[Chemical Formula 1]

$$R^X\text{-}Q^3\text{-}O\text{-}Q^2\text{-}Y^1\text{—}SO_3^-Z^+ \quad \quad (b1\text{-}1)$$

wherein $R^X$ represents a hydrocarbon group which may have a substituent exclusive of a nitrogen atom; each of $Q^2$ and $Q^3$ independently represents a single bond or a divalent linkage group; $Y^1$ represents an alkylene group or fluorinated alkyl group of 1 to 4 carbon atoms; and $Z^+$ represents an organic cation exclusive of an ion represented by general formula (w-1) shown below.

[Chemical Formula 2]

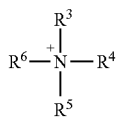
(w-1)

wherein each of $R^3$ to $R^6$ independently represents a hydrogen atom or a hydrocarbon group which may have a substituent, with the proviso that at least one of $R^3$ to $R^6$ represents a hydrocarbon group; and at least two of $R^3$ to $R^6$ may be mutually bonded to form a ring.

A second aspect of the present invention is a method of forming a resist pattern, including: applying a resist composition of the first aspect to a substrate to form a resist film on the substrate; conducting exposure of the resist film; and alkali-developing the resist film to form a resist pattern.

A third aspect of the present invention is compound represented by general formula (b1-1) shown below (hereafter, referred to as "compound (b1-1)").

[Chemical Formula 3]

$$R^X\text{-}Q^3\text{-}O\text{-}Q^2\text{-}Y^1\text{—}SO_3^-Z^+ \quad (b1\text{-}1)$$

wherein $R^X$ represents a hydrocarbon group which may have a substituent exclusive of a nitrogen atom; each of $Q^2$ and $Q^3$ independently represents a single bond or a divalent linkage group; $Y^1$ represents an alkylene group or fluorinated alkyl group of 1 to 4 carbon atoms; and $Z^+$ represents an organic cation exclusive of an ion represented by general formula (w-1) shown below.

[Chemical Formula 4]

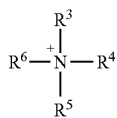
(w-1)

wherein each of $R^3$ to $R^6$ independently represents a hydrogen atom or a hydrocarbon group which may have a substituent, with the proviso that at least one of $R^3$ to $R^6$ represents a hydrocarbon group; and at least two of $R^3$ to $R^6$ may be mutually bonded to form a ring.

A fourth aspect of the present invention is a method of producing a compound (b1-1) represented by general formula (b1-1) shown below, including reacting a compound (b0-1) represented by general formula (b0-1) shown below with a compound (b0-02) represented by general formula (b0-02) shown below (hereafter, this method is referred to as "production method of compound (b1-1)").

[Chemical Formula 5]

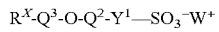
(b0-1)

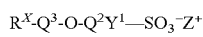
(b1-1)

wherein $R^X$ represents a hydrocarbon group which may have a substituent exclusive of a nitrogen atom; each of $Q^2$ and $Q^3$ independently represents a single bond or a divalent linkage group; $Y^1$ represents alkylene group or fluorinated alkyl group of 1 to 4 carbon atoms; $W^+$ represents an alkali metal ion or an ion represented by general formula (w-1) shown below; $Z^+$ represents an organic cation exclusive of an ion represented by general formula (w-1) shown below; and $A^-$ represents a non-nucleophilic ion.

[Chemical Formula 6]

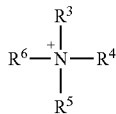
(w-1)

wherein each of $R^3$ to $R^6$ independently represents a hydrogen atom or a hydrocarbon group which may have a substituent, with the proviso that at least one of $R^3$ to $R^6$ represents a hydrocarbon group; and at least two of $R^3$ to $R^6$ may be mutually bonded to form a ring.

A fifth aspect of the present invention is an acid generator consisting of a compound of the third aspect.

A sixth aspect of the present invention is a compound represented by general formula (b0-1) shown below (hereafter, referred to as "compound (b0-1)").

[Chemical Formula 7]

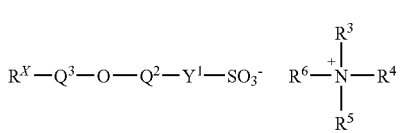
(b0-1)

wherein $R^X$ represents a hydrocarbon group which may have a substituent exclusive of a nitrogen atom; each of $Q^2$ and $Q^3$ independently represents a single bond or a divalent linkage group; $Y^1$ represents an alkylene group or fluorinated alkyl group of 1 to 4 carbon atoms; each of $R^3$ to $R^6$ independently represents a hydrogen atom or a hydrocarbon group which may have a substituent, with the proviso that at least one of $R^3$ to $R^6$ represents a hydrocarbon group; and at least two of $R^3$ to $R^6$ may be mutually bonded to form a ring.

A seventh aspect of the present invention is a method of producing a compound (b0-1) represented by general formula (b0-1) shown below, including reacting a compound (1-11) represented by general formula (1-11) shown below and a compound (1-12) represented by general formula (1-12) shown below with an amine or an ammonium salt (hereafter, this method is referred to as "production method (1) compound (b0-1)").

[Chemical Formula 8]

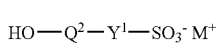
(1-11)

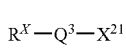
(1-12)

-continued

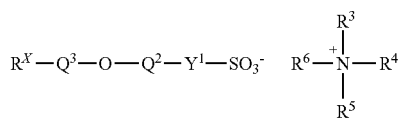
(b0-1)

wherein $R^X$ represents a hydrocarbon group which may have a substituent exclusive of a nitrogen atom; each of $Q^2$ and $Q^3$ independently represents a single bond or a divalent linkage group; $Y^1$ represents an alkylene group or fluorinated alkyl group of 1 to 4 carbon atoms; each of $R^3$ to $R^6$ independently represents a hydrogen atom or a hydrocarbon group which may have a substituent, with the proviso that at least one of $R^3$ to $R^6$ represents a hydrocarbon group; and at least two of $R^3$ to $R^6$ may be mutually bonded to form a ring; $X^{21}$ represents a halogen atom; and $M^+$ represents an alkali metal ion.

An eighth aspect of the present invention is a method of producing a compound (b0-1) represented by general formula (b0-1) shown below, including reacting a compound (1-21) represented by general formula (1-21) shown below and a compound (1-12) represented by general formula (1-12) shown below with an amine or an ammonium salt (hereafter, this method is referred to as "production method (2) of compound (b0-1)").

[Chemical Formula 9]

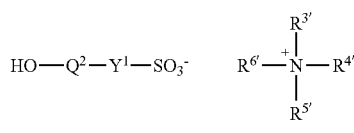
(1-21)

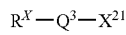
(1-12)

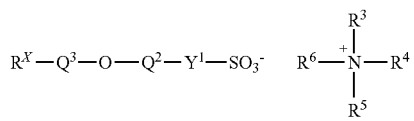
(b0-1)

wherein $R^X$ represents a hydrocarbon group which may have a substituent exclusive of a nitrogen atom; each of $Q^2$ and $Q^3$ independently represents a single bond or a divalent linkage group; $Y^1$ represents an alkylene group or fluorinated alkyl group of 1 to 4 carbon atoms; each of $R^3$ to $R^6$ independently represents a hydrogen atom or a hydrocarbon group which may have a substituent, with the proviso that at least one of $R^3$ to $R^6$ represents a hydrocarbon group; and at least two of $R^3$ to $R^6$ may be mutually bonded to form a ring; each of $R^{3\prime}$ to $R^{6\prime}$ independently represents a hydrogen atom or a hydrocarbon group which may have a substituent, with the proviso that at least one of $R^{3\prime}$ to $R^{6\prime}$ represents a hydrocarbon group, and at least two of $R^{3\prime}$ to $R^{6\prime}$ may be mutually bonded to form a ring; and $X^{21}$ represents a halogen atom.

A ninth aspect of the present invention is a compound (1-21) represented by general formula (1-21) shown below.

[Chemical Formula 10]

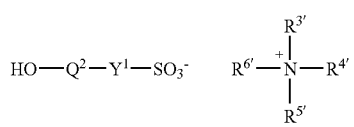
(1-21)

wherein $Q^2$ represents a single bond or a divalent linkage group; $Y^1$ represents an alkylene group or fluorinated alkyl group of 1 to 4 carbon atoms; each of $R^{3\prime}$ to $R^{6\prime}$ independently represents a hydrogen atom or a hydrocarbon group which may have a substituent, with the proviso that at least one of $R^{3\prime}$ to $R^{6\prime}$ represents a hydrocarbon group; and at least two of $R^{3\prime}$ to $R^{6\prime}$ may be mutually bonded to form a ring.

A tenth aspect of the present invention is a method of producing a compound (1-21) represented by general formula (1-21) shown below, including reacting a compound (1-11) represented by general formula (1-11) shown below with an ammonium salt (hereafter, this method is referred to as "production method of compound (1-21)").

[Chemical Formula 11]

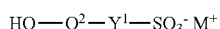
(1-11)

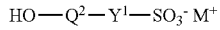
(1-21)

wherein $Q^2$ represents a single bond or a divalent linkage group; $Y^1$ represents an alkylene group or fluorinated alkyl group of 1 to 4 carbon atoms; each of $R^{3\prime}$ to $R^{6\prime}$ independently represents a hydrogen atom or a hydrocarbon group which may have a substituent, with the proviso that at least one of $R^{3\prime}$ to $R^{6\prime}$ represents a hydrocarbon group; and at least two of $R^{3\prime}$ to $R^{6\prime}$ may be mutually bonded to form a ring; and $M^+$ represents an alkali metal ion.

An eleventh aspect of the present invention is a method of producing a compound (1-14) represented by general formula (1-14) shown below, including reacting a compound (1-13) represented by general formula (1-13) shown below with an ammonium salt (hereafter, this method is referred to as "production method of compound (1-14)").

[Chemical Formula 12]

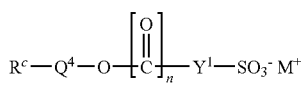
(1-13)

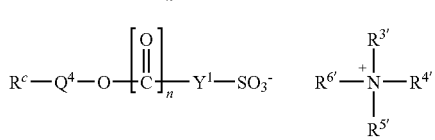
(1-14)

wherein $R^c$ represents a hydrocarbon group which may have a substituent exclusive of a nitrogen atom; $Q^4$ represents a single bond or a divalent linkage group; n represents 0 or 1; $Y^1$ represents an alkylene group or fluorinated alkyl group of 1 to 4 carbon atoms; each of $R^{3\prime}$ to $R^{6\prime}$ independently represents a hydrogen atom or a hydrocarbon group which may have a substituent, with the proviso that at least one of $R^{3\prime}$ to $R^{6\prime}$ represents a hydrocarbon group; and at least two of $R^{3\prime}$ to $R^{6\prime}$ may be mutually bonded to form a ring; and $M^+$ represents an alkali metal ion.

In the present description and claims, the term "aliphatic" is a relative concept used in relation to the term "aromatic", and defines a group or compound that has no aromaticity.

The term "alkylene group" includes linear, branched or cyclic divalent saturated hydrocarbon, unless otherwise specified.

The term "alkyl group" includes linear, branched or cyclic, monovalent saturated hydrocarbon, unless otherwise specified. A "lower alkyl group" is an alkyl group of 1 to 5 carbon atoms.

The term "structural unit" refers to a monomer unit that contributes to the formation of a resin component (polymer).

The term "exposure" is used as a general concept that includes irradiation with any form of radiation.

Effect of the Invention

According to the present invention, there are provided a novel compound useful as an acid generator for a resist composition, and the method of producing the same; an acid generator; a resist composition and a method of forming a resist pattern; and a novel compound useful as an intermediate of the compound useful as an acid generator for a resist composition, and the method of producing the same.

BEST MODE FOR CARRYING OUT THE INVENTION

First, the compound (b0-1) according to the sixth aspect of the present invention will be described.

The compound (b0-1) according to the sixth aspect of the present invention is a compound represented by general formula (b0-1) above.

In general formula (b0-1), the hydrocarbon group for $R^X$ may be either an aromatic hydrocarbon group or an aliphatic hydrocarbon group.

The aromatic hydrocarbon group for $R^X$ is a hydrocarbon group having an aromatic ring, and preferably has 3 to 30 carbon atoms, more preferably 5 to 30, still more preferably 5 to 20, still more preferably 6 to 15, and most preferably 6 to 12. Here, the number of carbon atoms within a substituent(s) is not included in the number of carbon atoms of the aromatic hydrocarbon group.

Specific examples of aromatic hydrocarbon groups include an aryl group which is an aromatic hydrocarbon ring having one hydrogen atom removed therefrom, such as a phenyl group, a biphenyl group, a fluorenyl group, a naphthyl group, an anthryl group or a phenanthryl group; a benzyl group; a phenethyl group; and an alkylaryl group such as a 1-naphthylmethyl group, a 2-naphthylmethyl group, a 1-naphthylethyl group, or a 2-naphthylethyl group. The alkyl chain within the arylalkyl group preferably has 1 to 4 carbon atom, more preferably 1 or 2, and most preferably 1.

The aromatic hydrocarbon group may have a substituent. For example, a part of the carbon atoms constituting the aromatic ring within the aromatic hydrocarbon group may be substituted with a hetero atom, or a hydrogen atom bonded to the aromatic ring within the aromatic hydrocarbon group may be substituted with a substituent.

In the former example, a heteroaryl group in which a part of the carbon atoms constituting the ring within the aforementioned aryl group has been substituted with a hetero atom (exclusive of a nitrogen atom) such as an oxygen atom or a sulfur atom, and a heteroarylalkyl group in which a part of the carbon atoms constituting the aromatic hydrocarbon ring within the aforementioned arylalkyl group has been substituted with the aforementioned heteroatom can be mentioned.

In the latter example, as the substituent for the aromatic hydrocarbon group, an alkyl group, an alkoxy group, a halogen atom, a halogenated alkyl group, a hydroxyl group, an oxygen atom (=O) or the like can be mentioned.

The alkyl group as the substituent for the aromatic hydrocarbon group is preferably an alkyl group of 1 to 5 carbon atoms, and a methyl group, an ethyl group, a propyl group, an n-butyl group or a tert-butyl group is particularly desirable.

The alkoxy group as the substituent for the aromatic hydrocarbon group is preferably an alkoxy group having 1 to 5 carbon atoms, more preferably a methoxy group, ethoxy group, n-propoxy group, iso-propoxy group, n-butoxy group or tert-butoxy group, and most preferably a methoxy group or an ethoxy group.

Examples of the halogen atom as the substituent for the aromatic hydrocarbon group include a fluorine atom, a chlorine atom, a bromine atom and an iodine atom, and a fluorine atom is preferable.

Example of the halogenated alkyl group as the substituent for the aromatic hydrocarbon group includes a group in which a part or all of the hydrogen atoms within the aforementioned alkyl group have been substituted with the aforementioned halogen atoms.

The aliphatic hydrocarbon group for $R^X$ may be either a saturated aliphatic hydrocarbon group, or an unsaturated aliphatic hydrocarbon group. Further, the aliphatic hydrocarbon group may be linear, branched or cyclic.

In the aliphatic hydrocarbon group for $R^X$, a part of the carbon atoms constituting the aliphatic hydrocarbon group may be substituted with a substituent group containing a hetero atom (exclusive of a nitrogen atom), or a part or all of the hydrogen atoms constituting the aliphatic hydrocarbon group may be substituted with a substituent group containing a hetero atom (exclusive of a nitrogen atom).

As the "hetero atom" for $R^X$, there is no particular limitation as long as it is an atom other than a carbon atom, a hydrogen atom and a nitrogen atom. Examples of hetero atoms include a halogen atoms an oxygen atom and a sulfur atom.

Examples of halogen atoms include a fluorine atom, a chlorine atom, an iodine atom and a bromine atom.

The substituent group containing a hetero atom (exclusive of a nitrogen atom) may consist of a hetero atom, or may be a group containing a group or atom other than a hetero atom.

Specific examples of the substituent group for substituting a part of the carbon atoms include —O—, —C(=O)—O—, —C(=O)—, —O—C(=O)—O—, —S—, —S(=O)$_2$— and —S(=O)$_2$—O—. When the aliphatic hydrocarbon group is cyclic, the aliphatic hydrocarbon group may contain these substituent groups in the ring structure.

Examples of the substituent group for substituting a part or all of the hydrogen atoms include an alkoxy group, a halogen atom, a halogenated alkyl group, a hydroxyl group and an oxygen atom (=O).

The aforementioned alkoxy group is preferably an alkoxy group having 1 to 5 carbon atoms, more preferably a methoxy group, ethoxy group, n-propoxy group, iso-propoxy group, n-butoxy group or tert-butoxy group, and most preferably a methoxy group or an ethoxy group.

Examples of the aforementioned halogen atom include a fluorine atom, a chlorine atom, a bromine atom and an iodine atom, and a fluorine atom is preferable.

Example of the aforementioned halogenated alkyl group includes a group in which a part or all of the hydrogen atoms within an alkyl group of 1 to 5 carbon atoms (e.g., a methyl group, an ethyl group, a propyl group, an n-butyl group or a tert-butyl group) have been substituted with the aforementioned halogen atoms.

As the aliphatic hydrocarbon group, a linear or branched saturated hydrocarbon group, a linear or branched monovalent unsaturated hydrocarbon group, or a cyclic aliphatic hydrocarbon group is preferable.

The linear saturated hydrocarbon group (alkyl group) preferably has 1 to 20 carbon atoms, more preferably 1 to 15, and most preferably 1 to 10. Specific examples include a methyl group, an ethyl group, a propyl group, a butyl group, a pentyl group, a hexyl group, a heptyl group, an octyl group, a nonyl group, a decanyl group, an undecyl group, a dodecyl group, a tridecyl group, an isotridecyl group, a tetradecyl group, a pentadecyl group, a hexadecyl group, an isohexadecyl group, a heptadecyl group, an octadecyl group, a nonadecyl group, an icosyl group, a henicosyl group and a docosyl group.

The branched saturated hydrocarbon group (alkyl group) preferably has 3 to 20 carbon atoms, more preferably 3 to 15, and most preferably 3 to 10. Specific examples include a 1-methylethyl group, a 1-methylpropyl group, a 2-methylpropyl group, a 1-methylbutyl group, a 2-methylbutyl group, a 3-methylbutyl group, a 1-ethylbutyl group, a 2-ethylbutyl group, a 1-methylpentyl group, a 2-methylpentyl group, a 3-methylpentyl group and a 4-mnethylpentyl group.

The unsaturated hydrocarbon group preferably has 2 to 10 carbon atoms, more preferably 2 to 5, still more preferably 2 to 4, and most preferably 3. Examples of linear monovalent unsaturated hydrocarbon groups include a vinyl group, a propenyl group (an allyl group) and a butynyl group. Examples of branched monovalent unsaturated hydrocarbon groups include a 1-methylpropenyl group and a 2-methylpropenyl group.

Among the above-mentioned examples, as the unsaturated hydrocarbon group, a propenyl group is particularly desirable.

The aliphatic cyclic group may be either a monocyclic group or a polycyclic group. The aliphatic cyclic group preferably has 3 to 30 carbon atoms, more preferably 5 to 30, still more preferably 5 to 20, still more preferably 6 to 15, and most preferably 6 to 12.

As the aliphatic cyclic group, a group in which one or more hydrogen atoms have been removed from a monocycloalkane or a polycycloalkane such as a bicyloalkane, tricycloalkane or tetracycloalkane can be mentioned. Specific examples include groups in which one or more hydrogen atoms have been removed from a monocycloalkane such as cyclopentane or cyclohexane; and groups in which one or more hydrogen atoms have been removed from a polycycloalkane such as adamantane, norbornane, isobornane, tricyclodecane or tetracyclododecane.

When the aliphatic cyclic group does not contain a hetero atom-containing substituent group in the ring structure thereof, the aliphatic cyclic group is preferably a polycyclic group, more preferably a group in which one or more hydrogen atoms have been removed from a polycycloalkane, and a group in which one or more hydrogen atoms have been removed from adamantane is particularly desirable.

When the aliphatic cyclic group contains a hetero atom-containing substituent group in the ring structure thereof, the hetero atom-containing substituent group is preferably —O—, —C(=O)—O—, —S—, —S(=O)$_2$— or —S(=O)$_2$—O—. Specific examples of such aliphatic cyclic groups include groups represented by formulas (L1) to (L5) and (S1) to (S4) shown below.

[Chemical Formula 13]

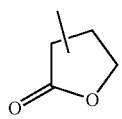
(L1)

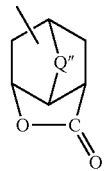
(L2)

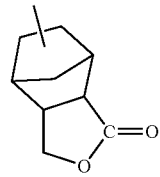
(L3)

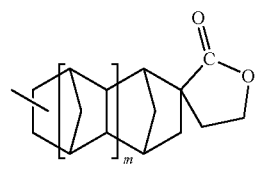
(L4)

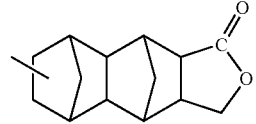
(L5)

(S1)

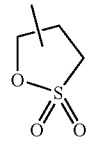
(S2)

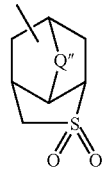
(S3)

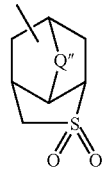
(S4)

wherein Q″ represents an alkylene group of 1 to 5 carbon atoms, —O—, —S—, —O—R$^{94}$— or —S—R$^{95}$— (wherein each of R$^{94}$ and R$^{95}$ independently represents an alkylene group of 1 to 5 carbon atoms); and m represents 0 or 1.

As the alkylene group for Q″, the same alkylene groups as those for R$^1$ above can be mentioned.

As the alkylene group for R$^{94}$ and R$^{95}$, the same alkylene groups as those for R$^1$ above can be mentioned.

In these aliphatic cyclic groups, a part of the hydrogen atoms boned to the carbon atoms constituting the ting structure may be substituted with a substituent. Examples of substituents include an alkyl group, an alkoxy group, a halogen atom, a halogenated alkyl group, a hydroxyl group and an oxygen atom (=O).

As the alkyl group, an alkyl group of 1 to 5 carbon atoms is preferable, and a methyl group, an ethyl group, a propyl group, an n-butyl group or a tert-butyl group is particularly desirable.

As the alkoxy group and the halogen atom, the same groups as the substituent groups for substituting a part or all of the hydrogen atoms can be mentioned.

In the present invention, as $R^X$, a linear alkyl group which may have a substituent, or a cyclic group which may have a substituent is preferable. The cyclic group may be either an aromatic hydrocarbon group which may have a substituent, or an aliphatic cyclic group which may have a substituent, and an aliphatic cyclic group which may have a substituent is preferable.

As the aromatic hydrocarbon group, a naphthyl group which may have a substituent, or a phenyl group which may have a substituent is preferable.

As the aliphatic cyclic group which may have a substituent, an aliphatic polycyclic group which may have a substituent is preferable. As the aliphatic polycyclic group, the aforementioned group in which one or more hydrogen atoms have been removed from a polycycloalkane, and groups represented by formulas (L1) to (L5) and (S1) to (S4) are preferable, and an adamantyl group is particularly desirable.

Each of $Q^2$ and $Q^3$ independently represents a single bond or a divalent linkage group.

Examples of divalent linkage groups include an alkylene group and a group containing a hetero atom (hereafter, referred to as a "hetero atom-containing linkage group").

With respect to the hetexo atom-containing linkage group, the "hetero atom" is an atom other than a carbon atom and a hydrogen atom, and examples thereof include an oxygen atom, a sulfur atom and a nitrogen atom The alkylene group as the divalent linkage group may be linear or branched. The alkylene group preferably has 1 to 12 carbon atoms, more preferably 1 to 5, and most preferably 1 to 3.

Specific examples of the alkylene group include a methylene group [—$CH_2$—]; alkylmethylene groups such as —CH($CH_3$)—, —CH($CH_2CH_3$)—, —C($CH_3$)$_2$—, —C($CH_3$)($CH_2CH_3$)—, —C($C_3$)($CH_2CH_2CH_3$)— and —C($CH_2CH_3$)$_2$; an ethylene group [—$CH_2CH_2$—]; alkylethylene groups such as —CH($CH_3$)$CH_2$—, —CH($CH_3$)CH($CH_3$)—, —C($CH_3$)$_2CH_2$— and —CH($CH_2CH_3$)$CH_2$—; a trimethylene group (n-propylene group) [—$CH_2CH_2CH_2$—]; alkyltrimethylene groups such as —CH($CH_3$)$CH_2CH_2$— and —$CH_2$CH($CH_3$)$CH_2$—; a tetramethylene group [—$CH_2CH_2CH_2CH_2$—]; alkyltetramethylene groups such as —CH($CH_3$)$CH_2CH_2CH_2$— and —$CH_2$CH($CH_3$)$CH_2CH_2$—; and a pentamethylene group [—$CH_2CH_2CH_2CH_2CH_2$—].

As the hetero atom-containing linkage group, for example, non-hydrocarbon, hetero atom-containing linkage groups such as an oxygen atom (an ether bond; —O—), a sulfur atom (a thioether bond; —S—), an —NH— bond (the H may be replaced with a substituent such as an alkyl group or an acyl group), an ester bond (—C(=O)—O—), an amido bond (—C(=O)—NH—), a carbonyl group (—C(=O)—) and a carbonate bond (—O—C(=O)—O—); and combinations of the aforementioned non-hydrocarbon, hetero atom-containing linkage groups and the aforementioned alkylene groups, can be mentioned. Specific examples of the combinations of the aforementioned non-hydrocarbon, hetero atom-containing linkage groups and the aforementioned alkylene groups include —$R^{91}$—O—, —$R^{92}$—O—C(=O)—, —C(=O)—O—$R^{93}$— (wherein each of $R^{91}$ to $R^{93}$ independently represents an alkylene group), and combination of these groups. In the formulas above, as the alkylene group for $R^{91}$ to $R^{93}$, the same alkylene groups as those for the aforementioned divalent linkage groups can be mentioned.

As $Q^2$, a carbonyl group, a single bond or a group represented by the formula —$R^{92}$—O—C(=O)— is preferable.

As $Q^3$, a single bond, an alkylene group or a carbonyl group is preferable.

It is particularly desirable that $Q^2$ represent a carbonyl group and $Q^3$ represent a single bond, or $Q^2$ represent a single bond and $Q^3$ represent an alkylene group, or $Q^2$ represent —$R^{92}$—O—C(=O)— and $Q^3$ represent a cabonyl group.

In general formula (b0-1), $Y^1$ represents an alkylene group or fluorinated alkyl group of 1 to 4 carbon atoms.

As the alkylene group for $Y^1$, the alkylene groups for the divalent linkage group which have 1 to 4 carbon atoms can be mentioned. As the fluorinated alkyl group for $Y^1$, a group in which a part or all of the hydrogen atoms within the aforementioned alkylene group has been substituted with fluorine atoms can be mentioned.

Specific examples of $Y^1$ include —$CF_2$—, —$CF_2CF_2$—, —$CF_2CF_2CF_2$—, —CF($CF_3$)$CF_2$—, —CF($CF_2CF_3$)—, —C($CF_3$)$_2$—, —$CF_2CF_2CF_2CF_2$—, —CF($CF_3$)$CF_2CF_2$—, —$CF_2$CF($CF_3$)$CF_2$—, —CF($CF_3$)CF($CF_3$)—, —C($CF_3$)$_2CF_2$—, —CF($CF_2CF_3$)$CF_2$—, —CF($CF_2CF_2CF_3$)—, —C($CF_3$)($CF_2CF_3$)—; —CHF—, —$CH_2CF_2$—, —$CH_2CH_2CF_2$—, —$CH_2CF_2CF_2$—, —CH($CF_3$)$CH_2$—, —CH($CF_2CF_3$)—, —C($CH_3$)($CF_3$)—, —$CH_2CH_2CH_2CF_2$—, —$CH_2CH_2CF_2CF_2$—, —CH($CF_3$)$CH_2CH_2$—, —$CH_2$CH($CF_3$)$CH_2$—, —CH($CF_3$)CH($CF_3$)—, —C($CF_3$)$_2CH_2$—, —$CH_2$—, —$CH_2CH_2$—, —$CH_2CH_2CH_2$—, —CH($CH_3$)$CH_2$—, —CH($CH_2CH_3$)—, —C($CH_3$)$_2$—, —$CH_2CH_2CH_2CH_2$—, —CH($CH_3$)$CH_2CH_2$—, —$CH_2$CH($CH_3$)$CH_2$—, —CH($CH_3$)CH($CH_3$)—, —C($CH_3$)$_2CH_2$—, —CH($CH_2CH_3$)$CH_2$—, —CH($CH_2CH_2CH_3$)—, and —C($CH_3$)($CH_2CH_3$)—.

As $Y^1$, a fluorinated alkylene group is preferable, and a fluorinated alkylene group in which the carbon atom bonded to the adjacent sulfur atom is fluorinated is particularly desirable. Examples of such fluorinated alkylene groups include —$CF_2$—, —$CF_2CF_2$—, —$CF_2CF_2CF_2$—, —CF($CF_3$)$CF_2$—, —$CF_2CF_2CF_2CF_2$—, —CF($CF_3$)$CF_2CF_2$—, —$CF_2$CF($CF_3$)$CF_2$—, —CF($CF_3$)CF($CF_3$)—, —C($CF_3$)$_2CF_2$—, —CF($CF_2$—$CF_3$)$CF_2$—; —$CH_2CF_2$—, —$CH_2CH_2CF_2$—, —$CH_2CF_2CF_2$—; —$CH_2CH_2CH_2CF_2$)—, —$CH_2CH_2CF_2CF_2$—, and —$CH_2CF_2CF_2CF_2$—.

Among these, —$CF_2$—, —$CF_2CF_2$—, —$CF_2CF_2CF_2$—, and $CH_2CF_2CF_2$— are preferable, —$CF_2$—, —$CF_2CF_2$— and —$CF_2CF_2CF_2$— are more preferable, and —$CF_2$ is particularly desirable.

In general formula (b0-1), each of $R^3$ to $R^6$ independently represents a hydrogen atom or a hydrocarbon group which may have a substituent, with the proviso that at least one of $R^3$ to $R^6$ represents a hydrocarbon group.

As the hydrocarbon group for $R^3$ to $R^6$, the same hydrocarbon groups as those for $R^X$ above can be mentioned.

The hydrocarbon group may be either an aliphatic hydrocarbon group, or an aromatic hydrocarbon group. When the hydrocarbon group is an aliphatic hydrocarbon group, as the aliphatic hydrocarbon group, an alkyl group of 1 to 12 carbon atoms which may have a substituent is particularly desirable.

As the substituent which the hydrocarbon group may have, the same substituents as those which a hydrocarbon group for $R^X$ may have can be mentioned, and a hydroxyl group is particularly desirable. Also, a substituent containing a nitrogen atom, such as a nitrogen atom, a cyano group (—CN), an amino group (—NH$_2$) or an amido group (—NH—C(=O)—) can be mentioned.

At least one of $R^3$ to $R^6$ represents a hydrocarbon group, and it is preferable that two or three of $R^3$ to $R^6$ represents a hydrocarbon group.

At least two of $R^3$ to $R^6$ may be mutually bonded to form a ring. For example, two of $R^3$ to $R^6$ may be mutually bonded to form a ring, or three of $R^3$ to $R^6$ may be mutually bonded to form a ring, or two of $R^3$ to $R^6$ may be mutually bonded to form a ring, and the remaining two of $R^3$ to $R^6$ may be mutually bonded to form a ring, so as to form two rings.

The ring formed by at least two of $R^3$ to $R^6$ being mutually bonded together with the nitrogen atom within the formula (i.e., hetexo ring containing a nitrogen atom as the hetero atom) may be either an aliphatic hetero ring or an aromatic hetero ring. Further, the hetero ring may be either monocyclic or polycyclic.

Specific example of the cation moiety ($N^+(R^3)(R^4)(R^5)(R^6)$) within general formula (b0-1) includes an ammonium ion derived from an amine.

Here, "an ammonium ion derived from an amine" refers to an amine having a hydrogen atom bonded to the nitrogen atom to form a cation, or a quaternary ammonium ion which is an amine having an extra substituent bonded to the nitrogen atom.

The amine for deriving the above-mentioned ammonium ion may be either an aliphatic amine or an aromatic amine.

As the aliphatic amine, an amine in which at least one hydrogen atom of ammonia (NH$_3$) has been substituted with an alkyl group or hydroxyalkyl group of no more than 12 carbon atoms (i.e., alkylamines or alkylalcoholamines), or a cyclic amine is particularly desirable.

Specific examples of alkylamines and alkylalcoholamines include monoalkylamines such as n-hexylamine, n-heptylamine, n-octylamine, n-nonylamine, and n-decylamine; dialkylamines such as diethylamine, di-n-propylamine, di-n-heptylamine, di-n-octylamine, and dicyclohexylamine; trialkylamines such as trimethylamine, triethylamine, tri-n-propylamine, tri-n-butylamine, tri-n-hexylamine, tri-n-pentylamine, tri-n-heptylamine, tri-n-octylamine, tri-n-nonylamine, tri-n-decanylamine, and tri-n-dodecylamine; and alkyl alcohol amines such as diethanolamine, triethanolamine, diisopropanolamine, triisopropanolamine, di-n-octanolamine, and tri-n-octanolamine.

Examples of the cyclic amine include heterocyclic compounds containing a nitrogen atom as a hetero atom. The heterocyclic compound may be a monocyclic compound (aliphatic monocyclic amine), or a polycyclic compound (aliphatic polycyclic amine).

Specific examples of the aliphatic monocyclic amine include piperidine, and piperazine.

The aliphatic polycyclic amine preferably has 6 to 10 carbon atoms, and specific examples thereof include 1,5-diazabicyclo[4.3.0]-5-nonene, 1,8-diazabicyclo[5.4.0]-7-undecene, hexamethylenetetramine, and 1,4-diazabicyclo[2.2.2]octane.

Examples of aromatic amines include aniline, pyridine, 4-dimethylaminopyridine (DMAP), pyrrole, indole, pyrazole and imidazole.

Examples of quaternary ammonium ions include a tetramethylammonium ion, a tetraethylammonium ion and tetrabutylammonium ion.

In the present invention, with respect to the cation moiety ($N^+(R^3)(R^4)(R^5)(R^6)$) within general formula (b0-1), it is particularly desirable that at least one of $R^3$ to $R^6$ represent an alkyl group, and at least one represent a hydrogen atom.

Among such cation moieties, a cation moiety in which three of $R^3$ to $R^6$ represent an alkyl group and the remaining one represents a hydrogen atom (trialkylammonium ion), or a cation moiety in which two of $R^3$ to $R^6$ represent an alkyl group and one of the remaining two represents a hydrogen atom (dialkylammonium ion) is preferable.

It is preferable that each of the alkyl groups within the trialkylammonium ion or dialkylammonium ion independently have 1 to 10 carbon atoms, more preferably 1 to 8, and most preferably 1 to 5. Specific examples of alkyl groups include a methyl group, an ethyl group, a propyl group, a butyl group, a pentyl group, a hexyl group, a heptyl group, an octyl group, a nonyl group and a decanyl group. Among these, an ethyl group is particularly desirable.

In the present invention, it is preferable that the compound (b0-1) be represented by general formula (b0-1-1) shown below, and it is particularly desirable the compound (b0-1) be represented by general formula (b0-1-11) or (b0-1-12) shown below.

[Chemical Formula 14]

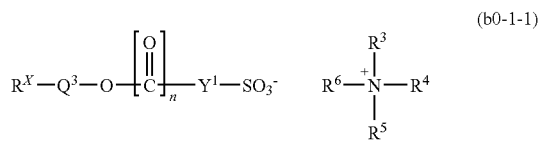

(b0-1-1)

wherein $R^X$, $Q^3$, $Y^1$ and $R^3$ to $R^6$ are respectively as defined for $R^X$, $Q^3$, $Y^1$ and $R^3$ to $R^6$ in general formula (b0-1); and n represents 0 or 1.

[Chemical Formula 15]

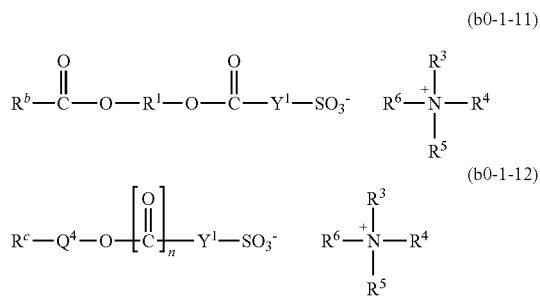

wherein n, $Y^1$ and $R^3$ to $R^6$ are respectively as defined for n, $Y^1$ and $R^3$ to $R^6$ in general formula (b0-1-1) above; $R^1$ represents an alkylene group; each of $R^b$ and $R^c$ independently represents a hydrocarbon group which may have a substituent exclusive of a nitrogen atom; and $Q^4$ represents a single bond or an alkylene group.

In general formula (b0-1-11), as $R^b$, the same groups as those for $R^x$ above can be mentioned, and a linear or branched saturated hydrocarbon group which may have a substituent, an aliphatic cyclic group which may have a substituent, or an aromatic hydrocarbon group which may have a substituent is preferable. Among these, a linear saturated hydrocarbon group or an aliphatic cyclic group which may have a substituent is preferable.

As the alkylene group for $R^1$, a linear or branched alkylene group is preferable, and the alkylene group preferably has 1 to 12 carbon atoms, more preferably 1 to 5, and most preferably 1 to 3. Specific examples of alkylene groups include the same alkylene groups as those mentioned above for the aforementioned divalent linkage group.

In general formula (b0-1-12), as $R^c$, the same groups as those for $R^x$ above can be mentioned, and an aliphatic cyclic group which may have a substituent, or an aromatic hydrocarbon group which way have a substituent is preferable. Among these, an aliphatic cyclic group having a hetero atom-containing substituent group in the ring structure thereof is preferable.

As the alkylene group for $Q^4$, the same alkylene groups as those for the aforementioned divalent linkage group can be mentioned.

n is preferably 1.

As the compound (b0-1), compounds represented by general formulas (b0-1-21), (b0-1-22) and (b0-1-31) to (b0-1-35) are particularly desirable.

[Chemical Formula 16]

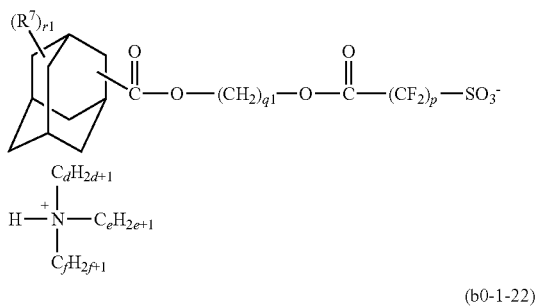
(b0-1-21)

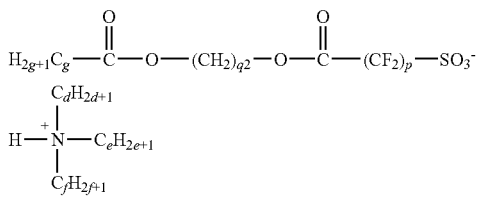
(b0-1-22)

wherein each of d, e and f independently represents an integer of 1 to 10; p represents an integer of 1 to 3; each of q1 and q2 independently represents an integer of 1 to 5; r1 represents an integer of 0 to 3; g represents an integer of 1 to 20; and $R^7$ represents a substituent.

[Chemical Formula 17]

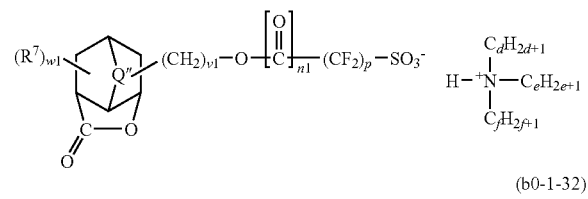
(b0-1-31)

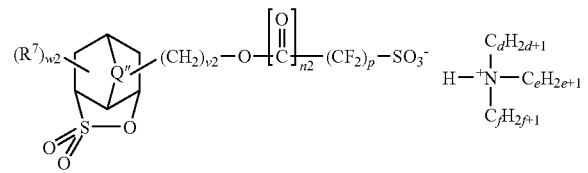
(b0-1-32)

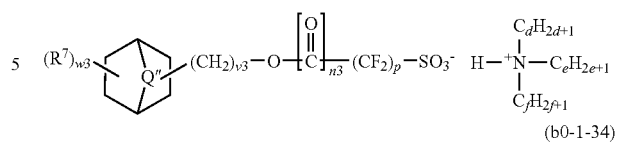
(b0-1-33)

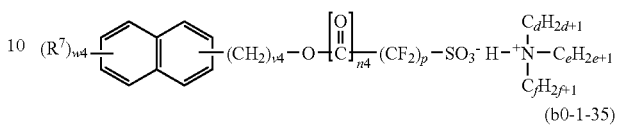
(b0-1-34)

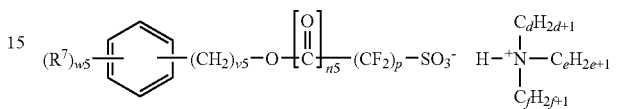
(b0-1-35)

wherein Q", d, e, f and p are as defined above; each of n1 to n3 independently represents 0 or 1; each of v1 to v5 independently represents an integer of 0 to 3; each of w1 to w5 independently represents an integer of 0 to 3; and $R^7$ represents a substituent.

As the substituent for $R^7$, the same groups as those which the aforementioned aliphatic hydrocarbon group or aromatic hydrocarbon group for $R^x$ may have can be mentioned.

When the subscript of $R^7$ (r1 and w1 to w5) represents an integer of 2 or more, the plurality of $R^7$ may be the same or different.

The compound (b0-1) of the present invention is a novel compound.

The compound (b0-1) of the present invention is useful as an intermediate in the synthesis of a compound useful as an acid generator for a resist composition (especially the compound (b1-1) according to the third aspect of the present invention).

The compound (b0-1) of the present invention can be produced, for example, by the production method (1) of the compound (b0-1) according to the seventh aspect of the present invention described below, or the production method (2) of the compound (b0-1) according to the eighth aspect of the present invention described below.

<<Production Method (1) of the Compound (b0-1)>>

Next, the production method (1) of the compound (b0-1) according to the seventh aspect of the present invention will be described.

The production method (1) of the compound (b0-1) according to the present invention includes reacting a compound (1-11) represented by general formula (1-11) shown below and a compound (1-12) represented by general formula (1-12) shown below with an amine or an ammonium salt.

[Chemical Formula 18]

$$HO-Q^2-Y^1-SO_3^- M^+ \quad (1\text{-}11)$$

$$R^X-Q^3-X^{21} \quad (1\text{-}12)$$

$$R^X-Q^3-O-Q^2-Y^1-SO_3^- \quad R^6-\overset{+}{\underset{R^5}{\underset{|}{N}}}-R^4 \quad (b0\text{-}1)$$

wherein $R^x$, $Q^2$, $Q^3$, $Y^1$ and $R^3$ to $R^6$ are respectively as defined for $R^x$, $Q^2$, $Q^3$, $Y^1$ and $R^3$ to $R^6$ in general formula (b0-1) above; $X^{21}$ represents a halogen atom; and $M^+$ represents an alkali metal ion.

In general formula (1-11), as $M^+$ a sodium ion, a potassium ion, a lithium ion and the like can be mentioned.

As the compound (1-11), a commercially available compound may be used, or the compound may be synthesized.

For example, a compound (1-11) in which $Q^2$ in general formula (1-11) represents a carbonyl group (hereafter, referred to as "compound (1-11-1)") can be produced by a method including: heating a compound (0-1) represented by general formula (0-1) shown below in the presence of an alkali, and neutralizing the resultant, thereby obtaining a compound (0-2) represented by general formula (0-2) shown below (hereafter, this step is referred to as "salt-formation step"); and heating the compound (0-2) in the presence of an acid having an acid strength stronger than that of the compound (1-11-1) thereby obtaining the compound (1-11-1) (hereafter, this step is referred to as "carboxylic acid-generation step").

[Chemical Formula 19]

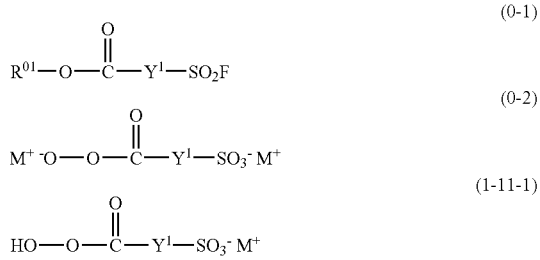

wherein $R^{01}$ represents an alkyl group; and $Y^1$ and $M^+$ are as defined above.

As the alkyl group for $R^{01}$, a linear or branched alkyl group is preferable, and specific examples include a methyl group, an ethyl group, a propyl group, an isopropyl group, an n-butyl group, an isobutyl group, a tert-butyl group, a pentyl group, an isopentyl group and a neopentyl group.

Among these, an alkyl group of 1 to 4 carbon atoms is preferable, and a methyl group is particularly desirable.

As the compound (0-1), a commercially available compound can be used.

The salt-formation step can be performed, for example, by dissolving the compound (0-1) in a solvents and adding an alkali to the resulting solution, followed by heating.

As the solvent, any solvent which is capable of dissolving the compound (0-1) can be used. Examples of such a solvent include water and tetrahydrofuran.

As the alkali, an alkali corresponding to M in formula (0-2) is used. Examples of such an alkali include alkali metal hydroxides such as sodium hydroxide, potassium hydroxide and lithium hydroxide.

The amount of the alkali is preferably 1 to 5 moles, more preferably 2 to 4 moles, per 1 mole of the compound (0-1).

The heating temperature is preferably 20 to 120° C., and more preferably 50 to 100° C. The heating time depends on the heating temperature and the like, but in general, the heating time is preferably 0.5 to 12 hours, and more preferably 1 to 5 hours.

The neutralization following the heating can be conducted by adding an acid such as hydrochloric acid, sulfuric acid, p-toluenesulfonic acid, or the like to the reaction liquid following the heating.

It is preferable to conduct the neutralization so that the pH of the reaction liquid (25° C.) after addition of an acid falls within the range of 6 to 8. Further, the temperature of the reaction liquid during the neutralization is preferably 20 to 30° C., and more preferably 23 to 27° C.

After the reaction, the compound (0-2) within the reaction liquid may be separated and purified. The separation and purification can be conducted by a conventional method. For example, any one of concentration, solvent extraction, distillation, crystallization, recrystallization and chromatography can be used alone, or two or more of these methods may be used in combination.

In the carboxylic acid-generation step, the compound (0-2) obtained in the salt-formation step is heated in the presence of an acid having an acid strength stronger than that of the compound (1-11-1), thereby obtaining the compound (1-11-1).

"An acid having an acid strength stronger than that of the compound (1-11-1)" (hereafter, frequently referred to simply as "strong acid") refers to an acid having a pKa value (25° C.) smaller than that of —COOH within the compound (1-11-1). By using such a strong acid, —COO$^-$M$^+$ within the compound (0-2) can be converted into —COOH, thereby obtaining the compound (1-11-1).

The strong acid can be appropriately selected from any conventional acids which exhibit a pKa value smaller than that of —COOH within the compound (1-11-1). The pKa value of —COOH within the compound (1-11-1) can be determined by a conventional titration method.

Specific, examples of strong acids include a sulfonic acids such as an arylsulfonic acid or an alkylsulfonic acid; sulfuric acid; and hydrochloric acid. An example of an arylsulfonic acid includes p-toluenesulfonic acid. Examples of alkylsulfonic acids include methanesulfonic acid and trifluoromethane sulfonic acid. In consideration of solubility in an organic solvent and ease in purification, p-toluenesulfonic acid is particularly desirable as the strong acid.

The carboxylic acid-generation step can be performed, for example, by dissolving the compound (0-2) in a solvent, and adding a strong acid to the resulting solution, followed by heating.

As the solvent, any solvent which is capable of dissolving the compound (0-2 can be used. Examples of such solvents include acetonitrile and methyl ethyl ketone.

The amount of the strong acid is preferably 0.5 to 3 moles, and more preferably 1 to 2 moles, per 1 mole of the compound (0-2).

The heating temperature is preferably 20 to 150° C., and more preferably 50 to 120° C. The heating time depends on the heating temperature and the like, but in general, the heating time is preferably 0.5 to 12 hours, and more preferably 1 to 5 hours.

After the reaction, the compound (1-11-1) within the reaction liquid may be separated and purified. The separation and purification can be conducted by a conventional method. For example any one of concentration, solvent extraction, distillation, crystallization, recrystallization and chromatography can be used alone, or two or more of these methods may be used in combination.

Alternatively a compound (1-11) in which $Q^2$ in general formula (1-11) represents —R$^1$—O—C(=O)— (wherein R$^1$ is as defined for R$^{92}$ above (i.e., an alkylene group)) (hereafter, this compound is referred to as "compound (1-11-2)") can be produced, for example, by a method including: reacting a compound (0-3) represented by general formula (0-3) with the aforementioned compound (1-11-1), thereby obtaining a compound (1-11-2).

[Chemical Formula 20]

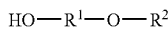
(0-3)

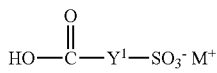
(1-11-1)

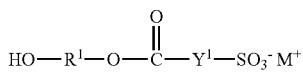
(1-11-2)

wherein $R^1$ represents an alkylene group; $R^2$ represents a aliphatic group which may have an aromatic group as a substituent; $Y^1$ represents an alkylene group or fluorinated alkyl group of 1 to 4 carbon atoms; and $M^+$ represents an alkali metal ion.

The method of reacting the compound (0-3) with the compound (1-11-1) is not particularly limited, and can be performed, for example, by mixing and dissolving the compound (0-3) and the compound (1-11-1) in a solvent, and heating the resulting solution.

Examples of solvents include toluene, dichlorobenzene, 1,2-dichloroethane and 1,3-dichloropropane.

The heating temperature (reaction temperature) is preferably about 20 to 140° C., and more preferably 60 to 130° C. The heating time depends on the heating temperature and the like, but in general, the heating time is preferably 1 to 72 hours, and more preferably 6 to 48 hours.

The reaction may be performed in the presence of an acidic catalyst. As the acid catalyst, there is no particular limitation, and examples thereof include a sulfonic acid, such as an arylsulfonic acid or an alkylsulfonic acid; sulfuric acid; and hydrochloric acid. An example of an arylsulfonic acid includes p-toluenesulfonic acid. Examples of alkylsulfonic acids include methanesulfonic acid and trifluoromethane sulfonic acid. These acids may be used individually or in a combination of two or more acids. In consideration of solubility in an organic solvent and ease in purification, p-toluenesulfonic acid is particularly desirable.

The amount of the acidic catalyst is preferably 0.1 to 2 moles, and more preferably 0.1 to 1 mole, per 1 mole of the compound (1-11-1).

After the reaction, the compound (1-11-2) within the reaction liquid may be separated and purified. The separation and purification can be conducted by a conventional method. For example, any one of concentration, solvent extraction, distillation, crystallization, recrystallization and chromatography can be used alone, or two or more of these methods may be used in combination.

In general formula (1-12), as the halogen atom for $X^{21}$, a bromine atom, a chlorine atom, an iodine atom and a fluorine atom can be mentioned. As the halogen atom for $X^{21}$, in terms of reactivity, a bromine atom or a chlorine atom is preferable.

As the compound (1-12), a commercially available compound can be used.

As the amine or the ammonium salt an amine or ammonium salt corresponding to the cation moiety $(N^+(R^3)(R^4)(R^5)(R^6))$ in general formula (b0-1) is used. Specific examples of such amines include alkylamines, dialkylamines, trialkylamines and aromatic amines which have been mentioned above as amines for deriving the aforementioned ammonium ion. Specific examples of ammonium salts include quaternary ammonium salts such as tetramethylammonium hydroxide, tetraethylammonium hydroxide and tetrabutylammonium hydroxide.

The method of reacting the compound (1-11) and the compound (1-12) with an amine or an ammonium salt is not particularly limited, and can be performed, for example, by contacting the compound (1-11), the compound (1-12) and an amine or an ammonium salt in a reaction solvent. Such a method can be performed, for example, by adding the compound (1-12) and an amine or a quaternary ammonium salt to a solution obtained by dissolving the compound (1-11) in a reaction solvent.

As the reaction solvent, any solvent which is capable of dissolving the compound (1-11) and the compound (1-12) can be used. Specific examples of such solvents include tetrahydrofuran (THF), acetone, dimethylformamide (DMF), dimethylacetamide, dimethylsulfoxide (DMSO) and acetonitrile.

The amount of the compound (1-12) is preferably 1 to 3 equivalents, and more preferably 1 to 2 equivalents, based on the mount of the compound (1-11).

The amount of the amine or the quaternary ammonium salt is preferably 1 to 3 equivalents, and more preferably 1 to 2 equivalents, based on the amount of the compound (1-11).

The reaction temperature is preferably −20 to 40° C., and more preferably 0 to 30° C. The reaction time depends on the reactivity of the compound (1-11) and the compound (1-12), the reaction temperature, and the like, but in general, the reaction temperature is preferably 1 to 120 hours, and more preferably 1 to 48 hours.

After the reaction, the compound (b0-1) within the reaction liquid may be separated and purified. The separation and purification can be conducted by a conventional method. For example, any one of concentration, solvent extraction, distillation, crystallization, recrystallization and chromatography can be used alone, or two or more of these methods may be used in combination.

In the present invention, as the compound (b0-1) has $N^+(R^3)(R^4)(R^5)(R^6)$ as the cation moiety, the compound (b0-1) is hardly soluble in water. Therefore, the compound (b0-1) can be purified by washing with water.

The structure of the compound (b0-1) obtained in the above-described manner can be confirmed by a general organic analysis method such as $^1$H-nuclear magnetic resonance (NMR) spectrometry, $^{13}$C-NMR spectrometry, $^{19}$F-NMR spectrometry, infrared absorption (IR) spectrometry, mass spectrometry (MS), elementary analysis and X-ray diffraction analysis.

<<Production Method (2) of Compound (b0-1), Compound (1-21)>>

Next, the production method (2) of the compound (b0-1) according to the eighth aspect of the present invention and the compound (1-21) according to the ninth aspect of the present invention will be described.

The production method (2) of the compound (b0-1) according to the present invention includes reacting a compound (1-21) represented by general formula (1-21) shown below and a compound (1-12) represented by general formula (1-12) shown below with an amine or an ammonium salt, thereby obtaining a compound (b0-1) represented by general formula (b0-1) shown below.

[Chemical Formula 21]

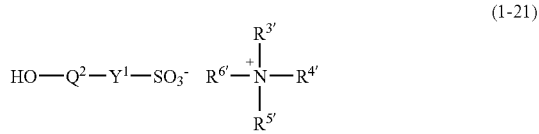

(1-21)

(1-12)

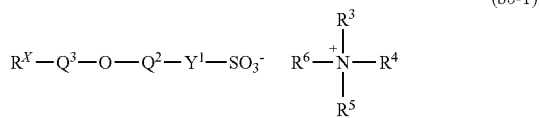

(b0-1)

wherein $R^x$, $Q^2$, $Q^3$, $Y^1$ and $R^3$ to $R^6$ are respectively as defined for $R^x$, $Q^2$, $Q^3$, $Y^1$ and $R^3$ to $R^6$ in general formula (b0-1) above; each of $R^{3'}$ to $R^{6'}$ independently represents a hydrogen atom or a hydrocarbon group which may have a substituent, with the proviso that at least one of $R^{3'}$ to $R^{6'}$ represents a hydrocarbon group; and at least two of $R^{3'}$ to $R^{6'}$ may be mutually bonded to form a ring; and $X^{21}$ represents a halogen atom.

In general formula (1-21), as $R^{3'}$ to $R^{6'}$, the same groups as those for $R^3$ to $R^6$ above can be mentioned.

In the production method (2) according to the eighth aspect, the cation moiety $(N^+(R^{3'})(R^{4'})(R^{5'})(R^{6'}))$ in general formula (1-21) and the cation moiety $(N^+(R^3)(R^4)(R^5)(R^6))$ in general formula (b0-1) may be the same or different. In terms of simplifying the production steps, it is preferable that the cation moieties be the same.

The step of reacting a compound (1-21) and a compound (1-12) with an amine or an ammonium salt can be performed in the same manner as in the aforementioned production method (1), except that a compound (1-21) is used instead of a compound (1-11).

The compound (1-21) used as a starting material in the production method (2) according to the eighth aspect is a novel compound.

The compound (1-21) can be produced, for example, by the production method of compound (1-21) described below.

<<Production Method of Compound (1-21)>>

Next, the production method of compound (1-21) according to the tenth aspect of the present invention will be described.

The production method of compound (1-21) includes reacting a compound (1-11) represented by general formula (1-11) shown below with an ammonium salt.

[Chemical Formula 22]

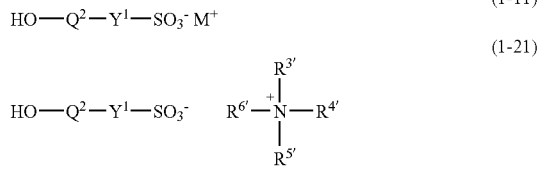

In general formulas (1-11) and (1-21), $Q^2$, $Y^1$, $R^{3'}$ to $R^{6'}$ and $M^+$ are as defined above.

Examples of ammonium salts include the aforementioned alkylamines, dialkylamines, trialkylamines, and a hydrochloride or bromate of an aromatic amine.

The reaction between a compound (1-11) and an ammonium salt can be conducted in the same manner as in a conventional salt substitution method. For example, a compound (1-11) and an ammonium salt can be dissolved in a solvent such as water, dichloromethane, acetonitrile, methanol or chloroform, followed by stirring or the like.

The reaction temperature is preferably 0 to 150° C., and more preferably 0 to 100° C. The reaction time depends on the reactivity of the compound (1-11) and the ammonium salt, reaction temperature, or the like, but in general, the reaction time is preferably 0.5 to 10 hours, more preferably 1 to 5 hours.

After the reaction, the compound (1-21) within the reaction liquid may be separated and purified. The separation and purification can be conducted by a conventional method. For example, any one of concentration, solvent extraction, distillation, crystallization, recrystallization and chromatography can be used alone, or two or more of these methods may be used in combination.

The structure of the compound (1-21) obtained in the above-described manner can be confirmed by a general organic analysis method such as $^1$H-nuclear magnetic resonance (NMR) spectrometry, $^{13}$C-NMR spectrometry, $^{19}$F-NMR spectrometry, infrared absorption (IR) spectrometry, mass spectrometry (MS), elementary analysis and X-ray diffraction analysis.

<<Production Method of Compound (1-14)>>

Next, the production method of compound (1-14) according to the eleventh aspect of the present invention will be described.

The production method of compound (1-14) includes reacting a compound (1-13) represented by general formula (1-13) shown below with an ammonium salt,

[Chemical Formula 23]

(1-13)

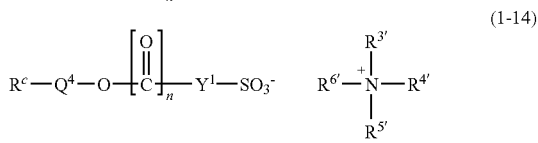

(1-14)

wherein $R^c$ represents a hydrocarbon group which may have a substituent exclusive of a nitrogen atom; $Q^4$ represents a single bond or a divalent linkage group; n represents 0 or 1; $Y^1$ represents an alkylene group or fluorinated alkyl group of 1 to 4 carbon atoms; each of $R^{3'}$ to $R^{6'}$ independently represents a hydrogen atom or a hydrocarbon group which may have a substituent, with the proviso that at least one of $R^{3'}$ to $R^{6'}$ represents a hydrocarbon group; and at least two of $R^{3'}$ to $R^{6'}$ may be mutually bonded to form a ring; and $M^+$ represents an alkali metal ion.

In general formulas (1-13) and (1-14) above, $R^c$, $Q^4$, n, $Y^1$, $R^{3'}$ to $R^{6'}$ and $M^+$ are as defined above.

Examples of ammonium salts include the aforementioned alkylamines, dialkylamines, trialkylamines, and a hydrochloride or bromate of an aromatic amine.

The reaction between a compound (1-13) and an ammonium salt can be conducted in the same manner as in a conventional salt substitution method. For example, a compound (1-13) can be dissolved in a solvent such as water, dichloromethane, acetonitrile, methanol or chloroform, followed by stirring or the like.

The reaction temperature is preferably 0 to 150° C., and more preferably 0 to 100° C. The reaction time depends on the reactivity of the compound (1-13) and the ammonium salt, the reaction temperature, or the like, but in general, the reaction time is preferably 0.5 to 10 hours, more preferably 1 to 5 hours.

After the reaction, the compound (1-14) within the reaction liquid may be separated and purified. The separation and purification can be conducted by a conventional method. For example, any one of concentration, solvent extraction, distillation, crystallization, recrystallization and chromatography can be used alone, or two or more of these methods may be used in combination.

In the present invention, as the compound (1-14) has $N^+(R^{3\prime})(R^{4\prime})(R^{5\prime})(R^{6\prime})$ as the cation moiety, the compound (1-14) is hardly soluble in water. Therefore, the compound (1-14) can be purified by washing with water.

The structure of the compound (1-14) obtained in the above-described manner can be confirmed by a general organic analysis method such as $^1$H-nuclear magnetic resonance (NMR) spectrometry, $^{13}$C-NMR spectrometry, $^{19}$F-NMR spectrometry, infrared absorption (IR) spectrometry, mass spectrometry (MS), elementary analysis and X-ray diffraction analysis.

<<Application of Compound (b0-1)>>

As described above, the compound (b0-1) of the present invention is a novel compound, and is useful as an intermediate in the synthesis of a compound useful as an acid generator for a resist composition (especially the compound (b1-1) according to the third aspect of the present invention).

More specifically, by conducting a salt substitution of the compound (b0-1) of the present invention to substitute the cation moiety ($N^+(R^3)(R^4)(R^5)(R^6)$) of the compound (b0-1) with an appropriate cation moiety, e.g., an organic cation such as a sulfonium ion or an iodonium ion, a compound which generates acid (sulfonic acid) upon exposure can be obtained. Such a compound is useful as an acid generator for a resist composition.

Thus, the compound (b0-1) of the present invention is useful as an intermediate in the production of a compound useful as an acid generator by conducting salt substitution of the compound (b0-1). As the compound (b0-1) has $N^+(R^3)(R^4)(R^5)(R^6)$ as the cation moiety, the compound (b0-1) can be easily purified by washing with water, and hence, improvement in the purity of the final product can be expected. For example, with respect to a compound in which the cation moiety is an alkali metal ion, purification by washing with water is difficult because the compound gets dissolved in water.

Further, a compound produced by salt substitution of the compound (b0-1) of the present invention is not only useful as an acid generator, but also, when the compound is blended within a resist composition as an acid generator, the compound contributes to improvement in various lithography properties of the resist composition. For example, when a resist pattern is formed from such a resist composition, resolution, mask reproducibility (e.g., mask linearity or the like), exposure margin (EL margin), pattern shape, depth of focus (DOF), and the like are improved.

The EL margin is the range of the exposure dose at which a resist pattern can be formed with a size within a predetermined range of variation from a target size, when exposure is conducted by changing the exposure dose, i.e., the range of the exposure dose at which a resist pattern faithful to the mask pattern can be formed. The larger the exposure margin, the smaller the variation in the pattern size depending on the change in the exposure dose, thereby resulting in favorable improvement in the process margin.

The reason why the aforementioned effects can be achieved is presumed as follows. The compound produced by salt substitution of the compound (b0-1) has a structure in which the skeleton "$Y^1$—$SO_3^-$" within the anion moiety has $R^x$-$Q^3$-O-$Q^2$- bonded thereto. As a result, the anion moiety of such a component exhibits a high polarity and has a three-dimensionally bulky structure, as compared to a fluorinated alkylsulfonic ion which has been conventionally used as an anion moiety. By virtue of the intermolecular force due to the high polarity, and the three-dimensionally bulky structure, it is presumed that diffusion of the anion moiety (acid) within the resist film is chemically and physically suppressed, as compared to the anion moiety of a conventional acid generator such as nonafluorobutanesulfonate. Therefore, by using such a compound, diffusion of the acid generated in the exposed regions to the unexposed regions can be suppressed, and hence, the difference in alkali solubility between the exposed regions and the unexposed regions (i.e., dissolution contrast) can be improved, and it is presumed that resolution and resist pattern shapes can be improved.

Furthermore, the alkyl chain of the alkylene group or fluorinated alkyl group for $Y^1$ which may have a substituent exhibits an excellent decomposability, as compared to, for example, a perfluoroalkyl chain of 6 to 10 carbon atoms. Therefore, the effect of minimizing bioaccumulation to improve ease of handling can be achieved.

As an example of a compound which is produced from the compound (b0-1) of the present invention as an intermediate and is useful as an acid generator for a resist composition, the compound (b1-1) of the present invention described below can be mentioned.

<<Compound (b1-1)>>

Next, the compound (b1-1) according to the third aspect of the present invention will be described. The compound (b1-1) is preferably used as an acid generator for the resist composition according to the first aspect of the present invention.

In general formula (b1-1) above, $R^x$, $Y^1$, $Q^2$ and $Q^3$ are respectively as defined for $R^x$, $Y^1$, $Q^2$ and $Q^3$ in general formula (b0-1).

As the organic cation for $Z^+$, there is no particular limitation as long as it is a cation other than an ion represented by general formula (w-1) above, and any of those conventionally known as cation moiety for an onium salt-based acid generator can be appropriately selected for use. As the cation moiety for $Z^+$, a sulfonium ion or an iodonium ion is preferable, and a sulfonium ion is particularly desirable.

More specifically, a cation moiety represented by general formula (b'-1), (b'-2), (b-5) or (b-6) shown below can be preferably used.

[Chemical Formula 24]

wherein $R^{1\prime\prime\prime}$ to $R^{3\prime\prime\prime}$, $R^{5\prime\prime\prime}$ and $R^{6\prime\prime\prime}$ each independently represents an aryl group or alkyl group, wherein two of $R^{1\prime\prime\prime}$ to $R^{3\prime\prime\prime}$ in formula (b'-1) may be bonded to each other to form a ring with the sulfur atom, with the proviso that at least one of $R^{1\prime\prime\prime}$ to $R^{3\prime\prime\prime}$ represents an aryl group, and at least one of $R^{5\prime\prime\prime}$ and $R^{6\prime\prime\prime}$ represents an aryl group.

[Chemical Formula 25]

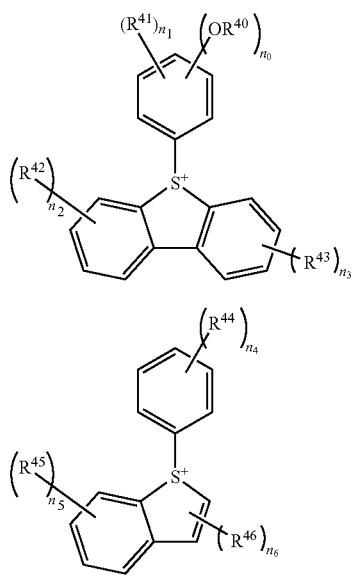

wherein $R^{40}$ represents a hydrogen atom or an alkyl group; $R^{41}$ represents an alkyl group, an acetyl group, a carboxy group or a hydroxyalkyl group; each of $R^{42}$ to $R^{46}$ independently represents an alkyl group, an acetyl group, an alkoxy group, a carboxy group, a hydroxyl group or a hydroxyalkyl group; each of $n_0$ to $n_5$ independently represents an integer of 0 to 3, with the proviso that $n_0+n_1$ is 5 or less; and $n_6$ represents an integer of 0 to 2.

In formula (b'-1), $R^{1\prime\prime\prime}$ to $R^{3\prime\prime\prime}$ each independently represents an aryl group or an alkyl group. In formula (b'-1), two of $R^{1\prime\prime\prime}$ to $R^{3\prime\prime\prime}$ may be bonded to each other to form a ring with the sulfur atom.

Further, among $R^{1\prime\prime\prime}$ to $R^{3\prime\prime\prime}$, at least one group represents an aryl group. Among $R^{1\prime\prime\prime}$ to $R^{3\prime\prime\prime}$, two or more groups are preferably aryl groups, and it is particularly desirable that all of $R^{1\prime\prime\prime}$ to $R^{3\prime\prime\prime}$ are aryl groups.

The aryl group for $R^{1\prime\prime\prime}$ to $R^{3\prime\prime\prime}$ is not particularly limited. Examples thereof include an unsubstituted aryl group having 6 to 20 carbon atoms, a substituted aryl group in which a part or all of the hydrogen atoms of the aforementioned unsubstituted aryl group has been substituted with alkyl groups, alkoxy groups, alkoxyalkyloxy groups, alkoxycarbonylalkyloxy groups, halogen atoms, hydroxyl groups or the like, and —($R^{4\prime}$)—C—(=O)—$R^{5\prime}$. $R^{4\prime}$ represents an alkylene group of 1 to 5 carbon atoms. $R^{5\prime}$ represents an aryl group. As the aryl group for $R^{5\prime}$, the same as the aryl group for $R^{1\prime\prime\prime}$ to $R^{3\prime\prime\prime}$ can be exemplified.

The unsubstituted aryl group is preferably an aryl group having 6 to 10 carbon atoms because it can be synthesized at a low cost. Specific examples thereof include a phenyl group and naphthyl group.

The alkyl group as the substituent for the substituted aryl group is preferably an alkyl group having 1 to 5 carbon atoms, and most preferably a methyl group, an ethyl group, a propyl group, an n-butyl group, or a tert-butyl group.

The alkoxy group as the substituent for the substituted aryl group is preferably an alkoxy group having 1 to 5 carbon atoms, and most preferably a methoxy group, ethoxy group, n-propoxy group, iso-propoxy group, n-butoxy group or tert-butoxy group.

The halogen atom as the substituent for the substituted aryl group is preferably a fluorine atom.

Examples of the alkoxyalkyloxy group as the substituent for the substituted aryl group include a group represented by a general formula: —O—C($R^{47}$)($R^{48}$)—O—$R^{49}$ (wherein each of $R^{47}$ and $R^{48}$ independently represents a hydrogen atom or a linear or branched alkyl group; and $R^{49}$ represents an alkyl group).

The alkyl group for $R^{47}$ and $R^{48}$ preferably has 1 to 5 carbon atoms, and may be either linear or branched, and is preferably an ethyl group or a methyl group, and most preferably a methyl group.

It is preferable that at least one of $R^{47}$ and $R^{48}$ be a hydrogen atom, and it is particularly desirable that either one of $R^{47}$ and $R^{48}$ be a hydrogen atom, and the other be a hydrogen atom or a methyl group.

The alkyl group for $R^{49}$ preferably has 1 to 15 carbon atoms, and may be linear, branched or cyclic.

The linear or branched alkyl group for $R^{49}$ preferably has 1 to 5 carbon atoms. Examples thereof include a methyl group, ethyl group, propyl group, n-butyl group and tert-butyl group.

The cyclic alkyl group for $R^{49}$ preferably has 4 to 15 carbon atoms, more preferably 4 to 12 carbon atoms, and most preferably 5 to 10 carbon atoms. Specific examples thereof include groups in which one or more hydrogen atoms have been removed from a monocycloalkane or a polycycloalkane such as a bicycloalkane, tricycloalkane or tetracycloalkane, and which may or may not be substituted with alkyl groups of 1 to 5 carbon atoms, fluorine atoms or fluorinated alkyl groups. Examples of the monocycloalkane include cyclopentane and cyclohexane. Examples of polycycloalkane include adamantane, norbornane, isobornane, tricyclodecane and tetracyclododecane. Among these, groups in which one or more hydrogen atoms have been removed from adamantane are preferable.

An example of the alkoxycarbonylalkyloxy group as the substituent for the substituted aryl group includes a group represented by a general formula: —O—$R^{50}$—C(=O)—O—$R^{51}$ (wherein $R^{50}$ represents a linear or branched alkylene group; and $R^{51}$ represents a tertiary alkyl group).

The linear or branched alkylene group for $R^{50}$ preferably has 1 to 5 carbon atoms, and examples thereof include a methylene group, ethylene group, trimethylene group, tetramethylene group and 1,1-dimethylethylene group.

Examples of tertiary alkyl groups for $R^{51}$ include 2-methyl-2-adamantyl group, 2-ethyl-2-adamantyl group, 1-methyl-1-cyclopentyl group, 1-ethyl-1-cyclopentyl group, 1-methyl-1-cyclohexyl group, 1-ethyl-1-cyclohexyl group, 1-(1-adamantyl)-1-methylethyl group, 1-(1-adamantyl)-1-methylpropyl group, 1-(1-adamantyl)-1-methylbutyl group, 1-(1-adamantyl)-1-methylpentyl group, 1-(1-cyclopentyl)-1-methylethyl group, 1-(1-cyclopentyl)-1-methylpropyl group, 1-(1-cyclopentyl)-1-methylbutyl group, 1-(1-cyclopentyl)-1-methylpentyl group, 1-(1-cyclohexyl)-1-methylethyl group, 1-(1-cyclohexyl)-1-methylpropyl group, 1-(1-cyclohexyl)-1-methylbutyl group, 1-(1-cyclohexyl)-1-methylpentyl group, tert-butyl group, tert-pentyl group ad tert-hexyl group.

The aryl group for $R^{1\prime\prime\prime}$ to $R^{3\prime\prime\prime}$ is preferably a phenyl group or a naphthyl group.

The alkyl group for $R^{1\prime\prime\prime}$ to $R^{3\prime\prime\prime}$ is not particularly limited and includes, for example a linear; branched or cyclic alkyl group having 1 to 10 carbon atoms. In terms of achieving excellent resolution, the alkyl group preferably has 1 to 5 carbon atoms. Specific examples thereof include a methyl group, an ethyl group, an n-propyl group, an isopropyl group, an n-butyl group, an isobutyl group, an n-pentyl group, a cyclopentyl group, a hexyl group, a cyclohexyl group, a nonyl group, and a decanyl group. Among these, a methyl; group is preferable because it is excellent in resolution and can be synthesized at a low cost.

When two of $R^{1\prime\prime\prime}$ to $R^{3\prime\prime\prime}$ are bonded to each other to form a ring with the sulfur atom, it is preferable that the two of $R^{1\prime\prime\prime}$ to $R^{3\prime\prime\prime}$ form a 3 to 10-membered ring including the sulfur atom, and it is particularly desirable that the two of $R^{1\prime\prime\prime}$ to $R^{3\prime\prime\prime}$ form a 5 to 7-membered ring including the sulfur atom.

When two of $R^{1\prime\prime\prime}$ to $R^{3\prime\prime\prime}$ are bonded to each other to form a ring with the sulfur atom, the remaining one of $R^{1\prime\prime\prime}$ to $R^{3\prime\prime\prime}$ is preferably an aryl group. As examples of the aryl group, the same as the above-mentioned aryl groups for $R^{1\prime\prime\prime}$ to $R^{3\prime\prime\prime}$ can be exemplified.

Specific examples of cation moiety represented by general formula (b'-1) include triphenylsulfonium, (3,5-dimethylphenyl)diphenylsulfonium, (4-(2-adamantoxymethyloxy)-3,5-dimethylphenyl)diphenylsulfonium, (4-(2-adamantoxymethyloxy)phenyl)diphenylsulfonium, (4-(tert-butoxycarbonylmethytoxy)phenyl)diphenylsulfonium, (4-(tert-butoxycarbonylmethyloxy)-3,5-dimethylphenyl)diphenylsulfonium, (4-(2-methyl-2-adamantyloxycarbonylmethyloxy)phenyl)diphenylsulfonium, (4-(2-methyl-2-adamantyloxycarbonylmethyloxy)-3,5-dimethylphenyl)diphenylsulfonium, tri(4-methylphenyl)sulfonium, dimethyl(4-hydroxynaphthyl)sulfonium, monophenyldimethylsulfonium, diphenylmonomethylsulfonium, (4-methylphenyl)diphenylsulfonium, (4-methoxyphenyl)diphenylsulfonium, tri(4-tert-butyl)phenylsulfonium, diphenyl(1-(4-methoxy)naphthyl)sulfonium, di(1-naphthyl)phenylsulfonium, 1-phenyltetrahydrothiophenium, 1-(4-methylphenyl)tetrahydrothiophenium, 1-(3,5-dimethyl-4-hydroxyphenyl)tetrahydrothiophenium, 1-(4-methoxynaphthalene-1-yl)tetrahydrothiophenium, 1-(4-ethoxynaphthalene-1-yl)tetrahydrothiopheniumn, 1(4-n-butoxynaphthalene-1-yl)tetrahydrothiophenium, 1-phenyltetrahydrothiopyranium, 1-(4-hydroxyphenyl)tetrahydrothiopyranium, 1-(3,5-dimethyl-4-hydroxyphenyl)tetahydrothiopyranium and 1-(4-methylphenyl)tetrahydrothiopyranium.

In formula (b'-2), $R^{5\prime\prime\prime}$ and $R^{6\prime\prime\prime}$ each independently represents an aryl group or alkyl group. At least one of $R^{5\prime\prime\prime}$ and $R^{6\prime\prime\prime}$ represents an aryl group. It is preferable that both of $R^{5\prime\prime\prime}$ and $R^{6\prime\prime\prime}$ represent an aryl group.

As the aryl group for $R^{5\prime\prime\prime}$ and $R^{6\prime\prime\prime}$, the same as the aryl groups for $R^{1\prime\prime\prime}$ to $R^{3\prime\prime\prime}$ can be exemplified.

As the alkyl group for $R^{5\prime\prime\prime}$ and $R^{6\prime\prime\prime}$, the same as the alkyl groups for $R^{1\prime\prime\prime}$ to $R^{3\prime\prime\prime}$, can be exemplified.

It is particularly desirable that both of $R^{5\prime\prime\prime}$ and $R^{6\prime\prime\prime}$ represents a phenyl group.

Specific examples of cation moiety represented by general formula (b'-2) include diphenyliodonium and bis(4-tert-butylphenyl)iodonium.

In general formulas (b-5) and (b-6), with respect to $R^{40}$ to $R^{46}$, the alkyl group is preferably an alkyl group of 1 to 5 carbon atoms, more preferably a linear or branched alkyl group, and most preferably a methyl group, ethyl group, propyl group, isopropyl group, n-butyl group or tert butyl group.

The alkoxy group is preferably an alkoxy group of 1 to 5 carbon atoms, more preferably a linear or branched alkoxy group, and most preferably a methoxy group or ethoxy group.

The hydroxyalkyl group is preferably the aforementioned alkyl group in which one or more hydrogen atoms have been substituted with hydroxy groups, and examples thereof include a hydroxymethyl group, hydroxyethyl group and hydroxypropyl group.

If there are two or more of the $OR^{40}$ group, as indicated by the value of $n_0$, then the two or more of the $OR^{40}$ group may be the same or different from each other.

If there are two or more of an individual $R^{41}$ to $R^{46}$ group, as indicated by the corresponding value of $n_1$ to $n_6$, then the two or more of the individual $R^{41}$ to $R^{46}$ group may be the same or different from each other.

$n_0$ is preferably 0 or 1.

$n_1$ is preferably 0 to 2.

It is preferable that each of $n_2$ and $n_3$ independently represent 0 or 1, and more preferably 0.

$n_4$ is preferably 0 to 2, and more preferably 0 or 1.

$n_5$ is preferably 0 or 1, and more preferably 0.

$n_6$ is preferably 0 or 1.

In the present invention, as $Z^+$ a cation moiety represented by general formula (b'-1) or (b-5) is preferable. Especially, a cation moiety represented by any one of formulas (b'-1-1) to (b'-1-10) and (b-5-1) to (b-5-4) shown below is preferable, and a cation moiety having a triphenyl skeleton such as a cation moiety represented by any one of formulas (b'-1-1) to (b'-1-8) shown below, or a cation moiety represented by formula (b'-1-10) is more preferable.

In formulas (b'-1-9) and (b'-1-10), each of $R^8$ and $R^9$ independently represents a phenyl group, naphthyl group or alkyl group of 1 to 5 carbon atoms which may have a substituent, an alkoxy group or a hydroxy group, and a phenyl group which may have a substituent is preferable.

u is an integer of 1 to 3, and most preferably 1 or 2.

[Chemical Formula 26]

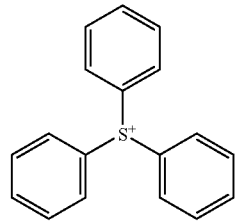

(b'-1-1)

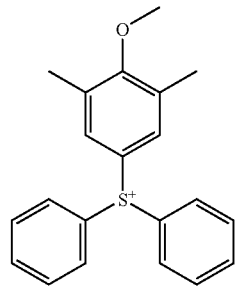

(b'-1-2)

(b'-1-3)
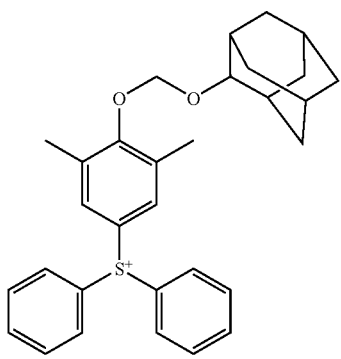
(b'-1-4)
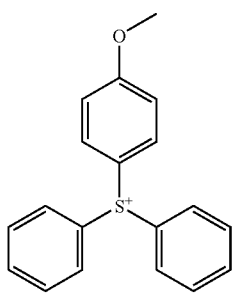
(b'-1-5)
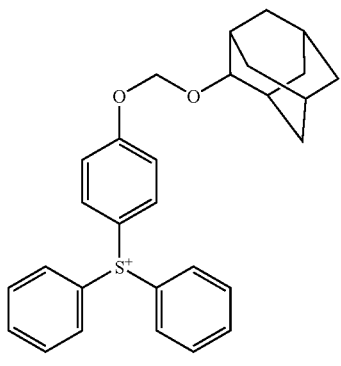
(b'-1-6)
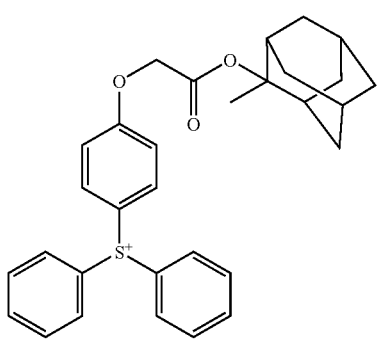
(b'-1-7)
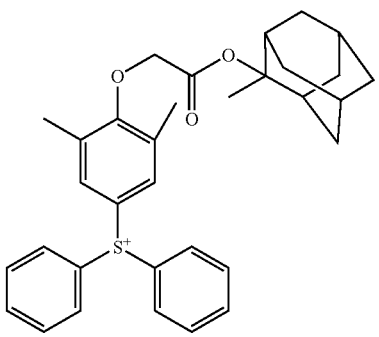
(b'-1-8)
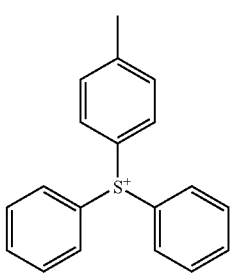
(b'-1-9)
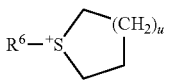
(b'-1-10)
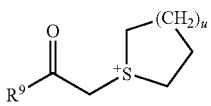
[Chemical Formula 27]
(b-5-1)
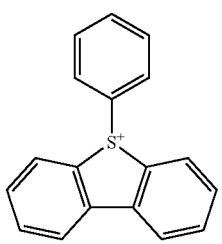
(b-5-2)
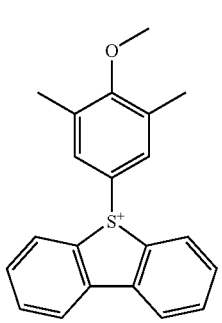

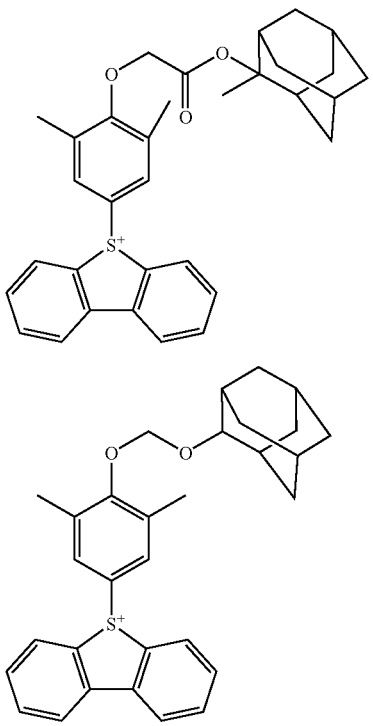

(b-5-3)

(b-5-4)

As the compound (b1-1), a compound represented by general formula (b1-1-1) is preferable.

[Chemical Formula 28]

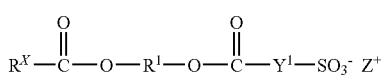

(b1-1-1)

wherein $R^X$, $Y^1$ and $Z^+$ are respectively as defined for $R^X$, $Y^1$ and $Z^+$ in general formula (b1-1) above; and $R^1$ represents an alkylene group.

In general formula (b1-1-1) above, $R^X$, $Y^1$ and $Z^+$ are respectively as defined for $R^X$, $Y^1$ and $Z^+$ in general formula (b1-1) above.

The alkylene group for $R^1$ may be any of a linear alkylene group, a branched alkylene group and a cyclic alkylene group, preferably a linear or branched alkylene group, and more preferably a linear alkylene group.

The linear or branched alkylene group preferably has 1 to 12 carbon atoms, more preferably 1 to 5, and still more preferably 1 to 3. Specific examples of the alkylene group include a methylene group [—$CH_2$—]; alkylmethylene groups such as —CH($CH_3$)—, —CH($CH_2CH_3$)—, —C($CH_3$)$_2$—, —C($CH_3$)($CH_2CH_3$)—, —C($CH_3$)($CH_2CH_2CH_3$)— and —C($CH_2CH_3$)$_2$; an ethylene group [—$CH_2CH_2$—]; alkylethylene groups such as —CH($CH_3$)$CH_2$)—, —CH($CH_3$)CH($CH_3$)—, —C($CH_3$)$_2CH_2$— and —CH($CH_2CH_3$)$CH_2$—; a trimethylene group (n-propylene group) [—$CH_2CH_2CH_2$—]; alkyltrimethylene groups such as —CH($CH_3$)$CH_2CH_2$— and —$CH_2$CH($CH_3$)$CH_2$—; a tetramethylene group [—$CH_2CH_2CH_2CH_2$—]; alkyltetramethylene groups such as —CH($CH_3$)$CH_2CH_2CH_2$— and —$CH_2$CH($CH_3$)$CH_2CH_2$—; and a pentamethylene group [—$CH_2CH_2CH_2CH_2CH_2$—]. Among these, a methylene group, an ethylene group or an n-propylene group is preferable, and an ethylene group is particularly desirable.

As the compound (b1-1), a compound represented by any one of general formulas (b1-1-11) to (b1-1-13) shown below are particularly desirable.

[Chemical Formula 29]

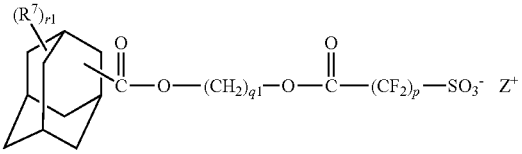

(b1-1-11)

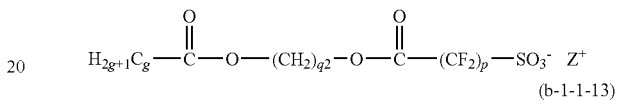

(b-1-1-12)

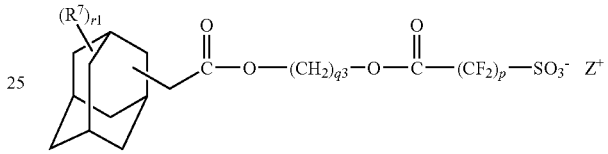

(b-1-1-13)

wherein $Z^+$ is as defined above; p represents an integer of 1 to 3; each of q1 to q3 independently represents an integer of 1 to 12; r1 represents an integer of 0 to 3; g represents an integer of 1 to 20; and $R^7$ represents a substituent.

As the substituent for $R^7$, the same groups as those which the aliphatic hydrocarbon group for $R^x$ may have as a substituent can be mentioned.

When there are two or more of the $R^7$ group, as indicated by the value of r1, then the two or more of $R^7$ may be the same or different from each other.

p is preferably 1 or 2.

It is preferable that each of q1 to q3 independently represent an integer of 1 to 5, and more preferably 1 to 3.

r1 preferably represents an integer of 0 to 2, and more preferably 0 or 1.

g preferably represents an integer of 1 to 15, and more preferably 1 to 10.

The compound (b1-1) of the present invention is a novel compound.

The compound (b1-1) of the present invention is useful as an acid generator for a chemically amplified resist composition, and the compound (b1-1) can be blended within a chemically amplified resist composition as an acid generator.

The method of producing the compound (b1-1) is not particularly limited. For example, the compound (b1-1) can be produced by the production method of compound (b1-1) according to the present invention described below.

<<Production Method of Compound (b1-1)>>

Next, the production method of compound (b1-1) according to the fourth aspect of the present invention will be described.

The production method of compound (b1-1) according to the fourth aspect of the present invention includes reacting a compound (b0-1) represented by general formula (b0-1) shown below with a compound (b0-02) represented by general formula (b0-02) shown below.

[Chemical Formula 30]

$$R^X-Q^3-O-Q^2-Y^1-SO_3^-{}^+W^+ \quad (b0\text{-}1)$$

$$Z^+A^- \quad (b0\text{-}02)$$

$$R^X-Q^3-O-Q^2-Y^1-SO_3^-Z^+ \quad (b1\text{-}1)$$

wherein $R^X$ represents a hydrocarbon group which may have a substituent exclusive of a nitrogen atom; each of $Q^2$ and $Q^3$ independently represents a single bond or a divalent linkage group; $Y^1$ represents an alkylene group or fluorinated alkyl group of 1 to 4 carbon atoms; $W^+$ represents an alkali metal ion or an ion represented by general formula (w-1) shown below; $Z^+$ represents an organic cation exclusive of an ion represented by general formula (w-1) shown below; and $A^-$ represents a non-nucleophilic ion.

[Chemical Formula 31]

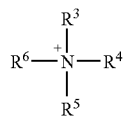

(w-1)

wherein each of $R^3$ to $R^6$ independently represents a hydrogen atom or a hydrocarbon group which may have a substituent, with the proviso that at least one of $R^3$ to $R^6$ represents a hydrocarbon group; and at least two of $R^3$ to $R^6$ may be mutually bonded to form a ring.

In the formulas above, $R^x$, $Q^2$, $Q^3$, $Y^1$ and $Z^+$ are respectively as defined for $R^x$, $Q^2$, $Q^3$, $Y^1$ and $Z^+$ in general formula (b1-1).

$W^+$ represents an alkali metal ion or an ion represented by general formula (w-1) above (hereafter, referred to as "substituted ammonium ion").

As the alkali metal ion for $W^+$, a sodium ion, a potassium ion, a lithium ion and the like can be mentioned.

In general formula (w-1), $R^3$ to $R^6$ are respectively as defined for $R^3$ to $R^6$ in general formula (b0-1) above.

$A^-$ represents a non-nucleophilic ion.

Examples of non-nucleophilic ions include a halogen ion such as a bromine ion or a chlorine ion, an ion which is capable of forming an acid exhibiting a lower acidity than the compound (b0-1), $BF_4^-$, $AsF_6^-$, $SbF_6^-$, $PF_6^-$ and $ClO_4^-$.

As the ion for $A^{--}$ which is capable of forming an acid exhibiting a lower acidity than the compound (b0-1), a sulfonic acid ion such as a p-toluenesulfonic acid ion, a methanesulfonic acid ion, a benzenesulfonic acid ion, or a trifluoromethanesulfonic acid ion can be mentioned.

In the production method of compound (b1-1) according to the fourth aspect of the present invention, it is particularly desirable that the compound (b0-1) be a compound (b0-01) represented by general formula (b0-01) shown below, and the compound (b1-1) be a compound (b1-1-1) represented by general formula (b1-1-1) shown below.

[Chemical Formula 32]

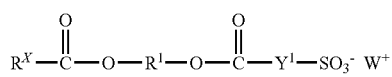

(b0-01)

-continued

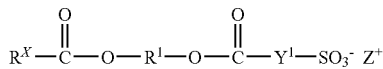

(b1-1-1)

wherein $R^x$, $Y^1$ and $W^+$ are respectively as defined for $R^x$, $Y^1$ and $W^+$ in general formula (b0-1) above; $Z^+$ is as defined for $Z^+$ in general formula (b1-1) above; and $R^1$ is as defined for $R^1$ in general formula (b0-1-11) above.

The aforementioned compound (b0-01) can be synthesized, for example, by reacting a compound (1-3) represented by general formula (1-3) shown below with a compound (2-1) represented by general formula (2-1) shown below.

[Chemical Formula 33]

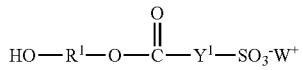

(1-3)

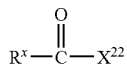

(2-1)

wherein $R^x$, $R^1$, $Y^1$ and $W^+$ are as defined above; and $X^{22}$ represents a halogen atom.

As the halogen atom for $X^{22}$, a bromine atom, a chlorine atom, an iodine atom and a fluorine atom can be mentioned. In terms of reactivity, a bromine atom or a chlorine atom is preferable, and a chlorine atom is particularly desirable.

As the compounds (1-3) and (2-1), commercially available compounds may be used, or the compounds may be synthesized.

For example, when $W^+$ in the compound (1-3) is an alkali metal ion, a preferable method of synthesizing such a compound (compound (1-3')) represented by general formula (1-3') shown below) includes reacting a compound (1-1) represented by general formula (1-1) shown below with a compound (1-2) represented by general formula (1-2) shown below, thereby obtaining a compound (1-3').

[Chemical Formula 34]

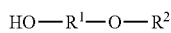

(1-1)

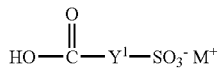

(1-2)

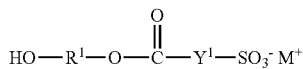

(1-3')

wherein $R^1$ and $Y^1$ are as defined above; $R^2$ represents an aliphatic group which may have an aromatic group as a substituent; and $M^+$ represents an alkali metal ion.

As $M^+$, the same alkali metal ions as those for $W^+$ above can be mentioned.

$R^2$ represents an aliphatic group which may have an aromatic group as a substituent.

The aliphatic group may be either a saturated aliphatic group, or an unsaturated aliphatic group. Further, the aliphatic group may be linear, branched or cyclic, or a combination thereof.

The aliphatic group may be either an aliphatic hydrocarbon group consisting of carbon atoms and hydrogen atoms, a group in which a part of the carbon atoms constituting the aforementioned aliphatic hydrocarbon group have been substituted with a hetero atom-containing substituent, or a group in which a part or all of the hydrogen atoms constituting the aforementioned aliphatic hydrocarbon group have been substituted with a hetero atom-containing substituent.

As the hetero atom, there is no particular limitation as long as it is an atom other than a carbon atom and a hydrogen atom. Examples of hetero atoms include a halogen atom, an oxygen atom, a sulfur atom and a nitrogen atom. Examples of halogen atoms include a fluorine atom, a chlorine atom, an iodine atom and a bromine atom.

The hetero atom-containing substituent may consist of a hetero atom, or may be a group containing a group or atom other than a hetero atom.

Specific examples of the substituent group for substituting a part of the carbon atoms include —O—, —C(=O)—O—, —C(=O)—, —O—C(=O)—O—, —C(=O)—NH—, —NH— (wherein H may be substituted with a substituent such as an alkyl group or an acyl group), —S—, —S(=O)$_2$— and —S(=O)$_2$—O—. When the aliphatic hydrocarbon group contains a cyclic group, the aliphatic hydrocarbon group may contain these substituent groups in the ring structure of the cyclic group.

Examples of the substituent group for substituting a part or all of the hydrogen atoms include an alkoxy group, a halogen atom, a halogenated alkyl group, a hydroxyl group, an oxygen atom (=O), —COOR$^{96}$, —OC(=O)R$^{97}$ and a cyano group.

The aforementioned alkoxy group is preferably an alkoxy group having 1 to 5 carbon atoms, more preferably a methoxy group, ethoxy group, n-propoxy group, iso-propoxy group, n-butoxy group or tert-butoxy group, and most preferably a methoxy group or an ethoxy group.

Examples of the aforementioned halogen atom include a fluorine atom, a chlorine atom, a bromine atom and an iodine atom, and a fluorine atom is preferable.

Example of the aforementioned halogenated alkyl group includes a group in which a part or all of the hydrogen atoms within an alkyl group of 1 to 5 carbon atoms (e.g., a methyl group, an ethyl group, a propyl group, an n-butyl group or a tert-butyl group) have been substituted with the aforementioned halogen atoms.

Each of R$^{96}$ and R$^{97}$ independently represents a hydrogen atom or a linear, branched or cyclic alkyl group of 1 to 15 carbon atoms.

When the alkyl group for R$^{96}$ and R$^{97}$ is a linear or branched alkyl group, it preferably has 1 to 10 carbon atoms, more preferably 1 to 5, and still more preferably 1 or 2. Specific examples of alkyl groups include the same groups as those for the linear or branched monovalent saturated hydrocarbon group described below.

When the alkyl group for R$^{96}$ and R$^{97}$ is a cyclic group, it may be either a monocyclic group or a polycyclic group. The cyclic group preferably has 3 to 15 carbon atoms, more preferably 4 to 12, and still more preferably 5 to 10. Specific examples of cyclic groups include the same groups as those for the cyclic monovalent saturated hydrocarbon group described below.

As the aliphatic hydrocarbon group, a linear or branched saturated hydrocarbon group of 1 to 30 carbon atoms, a linear or branched unsaturated hydrocarbon group of 2 to 10 carbon atoms, or an aliphatic cyclic group (alicyclic group) of 3 to 30 carbon atoms is preferable.

The linear saturated hydrocarbon group preferably has 1 to 20 carbon atoms, more preferably 1 to 15, and most preferably 1 to 10. Specific examples include a methyl group, an ethyl group, a propyl group, a butyl group, a pentyl group, a hexyl group, a heptyl group, an octyl group, a nonyl group, a decanyl group, an undecyl group, a dodecyl group, a tridecyl group, an isotridecyl group, a tetradecyl group, a pentadecyl group, a hexadecyl group, an isohexadecyl group, a heptadecyl group, an octadecyl group, a nonadecyl group, an icosyl group, a henicosyl group and a docosyl group.

The branched saturated hydrocarbon group preferably has 3 to 20 carbon atoms, more preferably 3 to 15, and most preferably 3 to 10. Specific examples include a 1-methylethyl group, a 1-methylpropyl group, a 2-methylpropyl group, a 1-methylbutyl group, a 2-methylbutyl group, a 3-methylbutyl group, a 1-ethylbutyl group, a 2-ethylbutyl group, a 1-methylpentyl group, a 2-methylpentyl group, a 3-methylpentyl group and a 4-methylpentyl group.

The unsaturated hydrocarbon group preferably has 2 to 5 carbon atoms, more preferably 2 to 4, and most preferably 3. Examples of linear monovalent unsaturated hydrocarbon groups include a vinyl group, a propenyl group (an allyl group) and a butynyl group. Examples of branched monovalent unsaturated hydrocarbon groups include a 1-methylpropenyl group and a 2-methylpropenyl group.

Among the above-mentioned examples, as the unsaturated hydrocarbon group, a propenyl group is particularly desirable.

The aliphatic cyclic group may be either a monocyclic group or a polycyclic group. The aliphatic cyclic group preferably has 3 to 30 carbon atoms, more preferably 5 to 30, still more preferably 5 to 20, still more preferably 6 to 15, and most preferably 6 to 12. As the aliphatic cyclic group, a group in which one or more hydrogen atoms have been removed from a monocycloalkane or a polycycloalkane such as a bicycloalkane, tricycloalkane or tetracycloalkane can be mentioned. Specific examples include groups in which one or more hydrogen atoms have been removed from a monocycloalkane such as cyclopentane or cyclohexane; and groups in which one or more hydrogen atoms have been removed from a polycycloalkane such as adamantane, norbornane, isobornane, tricyclodecane or tetracyclododecane.

The aliphatic group for R$^2$ may have an aromatic group as a substituent.

Examples of aromatic groups include an aryl group which is an aromatic hydrocarbon ring having one hydrogen atom removed therefrom, such as a phenyl group, a biphenyl group, a fluorenyl group, a naphthyl group, an anthryl group or a phenanthryl group; and a heteroaryl group in which a part of the carbon atoms constituting the aforementioned aryl group has been substituted with a hetero atom such as an oxygen atom, a sulfur atom or a nitrogen atom.

The aromatic group may have a substituent such as an alkyl group of 1 to 10 carbon atoms, a halogenated alkyl group, an alkoxy group, a hydroxyl group or a halogen atom. The alkyl group or halogenated alkyl group as a substituent preferably has 1 to 8 carbon atoms, and more preferably 1 to 4 carbon atoms. Further, the halogenated alkyl group is preferably a fluorinated alkyl group. Examples halogen atoms include a fluorine atom, a chlorine atom, an iodine atom and a bromine atom, and a fluorine atom is preferable.

When the R$^2$ group in the compound (1-1) represents an aromatic group, i.e., when the oxygen atom adjacent to the R$^2$ group is directly bonded to an aromatic ring without an aliphatic group, the reaction between the compound (1-1) and the compound (1-2) does not proceed, such that the compound (1-3) cannot be obtained.

As the compounds (1-1) and (1-2), commercially available compounds may be used, or the compounds may be synthesized by a conventional method.

For example, a method including heating a compound (0-1) represented by general formula (0-1) shown below in the presence of an alkali, and neutralizing the resultant, thereby obtaining a compound (0-2) represented by general formula (0-2) shown below (hereafter, this step is referred to as "salt-formation step"); and heating the compound (0-2) in the presence of acid having an acid strength stronger than that of the compound (1-2), thereby obtaining the compound (1-2) (hereafter, this step is referred to as "carboxylic acid-generation step") can be mentioned.

[Chemical Formula 35]

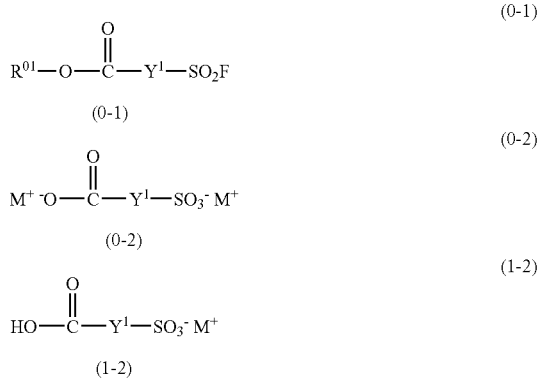

wherein $R^{01}$ represents an alkyl group; and $Y^1$ and $M^+$ are as defined above.

As the alkyl group for $R^{01}$, a linear or branched alkyl group is preferable, and specific examples include a methyl group, an ethyl group, a propyl group, an isopropyl group, an n-butyl group, an isobutyl group, a tert-butyl group, a pentyl group, an isopentyl group and a neopentyl group. Among these, an alkyl group of 1 to 4 carbon atoms is preferable, and a methyl group is particularly desirable.

As the compound (0-1), a commercially available compound can be used.

The salt-formation step can be performed, for example, by dissolving the compound (0-1) in a solvent, and adding an alkali to the resulting solution, followed by heating.

As the solvent, any solvent which is capable of dissolving the compound (0-1) can be used. Examples of such a solvent include water and tetrahydrofuran.

As the alkali, an alkali corresponding to M in formula (0-2) is used. Examples of such an alkali include alkali metal hydroxides such as sodium hydroxide, potassium hydroxide and lithium hydroxide.

The amount of the alkali is preferably 1 to 5 moles, more preferably 2 to 4 moles, per 1 mole of the compound (0-1).

The heating temperature is preferably 20 to 120° C., and more preferably 50 to 100° C. The heating time depends on the heating temperature and the like, but in general, the heating time is preferably 0.5 to 12 hours, and more preferably 1 to 5 hours.

The neutralization following the heating can be conducted by adding an acid such as hydrochloric acid, sulfuric acid, p-toluenesulfonic acid, or the like to the reaction liquid following the heating.

It is preferable to conduct the neutralization so that the pH of the reaction liquid (25° C.) after addition of an acid falls within the range of 6 to 8. Further, the temperature of the reaction liquid during the neutralization is preferably 20 to 30° C., and more preferably 23 to 27° C.

After the reaction, the compound (0-2) within the reaction liquid may be separated and purified. The separation and purification can be conducted by a conventional method. For example, any one of concentration, solvent extraction, distillation, crystallization, recrystallization and chromatography can be used alone, or two or more of these methods may be used in combination.

In the carboxylic acid-generation step, the compound (0-2) obtained in the salt-formation step is heated in the presence of acid having an acid strength stronger than that of the compound (1-2), thereby obtaining the compound (1-2).

"An acid having an acid strength stronger than that of the compound (1-2)" (hereafter, frequently referred to simply as "strong acid") refers to an acid having a pKa value (25° C.) smaller than that of —COOH within the compound (1-2). By using such a strong acid, —COO⁻M⁺ within the compound (0-2) can be converted into —COOH, thereby obtaining the compound (1-2).

The strong acid can be appropriately selected from any conventional acids which exhibit a pKa value smaller than that of —COOH within the compound (1-2). The pKa value of —COOH within the compound (1-2) can be determined by a conventional titration method.

Specific examples of strong acids include a sulfonic acid, such as an arylsulfonic acid or an alkylsulfonic acid; sulfuric acid; and hydrochloric acid. An example of an arylsulfonic acid includes p-toluenesulfonic acid. Examples of alkylsulfonic acids include methanesulfonic acid and trifluoromethane sulfonic acid. In consideration of solubility in an organic solvent and ease in purification, p-toluenesulfonic acid is particularly desirable as the strong acid.

The carboxylic acid-generation step can be performed, for example, by dissolving the compound (0-2) in a solvent, and adding a strong acid to the resulting solution, followed by heating.

As the solvent, any solvent which is capable of dissolving the compound (0-2) can be used. Examples of such solvents include acetonitrile and methyl ethyl ketone.

The amount of the strong acid is preferably 0.5 to 3 moles, and more preferably 1 to 2 moles, per 1 mole of the compound (0-2).

The heating temperature is preferably 20 to 150° C., and more preferably 50 to 120° C. The heating time depends on the heating temperature and the like, but in general, the heating time is preferably 0.5 to 12 hours, and more preferably 1 to 5 hours.

After the reaction, the compound (1-2) within the reaction liquid may be separated and purified. The separation and purification can be conducted by a conventional method. For example, any one of concentration, solvent extraction, distillation, crystallization, recrystallization and chromatography can be used alone, or two or more of these methods may be used in combination.

Alternatively, when $W^+$ in the compound (1-3) represents the aforementioned substituted ammonium ion, such a compound (a compound (1-3")) represented by general formula (1-3") shown below) can be produced by reacting the aforementioned compound (1-3') with an ammonium salt.

[Chemical Formula 36]

$$HO-R^1-O-\overset{O}{\overset{\|}{C}}-Y^1-SO_3^-  \quad R^6-\overset{R^3}{\overset{+}{\underset{R^5}{N}}}-R^4 \qquad (1\text{-}3'')$$

wherein $R^x$, $R^1$, $Y^1$ and $R^3$ to $R^6$ are as defined above.

Examples of ammonium salts include the aforementioned alkylamines, dialkylamines, trialkylamines, and a hydrochloride or bromate of an aromatic amine.

The reaction between a compound (1-3') and an ammonium salt can be conducted, for example, by dissolving a compound (1-3') and an ammonium salt in a solvent such as water, dichloromethane, acetonitrile, methanol or chlororform, followed by stirring or the like.

The reaction temperature is preferably 0 to 150° C., and more preferably 0 to 100° C. The reaction time depends on the reactivity of the compound (1-3') and the ammonium salt, reaction temperature, or the like, but in general, the reaction time is preferably 0.5 to 10 hours, more preferably 1 to 5 hours.

The method of reacting the compound (1-3) with the compound (2-1) is not particularly limited, and can be performed, for example, by contacting the compound (1-3) with the compound (2-1) in a reaction solvent. Such a method can be performed, for example, by adding the compound (2-1) to a solution obtained by dissolving the compound (1-3) in a reaction solvent, in the presence of a base.

As the reaction solvent, any solvent which is capable of dissolving the compound (1-3) and the compound (2-1) as the raw materials can be used. Specific examples of such solvents include tetrahydrofuran (THF), acetone, dimethylformamide (DMF), dimethylacetamide, dimethylsulfoxide (DMSO) and acetonitrile.

Examples of bases include an organic base such as triethylamine, 4-dimethylaminopyridine (DMAP) and pyridine, and an inorganic base such as $K_2CO_3$ and $Cs_2CO_3$.

The amount of the compound (2-1) is preferably 1 to 3 equivalents, and more preferably 1 to 2 equivalents, based on the amount of the compound (1-3).

The reaction temperature is preferably −20 to 40° C., and more preferably 0 to 30° C. The reaction time depends on the reactivity of the compound (1-3) and the compound (2-1), the reaction temperature, and the like, but in general, the reaction temperature is preferably 1 to 120 hours, and more preferably 1 to 48 hours.

Furthermore, when $W^+$ in the compound (b0-01) represents the aforementioned substituted ammonium ions such a compound (a compound (b0-01')) represented by general formula (b0-01')) can be produced by a method including simultaneously reacting the compound (1-3'), the compound (2-1) and an amine or an ammonium salt.

[Chemical Formula 37]

$$HO-R^1-O-\overset{O}{\overset{\|}{C}}-Y^1-SO_3^- M^+ \qquad (1\text{-}3')$$

$$R^X-\overset{O}{\overset{\|}{C}}-X^{22} \qquad (2\text{-}1)$$

-continued $$R^X-\overset{O}{\overset{\|}{C}}-O-R^1-O-\overset{O}{\overset{\|}{C}}-Y^1-SO_3^- \quad R^6-\overset{R^3}{\overset{+}{\underset{R^5}{N}}}-R^4 \qquad (b0\text{-}01')$$

wherein $R^x$, $R^1$, $Y^1$, $W^+$ and $X^{22}$ are as defined above.

The compound (1-3'), the compound (2-1) and the amine or ammonium salt can be reacted in the same manner as in the reaction between the compound (1-3) and the compound (2-1).

Examples of amines include the aforementioned alkylamines, dialkylamines, trialkylamines, and aromatic amines. Examples of ammonium salts include tetraalkylammonium hydroxides (wherein the alkyl group within the tetraalkylammonium independently represents an alkyl group of 1 to 4 carbon atoms) such as tetramethylammonium hydroxide, tetraethylammonium hydroxide and tetrabutylammonium hydroxide.

In the aforementioned production method, the substituted ammonium salt such as the aforementioned compound (1-3") or the aforementioned compound (b0-01') is useful as an intermediate in the production of the compound (b1-1) of the present invention. As the substituted ammonium salt has $N^+(R^3)(R^4)(R^5)(R^6)$ as the cation moiety, the compound (b0-1) can be easily purified by washing with water, and hence, improvement in the purity of the final product can be expected. For example, with respect to a compound in which the cation moiety is an alkali metal ion, purification by washing with water is difficult because the compound gets dissolved in water.

Therefore, in the production method of the present invention, it is preferable that the compound (b1-1) be produced from an intermediate having the aforementioned substituted ammonium ion as the cation moiety.

The reaction between the compound (b0-01) and the compound (b0-02) can be conducted, for example, by dissolving the compound (b0-01) and the compound (b0-02) in a solvent such as water, dichloromethane, acetonitrile, methanol or chlororform, followed by stirring or the like.

The reaction temperature is preferably 0 to 150° C., and more preferably 0 to 100° C. The reaction time depends on the reactivity of the compound (b0-01) and the compound (b0-02), the reaction temperature, or the like, but in general, the reaction time is preferably 0.5 to 10 hours, more preferably 1 to 5 hours.

After the reaction, the compound (b1-1) within the reaction liquid may be separated and purified. The separation and purification can be conducted by a conventional method. For example, any one of concentration, solvent extraction, distillation, crystallization, recrystallization and chromatography can be used alone, or two or more of these methods may be used in combination.

The structure of the compound (b1-1) obtained in the above-described manner can be confirmed by a general organic analysis method such as $^1$H-nuclear magnetic resonance (NMR) spectrometry, $^{13}$C-NMR spectrometry, $^{19}$F-NMR spectrometry, infrared absorption (IR) spectrometry, mass spectrometry (MS), elementary analysis and X-ray diffraction analysis.

<<Acid Generator>>

The acid generator according to the fifth aspect of the present invention consists of the aforementioned compound (b1-1) of the present invention.

The acid generator is useful as an acid generator for a chemically amplified resist composition, for example, an acid-generator component (B) for the resist composition according to the first aspect of the present invention described below.

It is particularly desirable that the acid generator consist of a compound represented by general formula (b1-1-1) above.

<<Resist Composition>>

Next, the resist composition according to the first aspect of the present invention will be described.

The resist composition according to the first aspect of the present invention includes a base component (A) (hereafter, referred to as "component (A)") which exhibits changed solubility in an alkali developing solution under action of acid and an acid-generator component (B) (hereafter, referred to as "component (B)") which generates acid upon exposure.

With respect to a resist film formed using the resist composition, when a selective exposure is conducted during formation of a resist pattern, acid is generated from the component (B), and the generated acid acts on the component (A) to change the solubility of the component (A) in an alkali developing solution. As a result, the solubility of the exposed portions in an alkali developing solution is changed, whereas the solubility of the unexposed portions in an alkali developing solution remains unchanged. Therefore, the exposed portions are dissolved and removed by alkali developing in the case of a positive resist composition, whereas unexposed portions are dissolved and removed in the case of a negative resist composition, and hence, a resist pattern can be formed.

The resist composition of the present invention may be either a negative resist composition or a positive resist composition.

<Component (A)>

As the component (A), an organic compound typically used as a base component for a chemically amplified resist composition can be used alone, or two or more of such organic compounds can be mixed together.

Here, the term "base component" refers to an organic compound capable of forming a film, and is preferably an organic compound having a molecular weight of 500 or more. When the organic compound has a molecular weight of 500 or more, the film-forming ability is improved, and a resist pattern of nano level can be easily formed.

The organic compounds having a molecular weight of 500 or more are broadly classified into low molecular weight organic compounds having a molecular weight of 500 to less than 2,000 (hereafter, frequently referred to as "low molecular weight compounds") and high molecular weight resins (polymeric materials) having a molecular weight of 2,000 or more. Generally, as the aforementioned low molecular weight compound, a non-polymer is used. With respect to the aforementioned resin (polymer or copolymer), the molecular weight is the polystyrene equivalent value determined by gel permeation chromatography (GPC). Hereafter, a "resin" refers to a resin having a molecular weight of 2,000 or more.

As the component (A), a resin which exhibits changed solubility in an alkali developing solution under action of acid may be used. Alternatively, as the component (A), a low molecular weight material which exhibits changed solubility in an alkali developing solution under action of acid may be used.

When the resist composition of the present invention is a negative resist composition, for example, as the component (A), a base component that is soluble in an alkali developing solution is used, and a cross-linking agent is blended in the negative resist composition.

In the negative resist composition, when acid is generated from the component (B) upon exposure, the action of the generated acid causes cross-linking between the base component and the cross-linking agent, and the cross-linked portion becomes insoluble in an alkali developing solution. Therefore, in the formation of a resist pattern, by conducting selective exposure of a resist film formed by applying the negative resist composition onto a substrate, the exposed portions become insoluble in an alkali developing solution, whereas the unexposed portions remain soluble in an alkali developing solution, and hence, a resist pattern can be formed by alkali developing.

Generally, as the component (A) for a negative resist composition, a resin that is soluble in an alkali developing solution (hereafter, referred to as "alkali-soluble resin") is used.

As the alkali-soluble resin, it is preferable to use a resin having a structural unit derived from at least one of α-(hydroxyalkyl)acrylic acid and a lower alkyl ester of α-(hydroxyalkyl)acrylic acid, as it enables formation of a satisfactory resist pattern with minimal swelling. Here, the term "α-(hydroxyalkyl) acrylic acid" refers to one or both of acrylic acid in which a hydrogen atom is bonded to the carbon atom on the α-position having the carboxyl group bonded thereto, and α-hydroxyalkylacrylic acid in which a hydroxyalkyl group (preferably a hydroxyalkyl group of 1 to 5 carbon atoms) is bonded to the carbon atom on the α-position.

As the cross-linking agent, typically, an amino-based cross-linking agent such as a glycoluril having a methylol group or alkoxymethyl group is preferable, as it enables formation of a resist pattern with minimal swelling. The amount of the cross-linking agent added is preferably within the range from 1 to 50 parts by weight, relative to 100 parts by weight of the alkali-soluble resin.

When the resist composition of the present invention is a positive resist composition, as the component (A), a base component which exhibits increased solubility in an alkali developing solution by action of acid is used. The component (A) is insoluble in an alkali developing solution prior to exposure, and when acid is generated from the component (B) upon exposure, the solubility of the component (A) in an alkali developing solution increases. Therefore, in the formation of a resist pattern, by conducting selective exposure of a resist film formed by applying the positive resist composition onto a substrate, the exposed portions changes from an insoluble state to a soluble state in an alkali developing solution, whereas the unexposed portions remain insoluble in an alkali developing solution, and hence, a resist pattern can be formed by alkali developing.

In the resist composition of the present invention the component (A) is preferably a base component which exhibits increased solubility in an alkali developing solution under action of acid. That is, the resist composition of the present invention is preferably a positive resist composition.

The component (A) may be a resin component (A1) which exhibits increased solubility in an alkali developing solution under action of acid (hereafter, referred to as "component (A1)"), a low molecular weight compound (A2) which exhibits increased solubility in an alkali developing solution under action of acid (hereafter, referred to as "component (A2)"), or a mixture of the component (A1) and the component (A2). It is preferable that the component (A) contain the component (A1).

[Component (A1)]

As the component (A1), a resin component (base resin) typically used as a base component for a chemically amplified resist composition can be used alone, or two or more of such resin components can be mixed together.

In the present invention, it is preferable that the component (A1) include a structural unit derived from an acrylate ester.

In the present descriptions and the claims, the term "structural unit derived from an acrylate ester" refers to a structural unit which is formed by the cleavage of the ethylenic double bond of an acrylate ester.

The term "acrylate ester" is a generic term that includes acrylate esters having a hydrogen atom bonded to the carbon atom on the α-position, and acrylate esters having a substituent (an atom other than a hydrogen atom or a group) bonded to the carbon atom on the α-position. As the substituent, a lower alkyl group or a halogenated lower alkyl group can be mentioned.

With respect to the "structural unit derived from an acrylate ester", the "α-position (the carbon atom on the α-position)" refers to the carbon atom having the carbonyl group bonded thereto, unless specified otherwise.

With respect to the acrylate ester, specific examples of the lower alkyl group for the substituent at the α-position include linear or branched alkyl groups such as a methyl group, ethyl group, propyl group, isopropyl group, n-butyl group, isobutyl group, tert-butyl group, pentyl group, isopentyl group, and neopentyl group.

Specific examples of the halogenated lower alkyl group include groups in which some or all of the hydrogen atoms of the aforementioned "lower alkyl group for the substituent at the α-position" are substituted with halogen atoms. Examples of halogen atoms include fluorine atoms, chlorine atoms, bromine atoms and iodine atoms, and fluorine atoms are particularly desirable.

In the present invention, it is preferable that a hydrogen atom, a lower alkyl group or a halogenated lower alkyl group is bonded to the α-position of the acrylate ester, more preferably a hydrogen atom, a lower alkyl group or a fluorinated lower alkyl group. In terms of industrial availability, a hydrogen atom or a methyl group is particularly desirable.

It is particularly desirable that the component (A1) have a structural unit (a1) derived from an acrylate ester containing an acid dissociable, dissolution inhibiting group.

Further, it is preferable that the component (A1) have a structural unit (a2) derived from an acrylate ester containing a lactone-containing cyclic group, as well as the structural unit (a1).

Furthermore, it is preferable that the component (A1) have a structural unit (a3) derived from an acrylate ester containing a polar group-containing aliphatic hydrocarbon group, as well as the structural unit (a1), or the structural unit (a1) and the structural unit (a2).

Structural Unit (a1)

As the acid dissociable, dissolution inhibiting group in the structural unit (a1), any of the groups that have been proposed as acid dissociable, dissolution inhibiting groups for the base resins of chemically amplified resists can be used, provided the group has an alkali dissolution-inhibiting effect that renders the entire component (A1) insoluble in an alkali developing solution prior to dissociation, and then following dissociation by action of acid, increases the solubility of the entire component (A1) in the alkali developing solution.

Generally, groups that form either a cyclic or chain-like tertiary alkyl ester with the carboxyl group of the (meth) acrylic acid, and acetal-type acid dissociable, dissolution inhibiting groups such as alkoxyalkyl groups are widely known.

Here, a tertiary alkyl ester describes a structure in which an ester is formed by substituting the hydrogen atom of a carboxyl group with a chain-like or cyclic tertiary alkyl group, and a tertiary carbon atom within the chain-like or cyclic tertiary alkyl group is bonded to the oxygen atom at the terminal of the carbonyloxy group (—C(O)—O—). In this tertiary alkyl ester, the action of acid causes cleavage of the bond between the oxygen atom and the tertiary carbon atom.

The chain-like or cyclic alkyl group may have a substituent.

Hereafter, for the sake of simplicity, groups that exhibit acid dissociability as a result of the formation of a tertiary alkyl ester with a carboxyl group are referred to as "tertiary alkyl ester-type acid dissociable, dissolution inhibiting groups".

Examples of tertiary alkyl ester-type acid dissociable, dissolution inhibiting groups include aliphatic branched, acid dissociable, dissolution inhibiting groups and aliphatic cyclic group-containing acid dissociable, dissolution inhibiting groups.

The term "aliphatic branched" refers to a branched structure having no aromaticity.

The "aliphatic branched, acid dissociable, dissolution inhibiting group" is not limited to be constituted of only carbon atoms and hydrogen atoms (not limited to hydrocarbon groups), but is preferably a hydrocarbon group.

Further, the "hydrocarbon group" may be either saturated or unsaturated, but is preferably saturated.

Examples of aliphatic branched, acid dissociable, dissolution inhibiting groups include tertiary alkyl groups of 4 to 8 carbon atoms, and specific examples include a tert-butyl group, tert-pentyl group and tert-heptyl group.

The term "aliphatic cyclic group" refers to a monocyclic group or polycyclic group that has no aromaticity.

The "aliphatic cyclic group" within the structural unit (a1) may or may not have a substituent. Examples of substituents include lower alkyl groups of 1 to 5 carbon atoms, fluorine atom, fluorinated lower alkyl groups of 1 to 5 carbon atoms, and oxygen atom (=O).

The basic ring of the "aliphatic cyclic group" exclusive of substituents is not limited to be constituted from only carbon and hydrogen (not limited to hydrocarbon groups), but is preferably a hydrocarbon group. Further, the "hydrocarbon group" may be either saturated or unsaturated, but is preferably saturated. Furthermore, the "aliphatic cyclic group" is preferably a polycyclic group.

As such aliphatic cyclic groups, groups in which one or more hydrogen atoms have been removed from a monocycloalkane or a polycycloalkane such as a bicycloalkane, tricycloalkane or tetracycloalkane which may or may not be substituted with a lower alkyl group, a fluorine atom or a fluorinated lower alkyl group, may be mentioned. Specific examples include groups in which one or more hydrogen atoms have been removed from a monocycloalkane such as cyclopentane and cyclohexane; and groups in which one or more hydrogen atoms have been removed from a polycycloalkane such as adamantane, norbornane, isobornane, tricyclodecane or tetracyclododecane.

As the aliphatic cyclic group-containing acid dissociable, dissolution inhibiting group, for example, a group which has a tertiary carbon atom on the ring structure of the cycloalkyl group can be mentioned. Specific examples include 2-methyl-2-adamantyl group and a 2-ethyl-2-adamantyl group. Further, groups having an aliphatic cyclic group such as an adamantyl group, cyclohexyl group, cyclopentyl group, norbornyl group, tricyclodecanyl group or tetracyclododecanyl group, and a branched alkylene group having a tertiary carbon atom bonded thereto, as the groups bonded to the oxygen atom of the carbonyl group (—C(O)—O—) within the structural units represented by general formulas (a1"-1) to (a1"-6) shown below, can be mentioned.

[Chemical Formula 38]

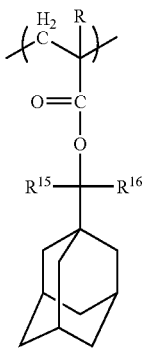
(a1″-1)

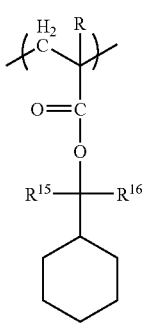
(a1″-2)

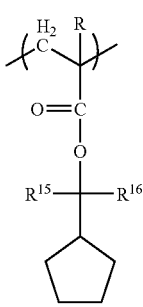
(a1″-3)

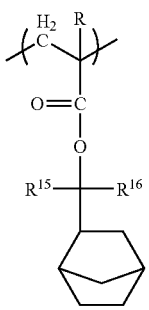
(a1″-4)

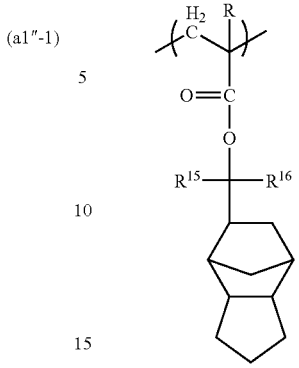
(a1″-5)

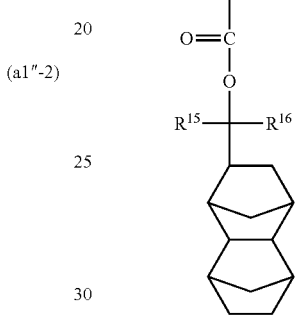
(a1″-6)

wherein R represents a hydrogen atom, a lower alkyl group or a halogenated lower alkyl group; and $R^{15}$ and $R^{16}$ each independently represents an alkyl group (which may be linear or branched, and preferably has 1 to 5 carbon atoms).

In general formulas (a1″-1) to (a1″-6) above, the lower alkyl group or halogenated lower alkyl group for R are the same as the lower alkyl group or halogenated lower alkyl group which can be bonded to the α-position of the aforementioned acrylate ester.

An "acetal-type acid dissociable, dissolution inhibiting group" generally substitutes a hydrogen atom at the terminal of an alkali-soluble group such as a carboxy group or hydroxyl group, so as to be bonded with an oxygen atom. When acid is generated upon exposure, the generated acid acts to break the bond between the acetal-type acid dissociable, dissolution inhibiting group and the oxygen atom to which the acetal-type, acid dissociable, dissolution inhibiting group is bonded.

Examples of acetal-type acid dissociable, dissolution inhibiting groups include groups represented by general formula (p1) shown below.

[Chemical Formula 39]

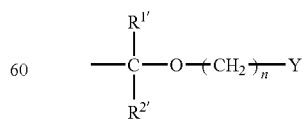
(p1)

wherein $R^{1\prime}$ and $R^{2\prime}$ each independently represents a hydrogen atom or a lower alkyl group; n represents an integer of 0 to 3; and Y represents a lower alkyl group or an aliphatic cyclic group.

In general formula (p1) above, n is preferably an integer of 0 to 2, more preferably 0 or 1, and most preferably 0.

As the lower alkyl group for $R^{1\prime}$ and $R^{2\prime}$, the same lower alkyl groups as those for R above can be mentioned. As the lower alkyl group for $R^{1\prime}$ and $R^{2\prime}$, a methyl group or ethyl group is preferable, and a methyl group is particularly desirable.

In the present invention, it is preferable that at least one of $R^{1\prime}$ and $R^{2\prime}$ be a hydrogen atom. That is, it is preferable that the acid dissociable, dissolution inhibiting group (p1) is a group represented by general formula (p1-1) shown below.

[Chemical Formula 40]

(p1-1)

wherein $R^{1\prime}$, n and Y are as defined above.

As the lower alkyl group for Y, the same lower alkyl groups as those for R above can be mentioned.

As the aliphatic cyclic group for Y, any of the aliphatic monocyclic/polycyclic groups which have been proposed for conventional ArF resists and the like can be appropriately selected for use. For example, the same groups described above in connection with the "aliphatic cyclic group" can be mentioned.

Further, as the acetal-type, acid dissociable, dissolution inhibiting group, groups represented by general formula (p2) shown below can also be mentioned.

[Chemical Formula 41]

(p2)

wherein $R^{17}$ and $R^{18}$ each independently represents a linear or branched alkyl group or a hydrogen atom; and $R^{19}$ represents a linear, branched or cyclic alkyl group; or $R^{17}$ and $R^{19}$ each independently represents a linear or branched alkylene group, wherein the terminal of $R^{17}$ is bonded to the terminal of $R^{19}$ to form a ring.

The alkyl group for $R^{17}$ and $R^{18}$ preferably has 1 to 15 carbon atoms, and may be either linear or branched. As the alkyl group, an ethyl group or a methyl group is preferable and a methyl group is most preferable.

It is particularly desirable that either one of $R^{17}$ and $R^{18}$ be a hydrogen atom, and the other be a methyl group.

$R^{19}$ represents a linear, branched or cyclic alkyl group which preferably has 1 to 15 carbon atoms, and may be any of linear, branched or cyclic.

When $R^{19}$ represents a linear or branched alkyl group, it is preferably an alkyl group of 1 to 5 carbon atoms, more preferably an ethyl group or methyl group, and most preferably an ethyl group.

When $R^{19}$ represents a cycloalkyl group, it preferably has 4 to 15 carbon atoms, more preferably 4 to 12 carbon atoms, and most preferably 5 to 10 carbon atoms. As examples of the cycloalkyl group, groups in which one or more hydrogen atoms have been removed from a monocycloalkane or a polycycloalkane such as a bicycloalkane, tricycloalkane or tetracycloalkane, which may or may not be substituted with a fluorine atom or a fluorinated alkyl group, may be mentioned. Specific examples include groups in which one or more hydrogen atoms have been removed from a monocycloalkane such as cyclopentane or cyclohexane, and groups in which one or more hydrogen atoms have been removed from a polycycloalkane such as adamantane, norbornane, isobornane, tricyclodecane or tetracyclododecane. Of these, a group in which one or more hydrogen atoms have been removed from adamantane is preferable.

In general formula (p2) above, $R^{17}$ and $R^{19}$ may each independently represent a linear or branched alkylene group (preferably an alkylene group of 1 to 5 carbon atoms), and the terminal of $R^{19}$ may be bonded to the terminal of $R^{17}$.

In such a case, a cyclic group is formed by $R^{17}$, $R^{19}$, the oxygen atom having $R^{19}$ bonded thereto and the carbon atom having the oxygen atom and $R^{17}$ bonded thereto. Such a cyclic group is preferably a 4 to 7-membered ring, and more preferably a 4 to 6-membered ring. Specific examples of the cyclic group include tetrahydropyranyl group and tetrahydrofuranyl group.

As the structural unit (a1), it is preferable to use at least one member selected from the group consisting of structural units represented by formula (a1-0-1) shown below and structural units represented by formula (a1-0-2) shown below.

[Chemical Formula 42]

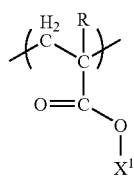

(a1-0-1)

wherein R represents a hydrogen atom, a lower alkyl group or a halogenated lower alkyl group; and $X^1$ represents an acid dissociable, dissolution inhibiting group.

[Chemical Formula 43]

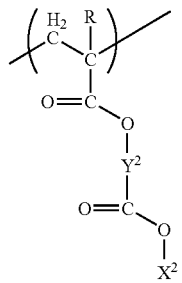

(a1-0-2)

wherein R represents a hydrogen atom, a lower alkyl group or a halogenated lower alkyl group; $X^2$ represents an acid dissociable, dissolution inhibiting group; and $Y^2$ represents an alkylene group, an aliphatic cyclic group or a divalent linkage group having an ether bond.

In general formula (a1-0-1) shown above, lower alkyl group and halogenated lower alkyl group for R are the same as the lower alkyl group and halogenated lower alkyl group which can be bonded to the α-position of the aforementioned acrylate ester.

$X^1$ is not particularly limited as long as it is an acid dissociable, dissolution inhibiting group. Examples thereof include the aforementioned tertiary alkyl ester-type acid dissociable, dissolution inhibiting groups and acetal-type acid dissociable, dissolution inhibiting groups, and tertiary alkyl ester-type acid dissociable, dissolution inhibiting groups are preferable.

In general formula (a1-0-2), R is as defined above.

$X^2$ is as defined for $X^1$ in general formula (a1-0-1).

$Y^2$ represents an alkylene group, an aliphatic cyclic group or a divalent linkage group having an ether bond.

When $Y^2$ is an alkylene group, it is preferably an alkylene group of 1 to 10 carbon atoms, more preferably an alkylene group of 1 to 6 carbon atoms, still more preferably an alkylene group of 1 to 4 carbon atoms, and most preferably an alkylene group of 1 to 3 carbon atoms.

When $Y^2$ is an aliphatic cyclic group, it is preferably a divalent aliphatic cyclic group. As the aliphatic cyclic group, the same aliphatic cyclic groups as those mentioned above in connection with the explanation of "aliphatic cyclic group" can be used, except that two hydrogen atoms have been removed therefrom.

When $Y^2$ represents a divalent aliphatic cyclic group, it is particularly desirable that the divalent aliphatic cyclic group be a group in which two or more hydrogen atoms have been removed from cyclopentane, cyclohexane, norbornane, isobornane, adamantane, tricyclodecane or tetracyclododecane.

When $Y^2$ is a divalent linkage group having an ether bond, it is preferably a group represented by the formula: $-Y^a-O-Y^b-$.

In the group represented by the formula: $-Y^a-O-Y^b-$, $Y^a$ represents a divalent hydrocarbon group of 2 or more carbon atoms which may have a substituent. The hydrocarbon group may be either an aliphatic hydrocarbon group or an aromatic hydrocarbon group, although an aliphatic hydrocarbon group is preferable. As the aliphatic hydrocarbon group, a linear or branched aliphatic hydrocarbon group and an aliphatic hydrocarbon group containing a ring in the structure thereof can be mentioned. More specifically, such groups are the same as the divalent aliphatic cyclic group and alkylene group for $Y^2$ which have 2 or more carbon atoms. Further, $Y^a$ may have a substituent. When $Y^a$ is a linear or branched aliphatic hydrocarbon group, as the substituent, a fluorine atom, a fluorinated alkyl group of 1 to 5 carbon atoms and an oxygen atom (=O) can be mentioned. When $Y^a$ is an aliphatic hydrocarbon group containing a ring in the structure thereof, as the substituent, the same substituents as those for the aforementioned "aliphatic cyclic group" can be mentioned.

$Y^a$ is preferably a linear aliphatic hydrocarbon group, more preferably a linear alkylene group, still more preferably a linear alkylene group of 2 to 5 carbon atoms, and most preferably an ethylene group.

$Y^b$ represents a divalent hydrocarbon group of 1 or more carbon atoms which may have a substituent. As the hydrocarbon group for $Y^6$, the same as the divalent hydrocarbon group of 2 or more carbon atoms for $Y^a$, and a methylene group which may have a substituent can be mentioned. As the substituent which a methylene group may have, the same substituents as those which a linear or branched aliphatic hydrocarbon group may have can be mentioned.

As $Y^b$, a linear or branched aliphatic hydrocarbon group is preferable, and a methylene group or an alkylmethylene group is particularly desirable.

The alkyl group within the alkylmethylene group is preferably a linear alkyl group of 1 to 5 carbon atoms, more preferably a linear alkyl group of 1 to 3 carbon atoms, and most preferably a methyl group.

Specific examples of the structural unit (a1) include structural units represented by general formulas (a1-1) to (a1-4) shown below.

[Chemical Formula 44]

(a1-1)

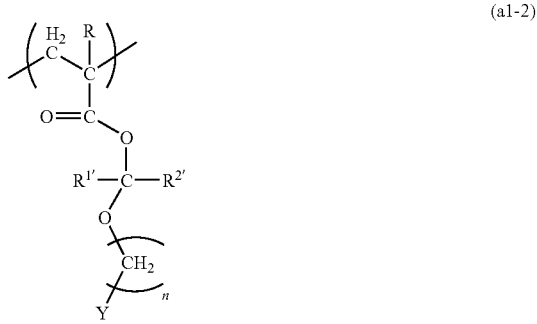

(a1-2)

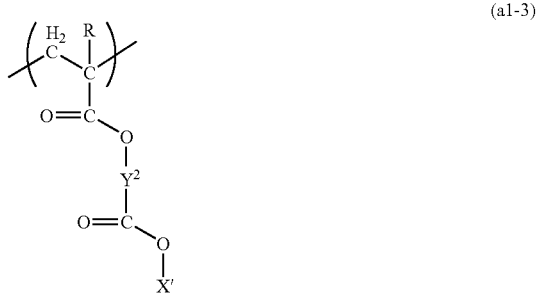

(a1-3)

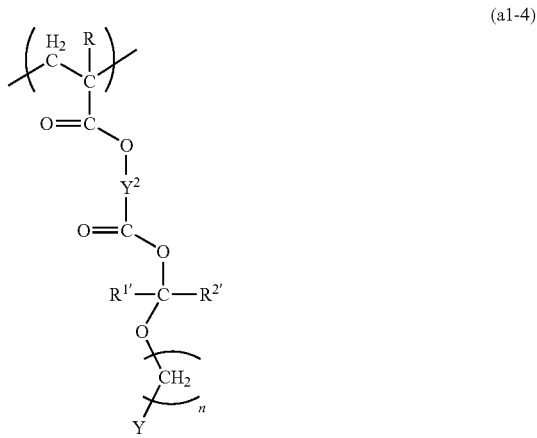

(a1-4)

wherein X' represents a tertiary alkyl ester-type acid dissociable, dissolution inhibiting group; Y represents a lower alkyl group of 1 to 5 carbon atoms or an aliphatic cyclic group; n represents an integer of 0 to 3; $Y^2$ represents an alkylene groups an aliphatic cyclic group or a divalent linkage group having an ether bond; R is as defined above; and each of $R^{1'}$ and $R^{2'}$ independently represents a hydrogen atom or a lower alkyl group of 1 to 5 carbon atoms.

Examples of the tertiary alkyl ester-type acid dissociable, dissolution inhibiting group for X' are the same as the above-mentioned tertiary alkyl ester-type acid dissociable, dissolution inhibiting groups for $X^1$.

As $R^{1'}$, $R^{2'}$, n and Y, the same as $R^{1'}$, $R^{2'}$, n and Y defined for general formula (p1) described above in connection with the "acetal-type acid dissociable, dissolution inhibiting group" may be mentioned.

As $Y^2$, the same as $Y^2$ defined for general formula (a1-0-2) above may be mentioned.

Specific examples of structural units represented by general formula (a1-1) to (a1-4) are shown below.

[Chemical Formula 45]

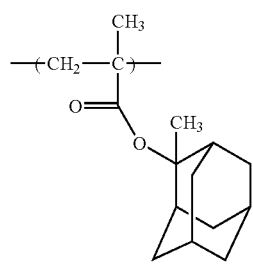
(a1-1-1)

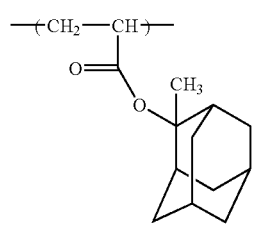
(a1-1-2)

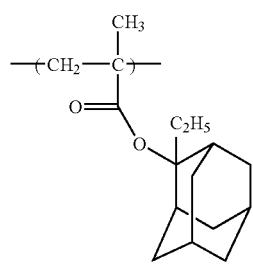
(a1-1-3)

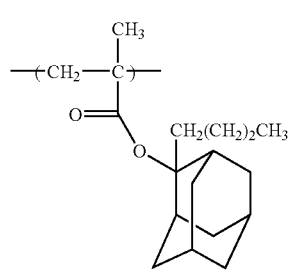
(a1-1-4)

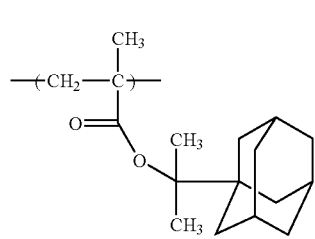
(a1-1-5)

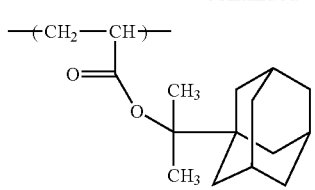
(a1-1-6)

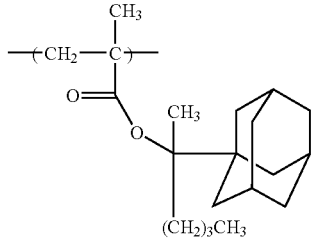
(a1-1-7)

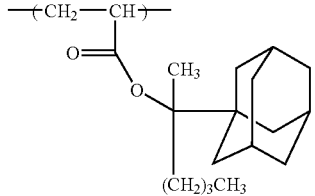
(a1-1-8)

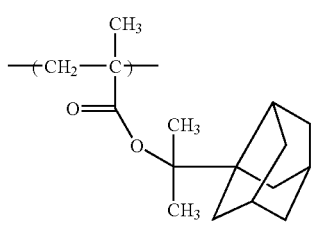
(a1-1-9)

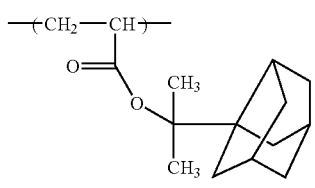
(a1-1-10)

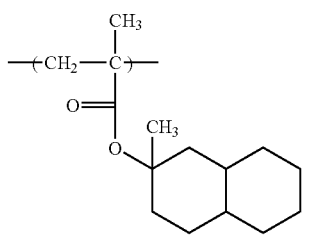
(a1-1-11)

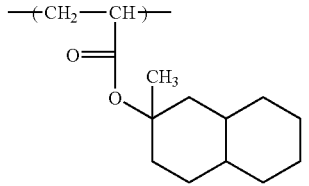
(a1-1-12)

-continued (a1-1-13)

(a1-1-14)

(a1-1-15)

(a1-1-16)

(a1-1-17)

(a1-1-18)

[Chemical Formula 46]

(a1-1-17)

(a1-1-18)

(a1-1-19)

(a1-1-20)

(a1-1-21)

(a1-1-22)

(a1-1-23) 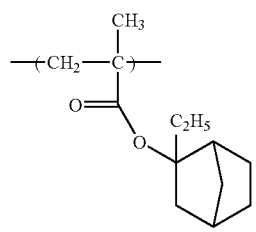
(a1-1-24) 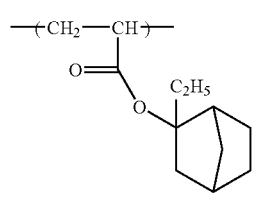
(a1-1-25) 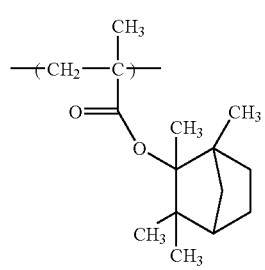
(a1-1-26) 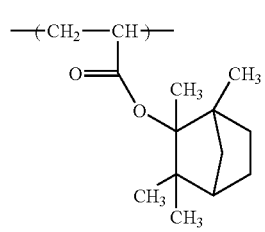
(a1-1-27) 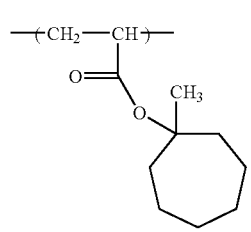
(a1-1-28) 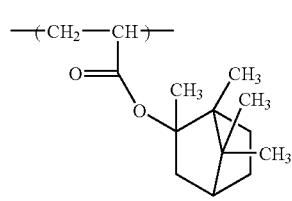
(a1-1-29) 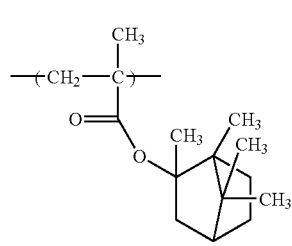
(a1-1-30) 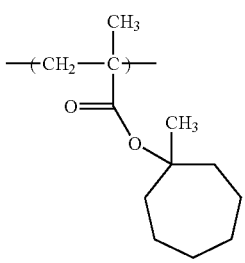
(a1-1-31) 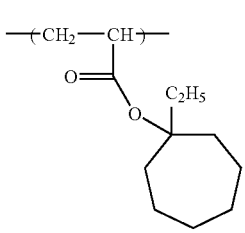
(a1-1-32) 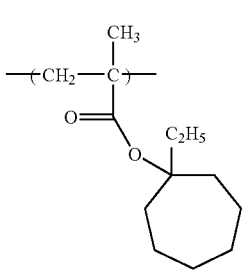
[Chemical Formula 47]
(a1-1-33) 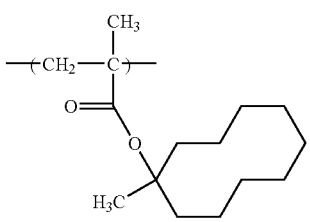
(a1-1-34) 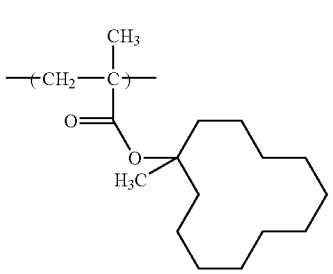
(a1-1-35) 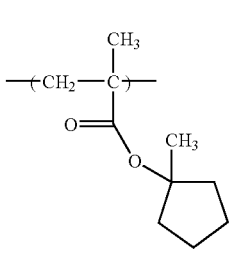

(a1-1-36) 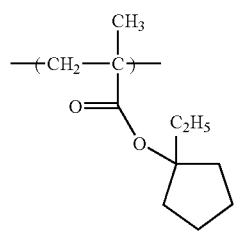
(a1-1-37) 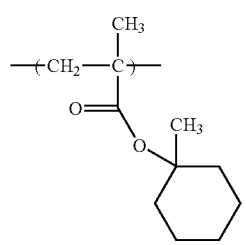
(a1-1-38) 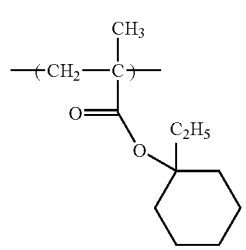
(a1-1-39) 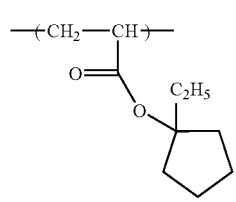
(a1-1-40) 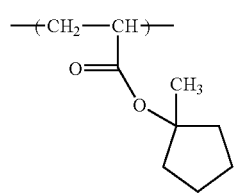
(a1-1-41) 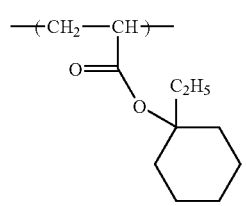
(a1-1-42) 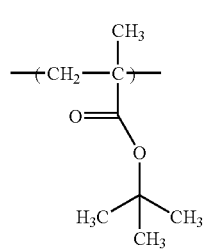
(a1-1-43) 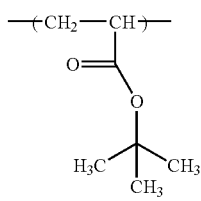
(a1-1-44) 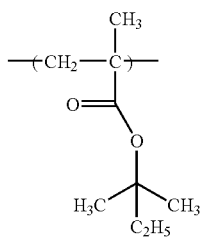
(a1-1-45) 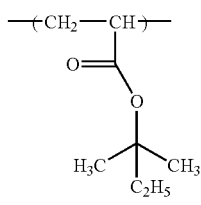
[Chemical Formula 48]
(a1-2-1) 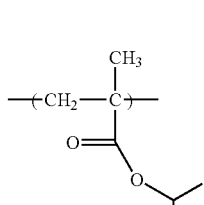
(a1-2-2) 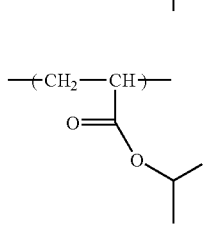
(a1-2-3) 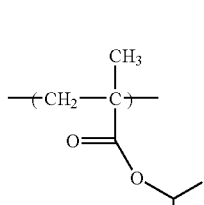
(a1-2-4) 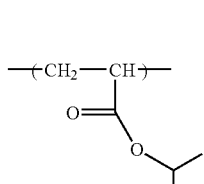

(a1-2-5)
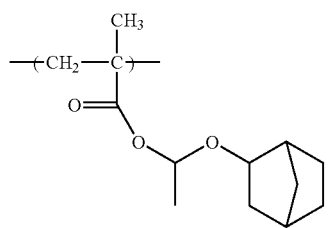
(a1-2-6)
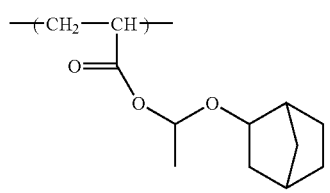
[Chemical Formula 49]
(a1-2-7)
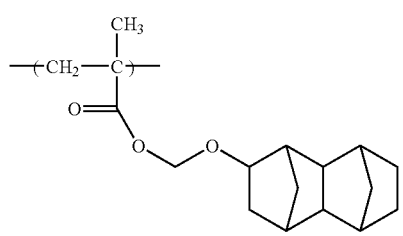
(a1-2-8)
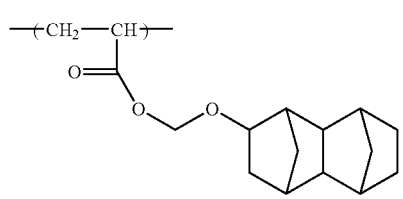
(a1-2-9)
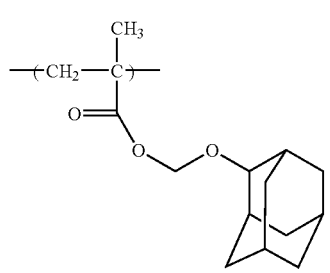
(a1-2-10)
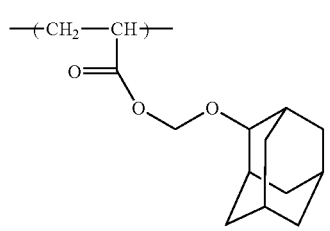
(a1-2-11)
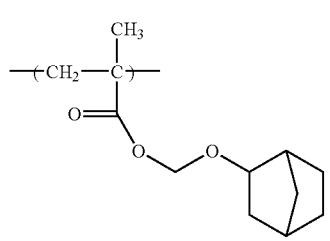
(a1-2-12)
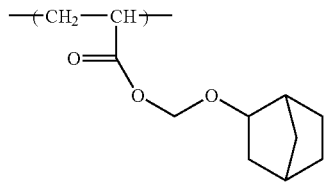
(a1-2-13)
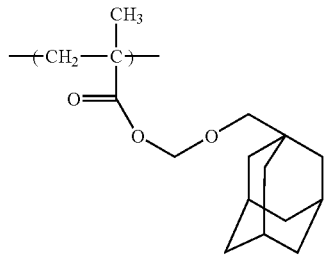
(a1-2-14)
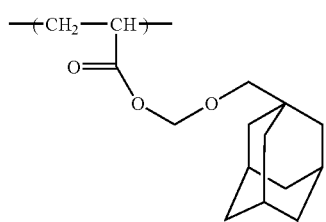
(a1-2-15)
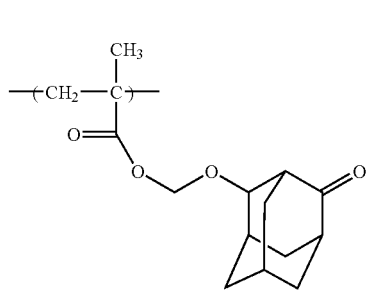
(a1-2-16)
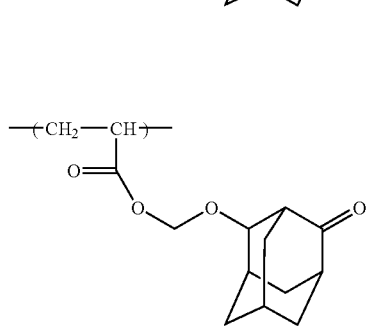
(a1-2-17)
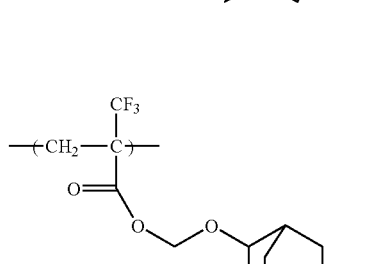

(a1-2-18) 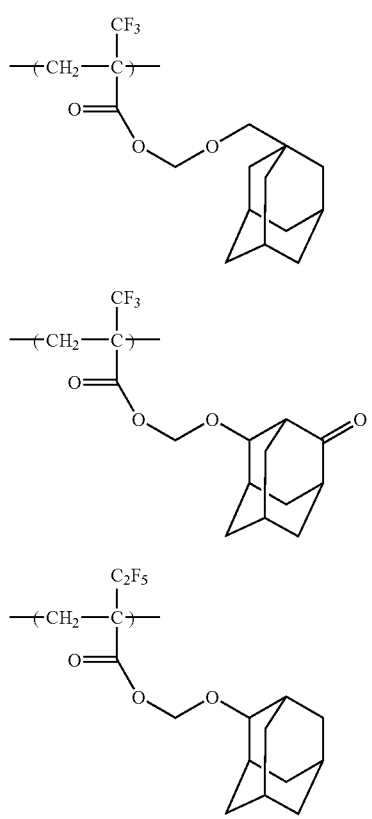
(a1-2-19)
(a1-2-20)
[Chemical Formula 50]
(a1-2-21) 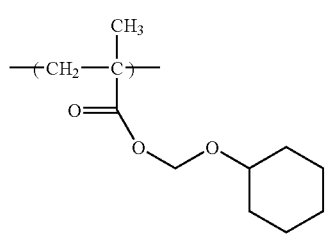
(a1-2-22) 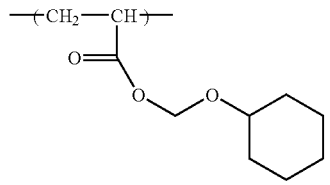
(a1-2-23) 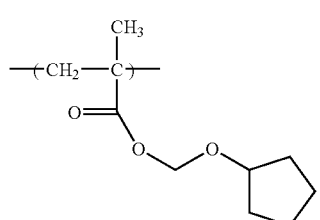
(a1-2-24) 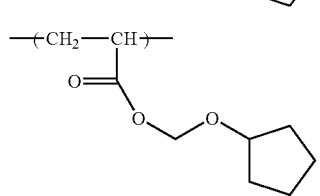
(a1-2-25) 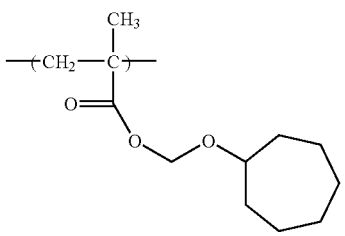
(a1-2-26) 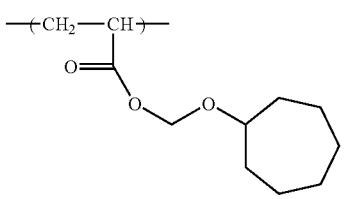
(a1-2-27) 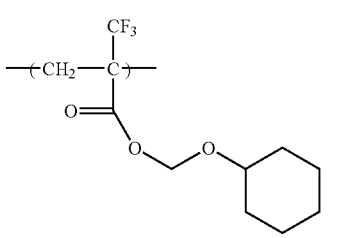
(a1-2-28) 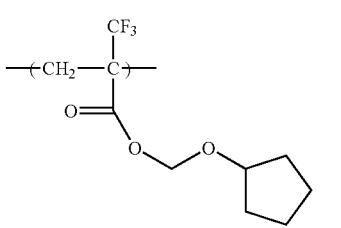
(a1-2-29) 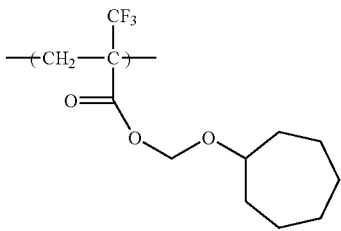
(a1-2-30) 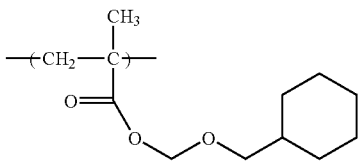
(a1-2-31) 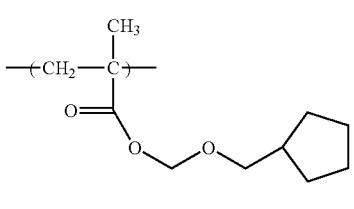

[Chemical Formula 51]
(a1-2-32) 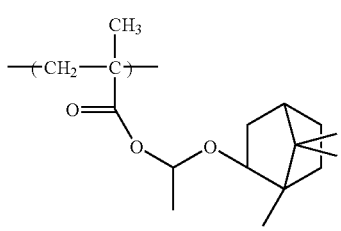
(a1-2-33) 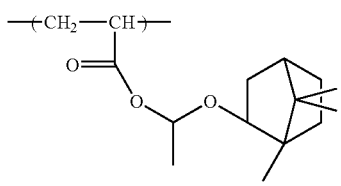
(a1-2-34) 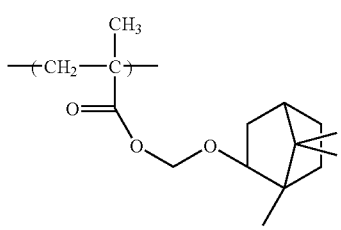
(a1-2-35) 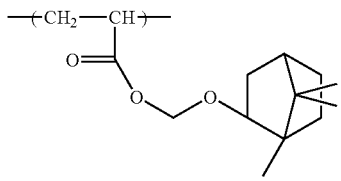
(a1-2-36) 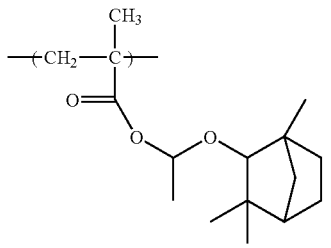
(a1-2-37) 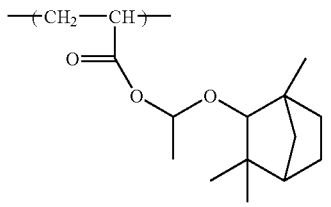
(a1-2-38) 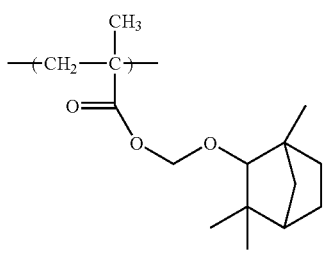
(a1-2-39) 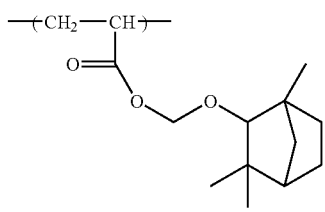
[Chemical Formula 52]
(a1-3-1) 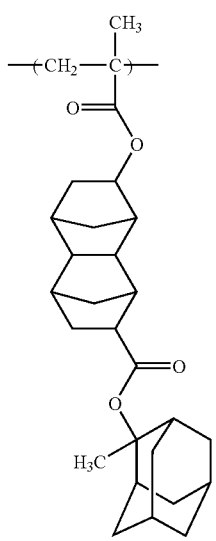
(a1-3-2) 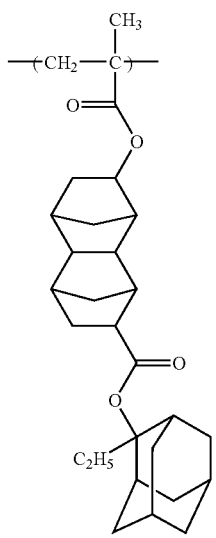

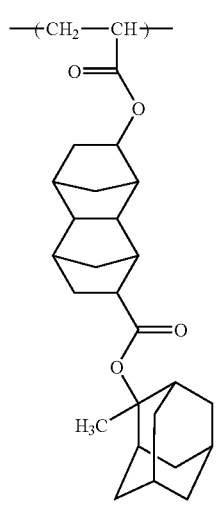 (a1-3-3)
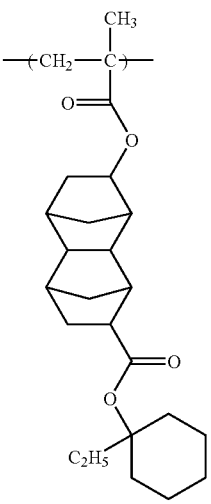 (a1-3-6)
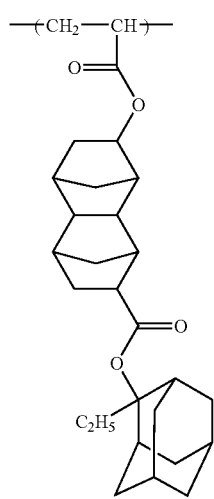 (a1-3-4)
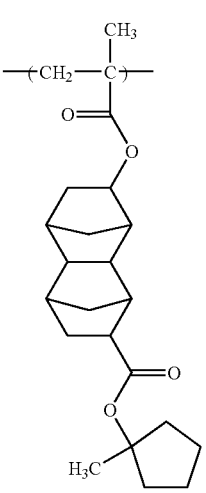 (a1-3-7)
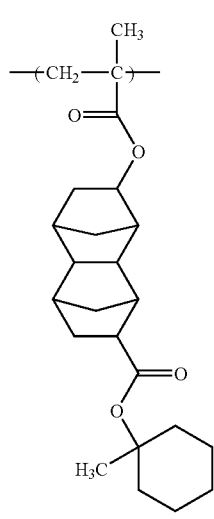 (a1-3-5)
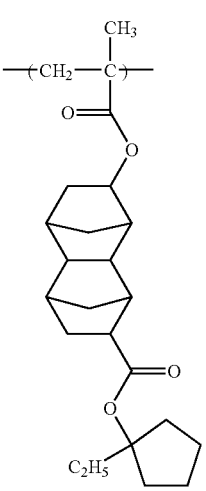 (a1-3-8)

-continued
(a1-3-9)
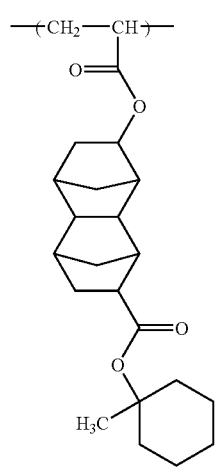
(a1-3-10)
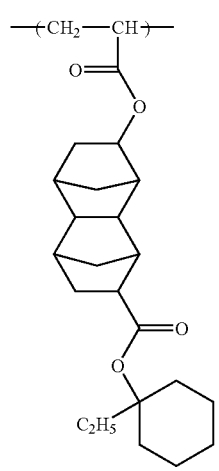
(a1-3-11)
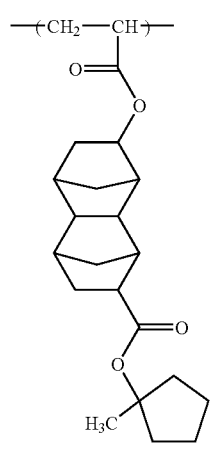
-continued
(a1-3-12)
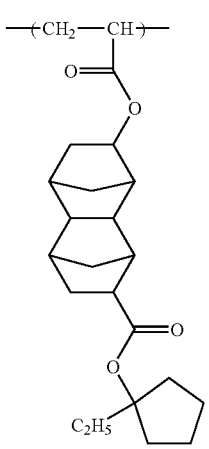
(a1-3-13)
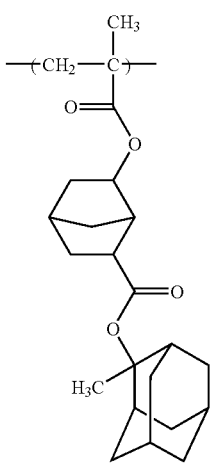
(a1-3-14)
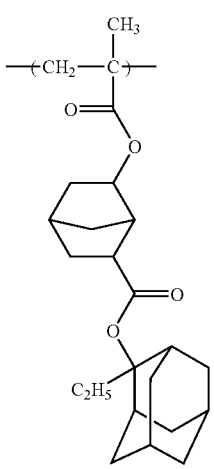

(a1-3-15)
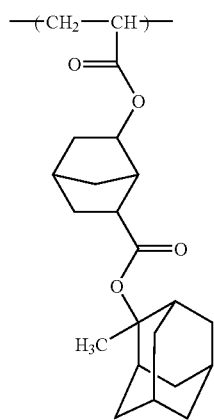
(a1-3-16)
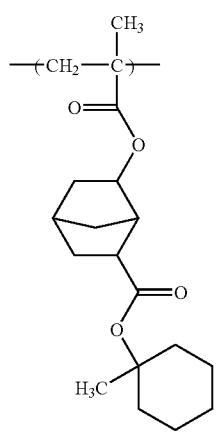
(a1-3-17)
(a1-3-18)
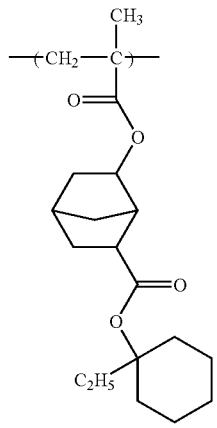
[Chemical Formula 53]
(a1-3-19)
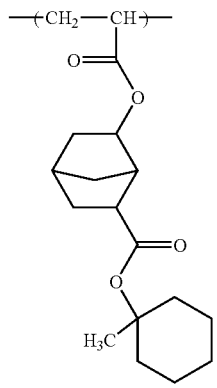
(a1-3-20)
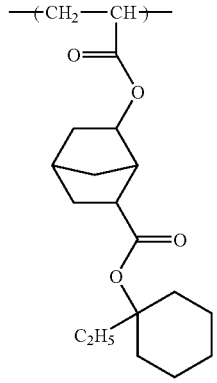
(a1-3-21)
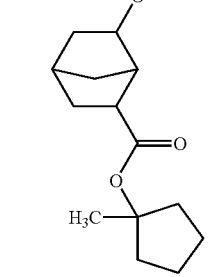

(a1-3-22) 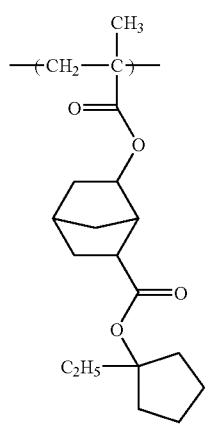
(a1-3-23) 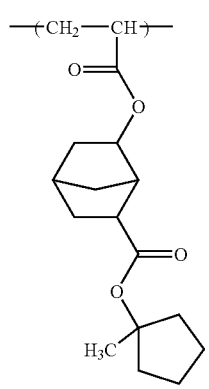
(a1-3-24) 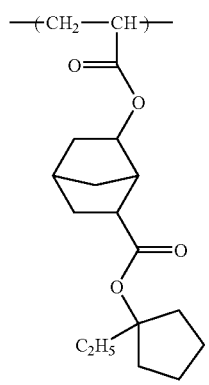
[Chemical Formula 54]
(a1-3-25) 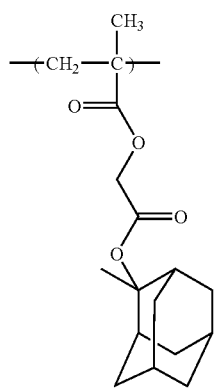
(a1-3-26) 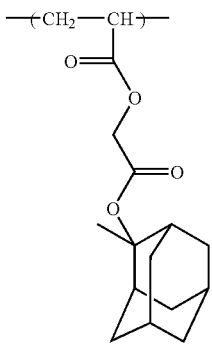
(a1-3-27) 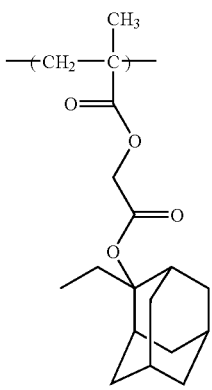
(a1-3-28) 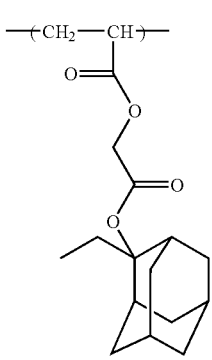
(a1-3-29) 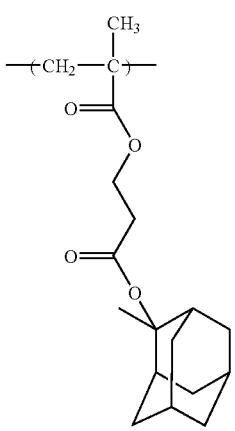

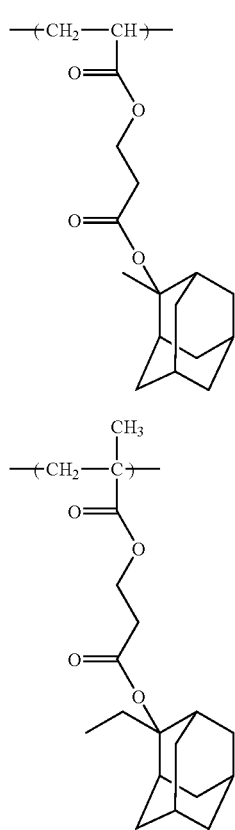
(a1-3-30)
(a1-3-31)
(a1-3-32)
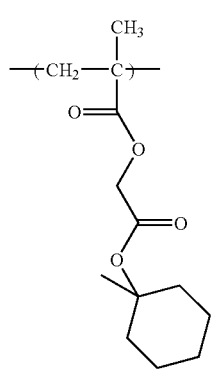
(a1-3-33)
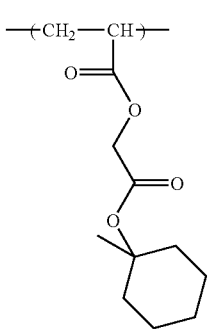
(a1-3-34)
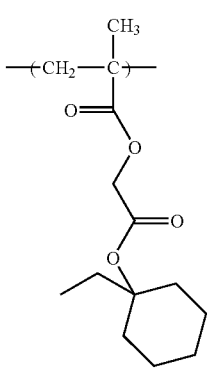
(a1-3-35)
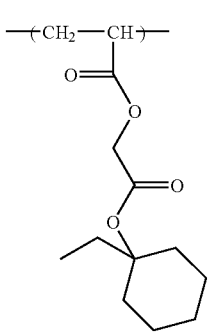
(a1-3-36)
[Chemical Formula 55]
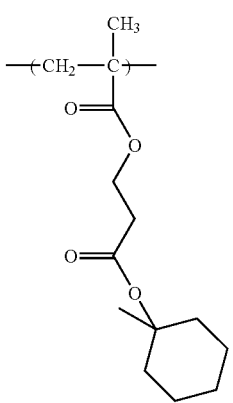
(a1-3-37)

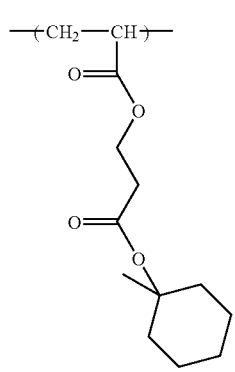 (a1-3-38)
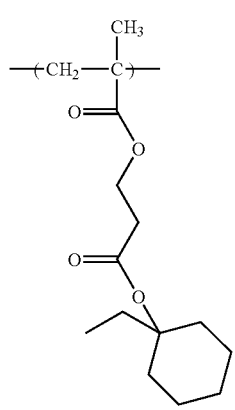 (a1-3-39)
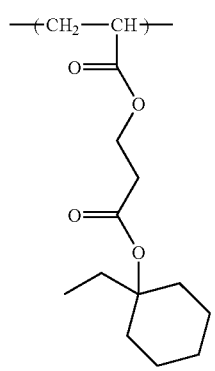 (a1-3-40)
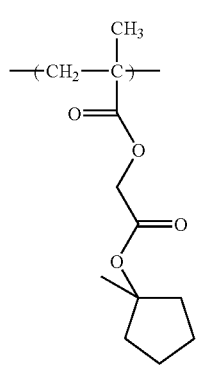 (a1-3-41)
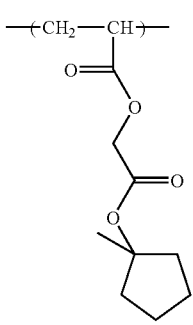 (a1-3-42)
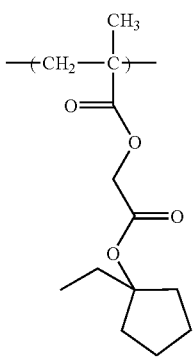 (a1-3-43)
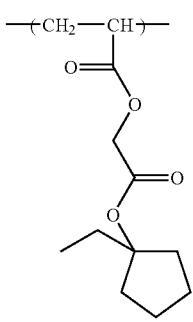 (a1-3-44)
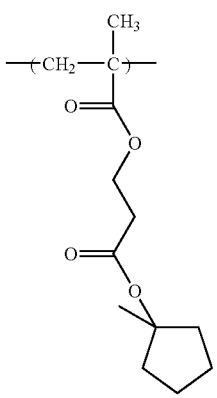 (a1-3-45)

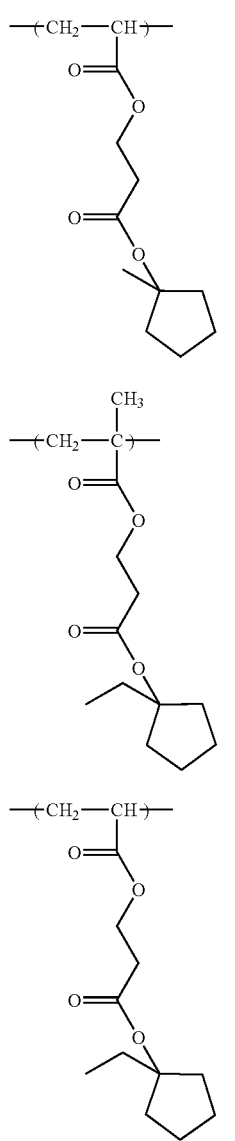
(a1-3-46)
(a1-3-47)
(a1-3-48)
[Chemical Formula 56]
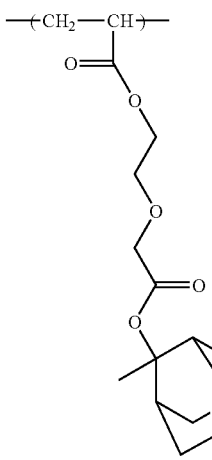
(a1-3-50)
[Chemical Formula 57]
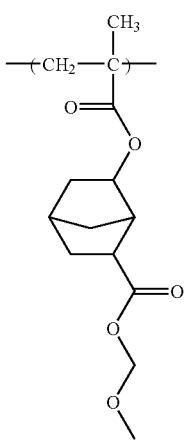
(a1-4-1)
(a1-3-49)
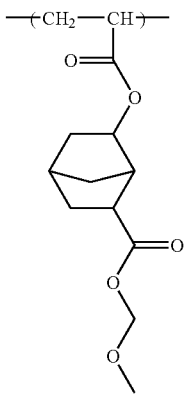
(a1-4-2)

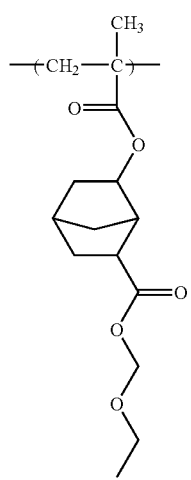
(a1-4-3)
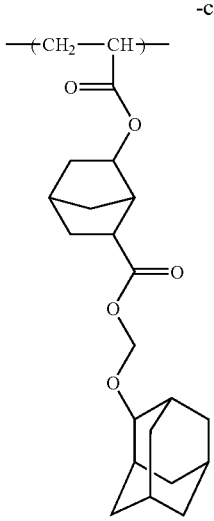
(a1-4-6)
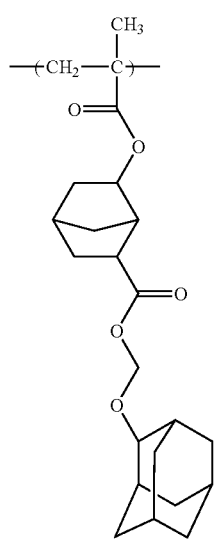
(a1-4-4)
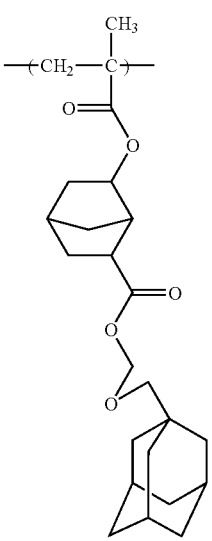
(a1-4-7)
(a1-4-5)
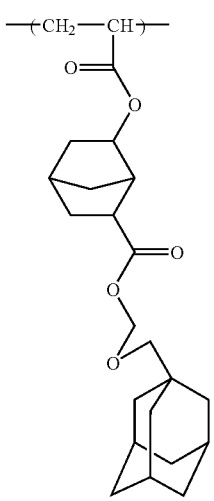
(a1-4-8)

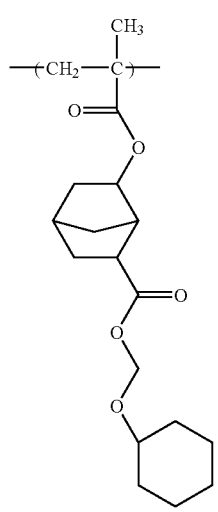 (a1-4-9)
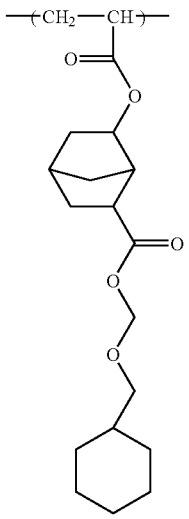 (a1-4-12)
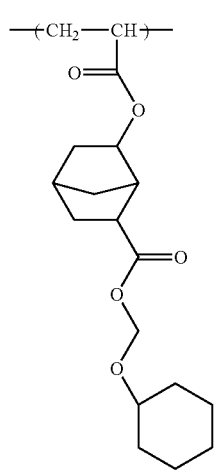 (a1-4-10)
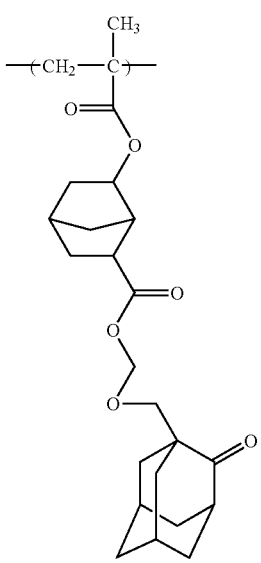 (a1-4-13)
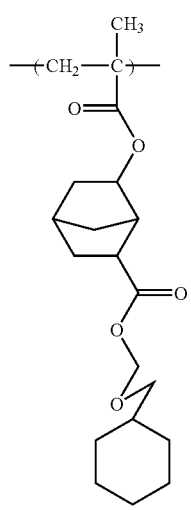 (a1-4-11)
(a1-4-14)

(a1-4-15)
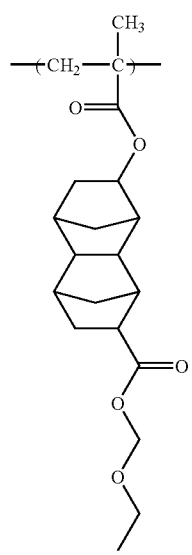
(a1-4-16)
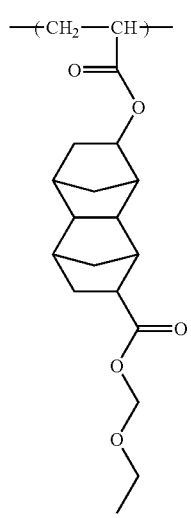
(a1-4-17)
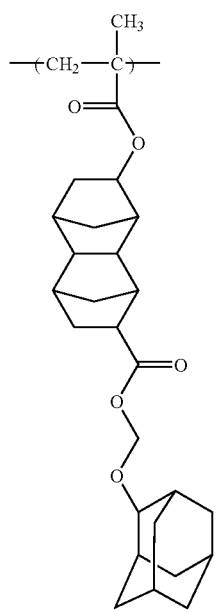
[Chemical Formula 58]
(a1-4-18)
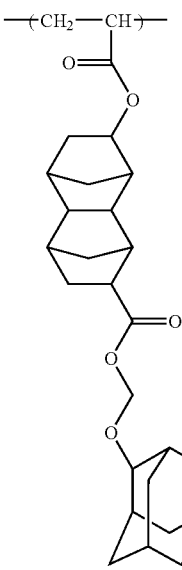
(a1-4-19)

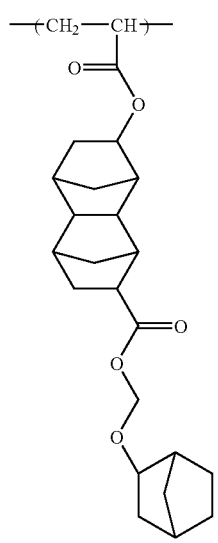 (a1-4-20)
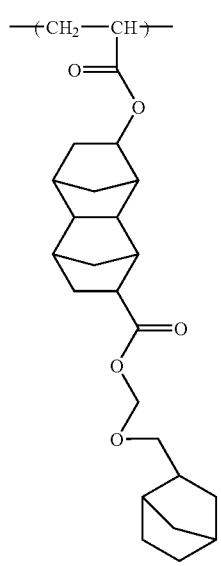 (a1-4-21)
(a1-4-22)
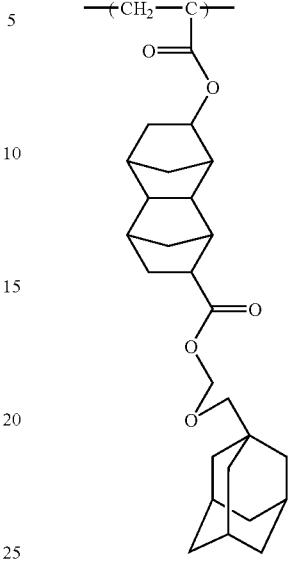 (a1-4-23)
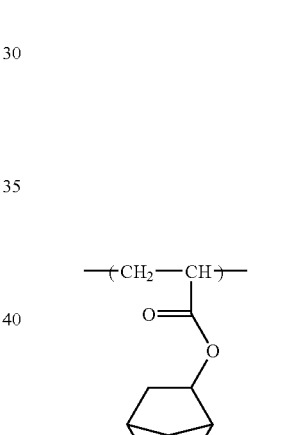 (a1-4-24)

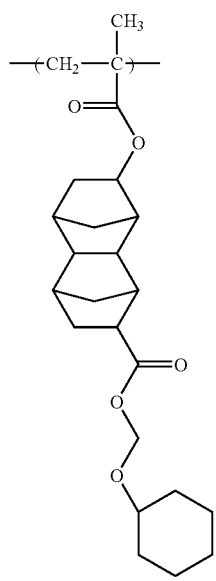
(a1-4-25)
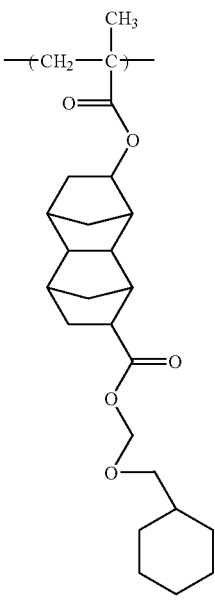
(a1-4-27)
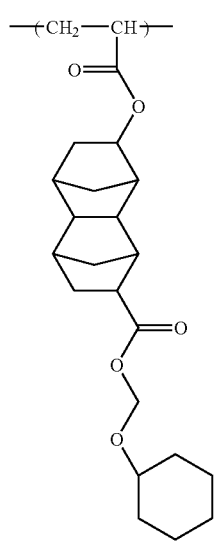
(a1-4-26)
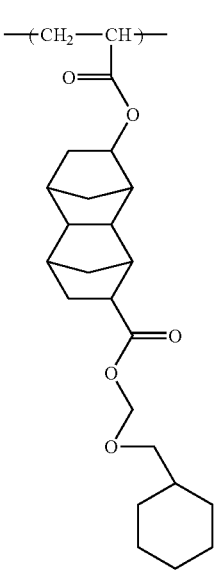
(a1-4-28)

-continued

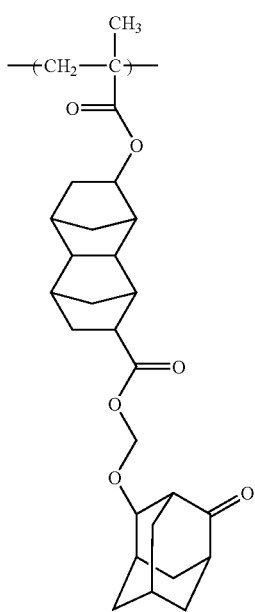

(a1-4-29)

(a1-4-30)

As the structural unit (a1), one type of structural unit may be used alone, or two or more types may be used in combination.

Among these, structural units represented by general formula (a1-1) are preferable. More specifically, at least one structural unit selected from the group consisting of structural units represented by formulas (a1-1-1) to (a-1-1-6) (a1-1-17), (a1-1-18), (a1-1-35) to (a1-1-41), (a1-3-49) and (a1-3-50) is more preferable.

Further, as the structural unit (a1), structural units represented by general formula (a1-1-01) shown below which includes the structural units represented by formulas (a1-1-1) to (a1-1-4), and structural units represented by general formula (a1-1-02) shown below which includes the structural units represented by formulas (a1-1-35) to (a1-1-41) are also preferable.

[Chemical Formula 59]

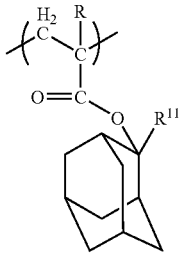

(a1-1-01)

wherein R represents a hydrogen atom, a lower alkyl group or a halogenated lower alkyl group; and $R^{11}$ represents a lower alkyl group.

[Chemical Formula 60]

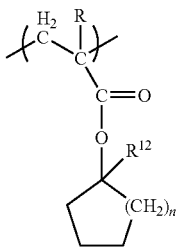

(a1-1-02)

wherein R represents a hydrogen atom, a lower alkyl group or a halogenated lower alkyl group; $R^{12}$ represents a lower alkyl group; and h represents an integer of 1 to 3.

In general formula (a1-1-01), R is as defined above. The lower alkyl group for $R^{11}$ is the same as the lower alkyl group for R above, and is preferably a methyl group or an ethyl group.

In general formula (a1-1-02), R is as defined above. The lower alkyl group for $R^{12}$ is the same as the lower alkyl group for R above. $R^{12}$ is preferably a methyl group or an ethyl group, and most preferably an ethyl group. h is preferably 1 or 2, and most preferably 2.

As the structural unit (a1), one type of structural unit may be used alone, or two or more types may be used in combination.

In the component (A1), the amount of the structural unit (a1) based on the combined total of all structural units constituting the component (A1) is preferably 10 to 80 mol %, more preferably 20 to 70 mol %, and still more preferably 25 to 50 mol %. By making the amount of the structural unit (a1) at least as large as the lower limit of the above-mentioned range, a pattern can be easily formed using a resist composition prepared from the component (A1). On the other hand, by making the amount of the structural unit (a1) no more than the upper limit of the above-mentioned range, a good balance can be achieved with the other structural units.

Structural Unit (a2)

The structural unit (a2) is a structural unit derived from an acrylate ester containing a lactone-containing cyclic group.

The term "lactone-containing cyclic group" refers to a cyclic group including one ring containing a —O—C(O)— structure (lactone ring). The term "lactone ring" refers to a single ring containing a —O—C(O)— structure, and this ring is counted as the first ring. A lactone-containing cyclic group in which the only ring structure is the lactone ring is referred to as a monocyclic group, and groups containing other ring structures are described as polycyclic groups regardless of the structure of the other rings.

When the component (A1) is used for forming a resist film, the lactone-containing cyclic group of the structural unit (a2) is effective in improving the adhesion between the resist film and the substrate, and increasing the compatibility with the developing solution containing water.

As the structural unit (a2), there is no particular limitation, and an arbitrary structural unit may be used.

Specific examples of lactone-containing monocyclic groups include groups in which one hydrogen atom has been removed from γ-butyrolactone. Furthers specific examples of lactone-containing polycyclic groups include groups in which one hydrogen atom has been removed from a lactone ring-containing bicycloalkane, tricycloalkane or tetracycloalkane.

More specifically, examples of the structural unit (a2) include structural units represented by general formulas (a2-1) to (a2-5) shown below.

[Chemical Formula 61]

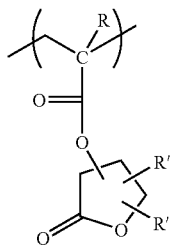

(a2-1)

(a2-2)

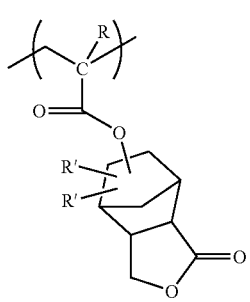

(a2-3)

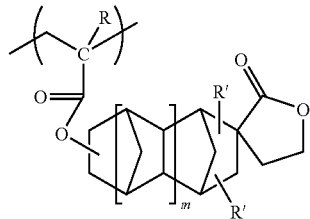

(a2-4)

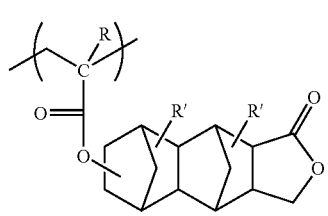

(a2-5)

wherein R represents a hydrogen atom, a lower alkyl group or a halogenated lower alkyl group; R' represents a hydrogen atom, a lower alkyl group, an alkoxy group of 1 to 5 carbon atoms or —COOR", wherein R" represents a hydrogen atom or a linear, branched or cyclic alkyl group of 1 to 15 carbon atoms; m represents 0 or 1; and A" represents an alkylene group of 1 to 5 carbon atoms which may contain an oxygen atom or a sulfur atom, an oxygen atom, or a sulfur atom.

In general formulas (a2-1) to (a2-5), R is the same as R in the structural unit (a1).

The lower alkyl group for R' is the same as the lower alkyl group for R in the structural unit (a1).

When R" is a linear or branched alkyl group, it preferably has 1 to 10 carbon atoms, more preferably 1 to 5 carbon atoms.

When R" is a cyclic alkyl group, it preferably has 3 to 15 carbon atoms, more preferably 4 to 12 carbon atoms, and most preferably 5 to 10 carbon atoms. Examples thereof include groups in which one or more hydrogen atoms have been removed from a monocycloalkane or a polycycloalkane such as a bicycloalkane, tricycloalkane or tetracycloalkane, and which may or may not be substituted with fluorine atoms or fluorinated alkyl groups. Specific examples include groups in which one or more hydrogen atoms have been removed from a monocycloalkane such as cyclopentane or cyclohexane, and groups in which one or more hydrogen atoms have been removed from a polycycloalkane such as adamantane, norbornane, isobornane, tricyclodecane or tetracyclododecane.

In the structural units represented by general formulas (a2-1) to (a2-5), in consideration of industrial availability, R' is preferably a hydrogen atom.

As specific examples of the alkylene group of 1 to 5 carbon atoms for A" which may contain an oxygen atom or a sulfur atom, a methylene group, an ethylene group, an n-propylene group, an isopropylene group, —O—CH$_2$—, —CH$_2$—O—CH$_2$—, —S—CH$_2$— and —CH$_2$—S—CH$_2$— can be mentioned.

Specific examples of structural units represented by general formulas (a2-1) to (a2-5) above are shown below.
[Chemical Formula 62]
(a2-1-1)
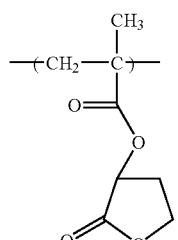
(a2-1-2)
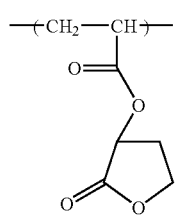
(a2-1-3)
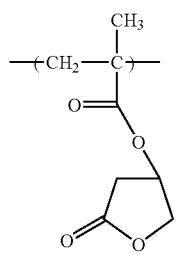
(a2-1-4)
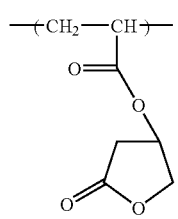
(a2-1-5)
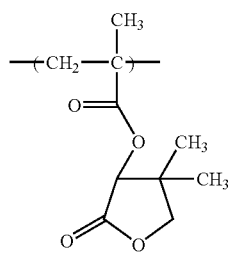
(a2-1-6)
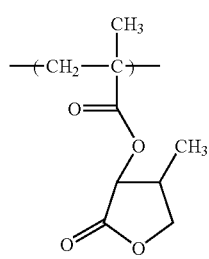
-continued
[Chemical Formula 63]
(a2-2-1)
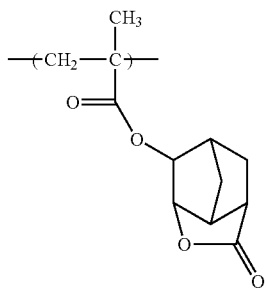
(a2-2-2)
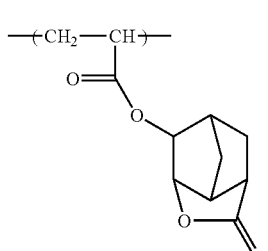
(a2-2-3)
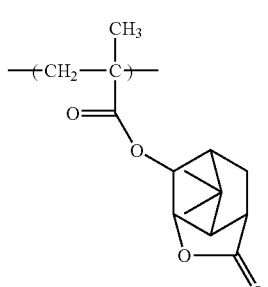
(a2-2-4)
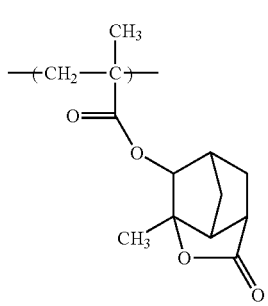
(a2-2-5)
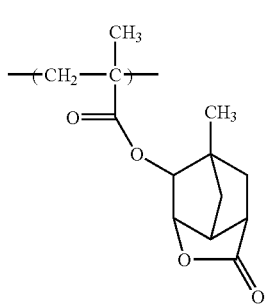

(a2-2-6) 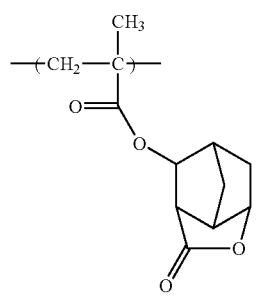
(a2-2-7) 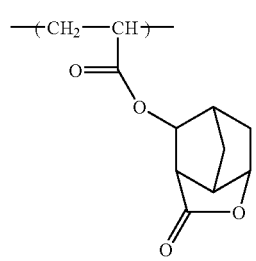
(a2-2-8) 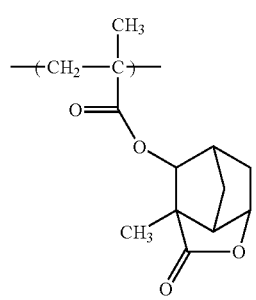
(a2-2-9) 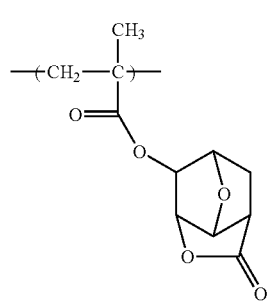
(a2-2-10) 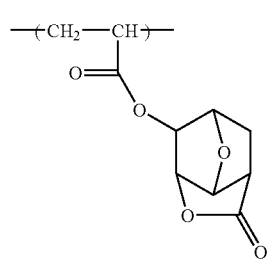
(a2-2-11) 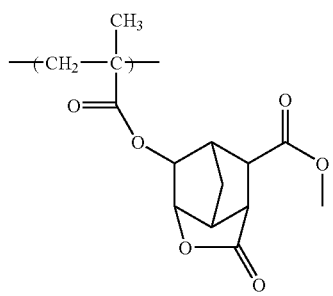
(a2-2-12) 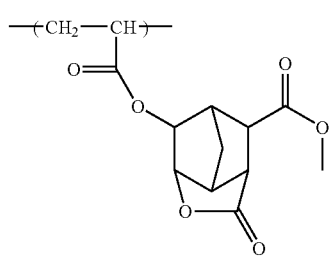
(a2-2-13) 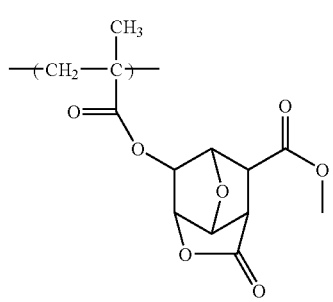
(a2-2-14) 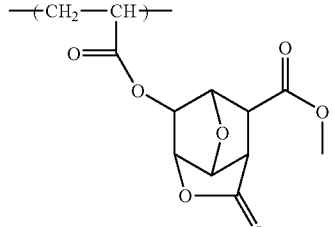
[Chemical Formula 64]
(a2-3-1) 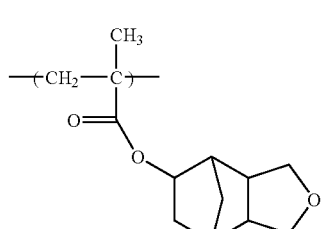
(a2-3-2) 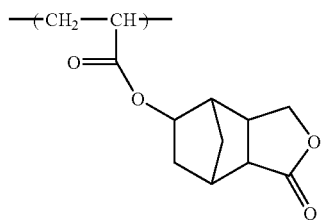

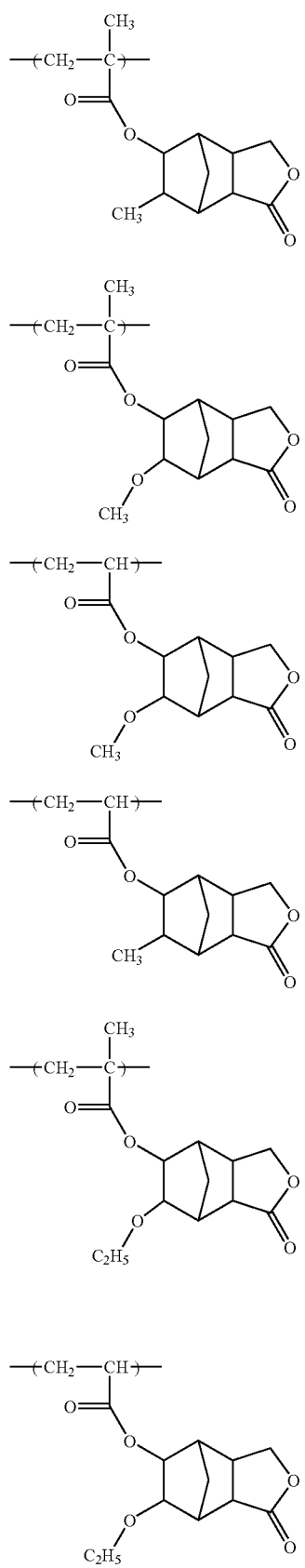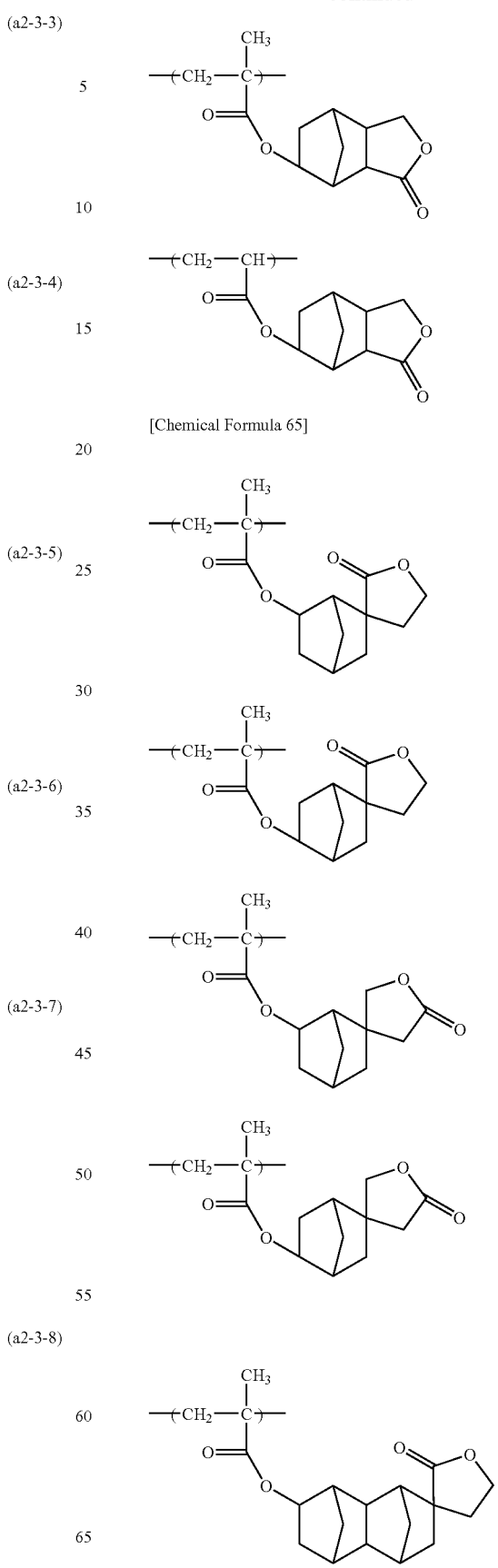

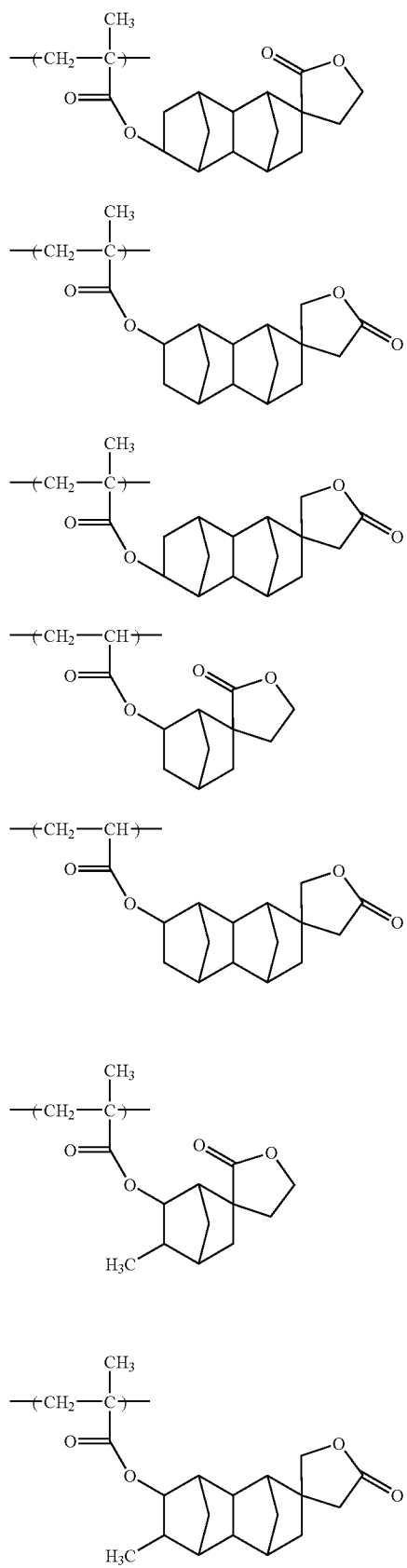
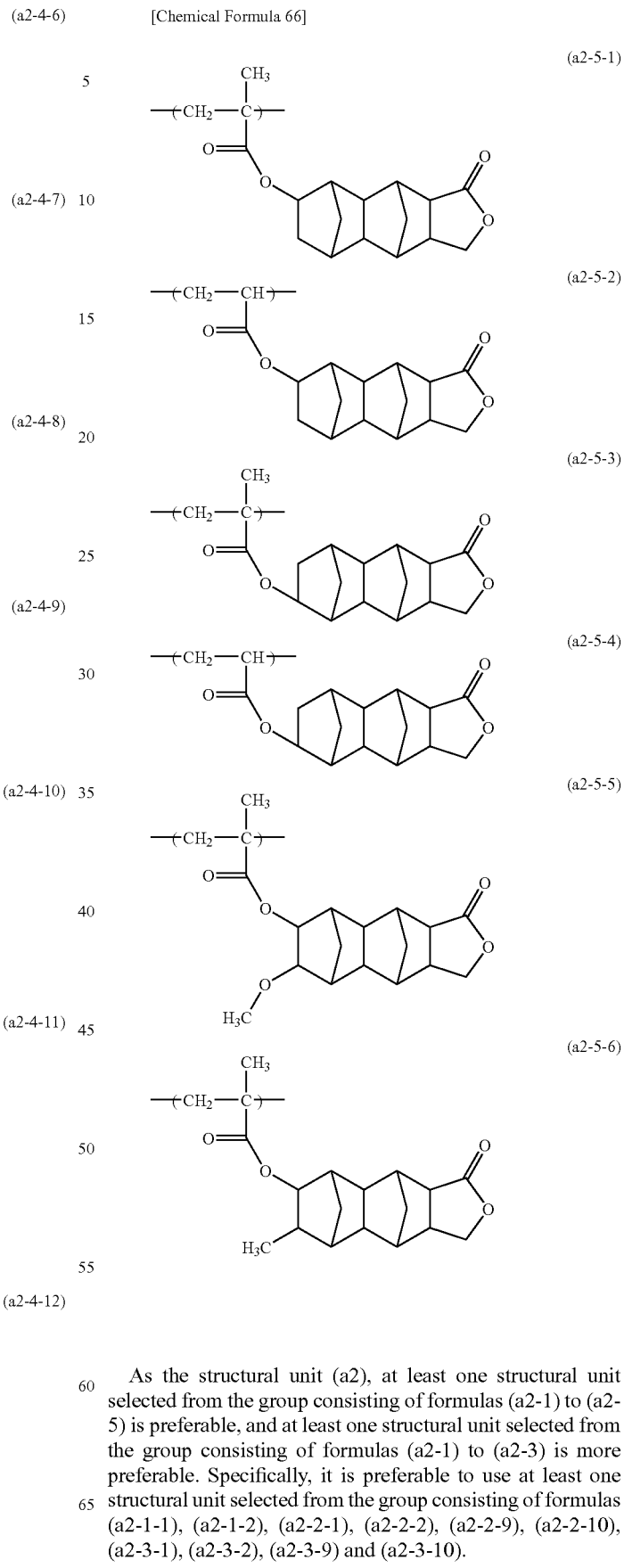
As the structural unit (a2), at least one structural unit selected from the group consisting of formulas (a2-1) to (a2-5) is preferable, and at least one structural unit selected from the group consisting of formulas (a2-1) to (a2-3) is more preferable. Specifically, it is preferable to use at least one structural unit selected from the group consisting of formulas (a2-1-1), (a2-1-2), (a2-2-1), (a2-2-2), (a2-2-9), (a2-2-10), (a2-3-1), (a2-3-2), (a2-3-9) and (a2-3-10).

As the structural unit (a2), one type of structural unit may be used, or two or more types may be used in combination.

In the component (A1), the amount of the structural unit (a2) based on the combined total of all structural units constituting the component (A1) is preferably 5 to 60 mol %, more preferably 10 to 50 mol %, and still more preferably 20 to 50 mol %. By making the amount of the structural unit (a2) at least as large as the lower limit of the above-mentioned range, the effect of using the structural unit (a2) can be satisfactorily achieved. On the other hand, by making the amount of the structural unit (a2) no more than the upper limit of the above-mentioned range, a good balance can be achieved with the other structural units.

Structural Unit (a3)

The structural unit (a3) is a structural unit derived from an acrylate ester containing a polar group-containing aliphatic hydrocarbon group.

When the component (A1) includes the structural unit (a3), the hydrophilicity of the component (A1) is improved, and hence, the compatibility of the component (A1) with the developing solution is improved. As a result, the alkali solubility of the exposed portions improves, which contributes to favorable improvements in the resolution.

Examples of the polar group include a hydroxyl group, cyano group, carboxyl group, or hydroxyalkyl group in which some of the hydrogen atoms of the alkyl group have been substituted with fluorine atoms, although a hydroxyl group is particularly desirable.

Examples of the aliphatic hydrocarbon group include linear or branched hydrocarbon groups (and preferably alkylene groups) of 1 to 10 carbon atoms, and polycyclic aliphatic hydrocarbon groups (polycyclic groups). These polycyclic groups can be selected appropriately from the multitude of groups that have been proposed for the resins of resist compositions designed for use with ArF excimer lasers. The polycyclic group preferably has 7 to 30 carbon atoms.

Of the various possibilities, structural units derived from an acrylate ester that include an aliphatic polycyclic group that contains a hydroxyl group, cyano group, carboxyl group or a hydroxyalkyl group in which some of the hydrogen atoms of the alkyl group have been substituted with fluorine atoms are particularly desirable. Examples of polycyclic groups include groups in which two or more hydrogen atoms have been removed from a bicycloalkane, tricycloalkane, tetracycloalkane or the like. Specific examples include groups in which two or more hydrogen atoms have been removed from a polycycloalkane such as adamantane, norbornane, isobornane, tricyclodecane or tetracyclododecane. Of these polycyclic groups, groups in which two or more hydrogen atoms have been removed from adamantane, norbornane or tetracyclododecane are preferred industrially.

When the aliphatic hydrocarbon group within the polar group-containing aliphatic hydrocarbon group is a linear or branched hydrocarbon group of 1 to 10 carbon atoms, the structural unit (a3) is preferably a structural unit derived from a hydroxyethyl ester of acrylic acid. On the other hand, when the hydrocarbon group is a polycyclic group, structural units represented by formulas (a3-1), (a3-2), and (a3-3) shown below are preferable.

[Chemical Formula 67]

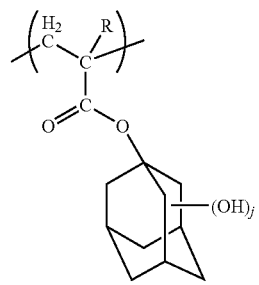

(a3-1)

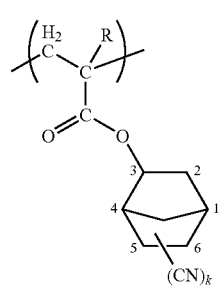

(a3-2)

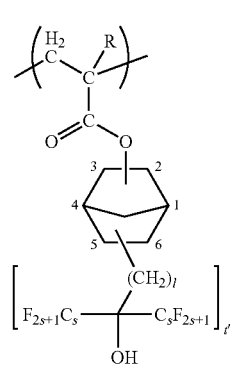

(a3-3)

wherein R is as defined above; j is an integer of 1 to 3; k is an integer of 1 to 3; t' is an integer of 1 to 3; 1 is an integer of 1 to 5; and s is an integer of 1 to 3.

In formula (a3-1), j is preferably 1 or 2, and more preferably 1. When j is 2, it is preferable that the hydroxyl groups be bonded to the 3rd and 5th positions of the adamantyl group. When j is 1, it is preferable that the hydroxyl group be bonded to the 3rd position of the adamantyl group.

j is preferably 1, and it is particularly desirable that the hydroxyl group be bonded to the 3rd position of the adamantyl group.

In formula (a3-2), k is preferably 1. The cyano group is preferably bonded to the 5th or 6th position of the norbornyl group.

In formula (a3-3), t' is preferably 1, 1 is preferably 1 and s is preferably 1. Further, in formula (a3-3), it is preferable that a 2-norbonyl group or 3-norbonyl group be bonded to the terminal of the carboxy group of the acrylic acid. The fluorinated alkyl alcohol is preferably bonded to the 5th or 6th position of the norbornyl group.

In the component (A1), as the structural unit (a3), one type of structural unit may be used, or two or more types may be used in combination.

When the component (A1) contains the structural unit (a3), the amount of structural unit (a3) based on the combined total of all structural units constituting the component (A1) is preferably 5 to 50 mol %, more preferably 5 to 40 mol %, and still more preferably 5 to 25 mol %. By making the amount of the structural unit (a3) at least as large as the lower limit of the above-mentioned range, the effect of using the structural unit (a3) can be satisfactorily achieved. On the other hand, by making the amount of the structural unit (a3) no more than the upper limit of the above-mentioned range, a good balance can be achieved with the other structural units.

Structural Unit (a4)

The component (A1) may also have a structural unit (a4) which is other than the above-mentioned structural units (a1) to (a3), as long as the effects of the present invention are not impaired.

As the structural unit (a4), any other structural unit which cannot be classified as one of the above structural units (a1) to (a3) can be used without any particular limitations, and any of the multitude of conventional structural units used within resist resins for ArF excimer lasers or KrF excimer lasers (and particularly for ArF excimer lasers) can be used.

As the structural unit (a4), a structural unit which contains a non-acid-dissociable aliphatic polycyclic group, and is also derived from an acrylate ester is preferable. Examples of this polycyclic group include the same groups as those described above in connection with the aforementioned structural unit (a1), and any of the multitude of conventional polycyclic groups used within the resin component of resist compositions for ArF excimer lasers or KrF excimer lasers (and particularly for ArF excimer lasers) can be used.

In consideration of industrial availability and the like, at least one polycyclic group selected from amongst a tricyclodecanyl group, adamantyl group, tetracyclododecanyl group, isobornyl group, and norbornyl group is particularly desirable. These polycyclic groups may be substituted with a linear or branched alkyl group of 1 to 5 carbon atoms.

Specific examples of the structural unit (a4) include units with structures represented by general formulas (a4-1) to (a4-5) shown below.

[Chemical Formula 68]

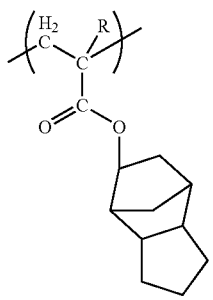
(a41-)

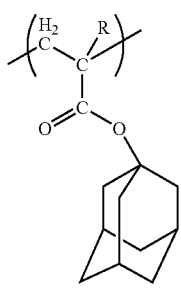
(a4-2)

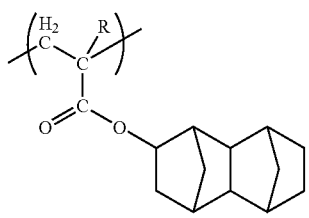
(a4-3)

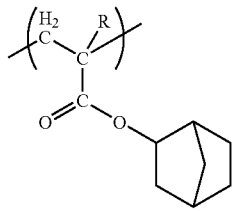
(a4-4)

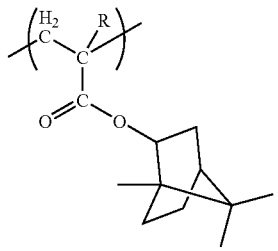
(a4-5)

wherein R is as defined above.

When the structural unit (a4) is included in the component (A1), the amount of the structural unit (a4) based on the combined total of all the structural units that constitute the component (A1) is preferably within the range from 1 to 30 mol %, and more preferably from 10 to 20 mol %.

In the present invention, the component (A1) preferably contains a copolymer having the structural units (a1), (a2) and (a3). Examples of such a copolymer include a copolymer consisting of the structural units (a1) and (a2) and (a3), and a copolymer consisting of the structural units (a1), (a2), (a3) and (a4).

The component (A1) can be obtained, for example, by a conventional radical polymerization or the like of the monomers corresponding with each of the structural units, using a radical polymerization initiator such as azobisisobutyronitrile (AIBN).

Furthermore, in the component (A1), by using a chain transfer agent such as HS—$CH_2$—$CH_2$—$CH_2$—$C(CF_3)_2$—OH, a —$C(CF_3)_2$—OH group can be introduced at the terminals of the component (A1). Such a copolymer having introduced a hydroxyalkyl group in which some of the hydrogen atoms of the alkyl group are substituted with fluorine atoms is effective in reducing developing defects and LER (line edge roughness: unevenness of the side walls of a line pattern).

The weight average molecular weight (Mw) (the polystyrene equivalent value determined by gel permeation chromatography) of the component (A1) is not particularly limited, but is preferably 2,000 to 50,000, more preferably 3,000 to 30,000, and most preferably 5,000 to 20,000. By making the weight average molecular weight no more than the upper limit of the above-mentioned range, the component (A1) exhibits satisfactory solubility in a resist solvent when used as a resist. On the other hand, by making the weight average molecular weight at least as large as the lower limit of the above-mentioned range, dry etching resistance and cross-sectional shape of the resist pattern becomes satisfactory.

Further, the dispersity (Mw/Mn) is preferably 1.0 to 5.0, more preferably 1.0 to 3.0, and most preferably 1.2 to 2.5. Here, Mn is the number average molecular weight.

[Component (A2)]

As the component (A2), it is preferable to use a compound that has a molecular weight of at least 500 and less than 2,000, contains a hydrophilic group, and also contains an acid dissociable, dissolution inhibiting group mentioned above in connection with the component (A1). Specific examples include compounds containing a plurality of phenol skeletons in which a part of the hydrogen atoms within hydroxyl groups have been substituted with the aforementioned acid dissociable, dissolution-inhibiting groups.

Examples of the component (A2) include low molecular weight phenolic compounds in which a portion of the hydroxyl group hydrogen atoms have been substituted with an aforementioned acid dissociable, dissolution inhibiting group, and these types of compounds are known, for example, as sensitizers or heat resistance improvers for use in non-chemically amplified g-line or i-line resists.

Examples of these low molecular weight phenol compounds include bis(4-hydroxyphenyl)methane, bis(2,3,4-trihydroxyphenyl)methane, 2-(4-hydroxyphenyl)-2-(4'-hydroxyphenyl)propane, 2-(2,3,4-trihydroxyphenyl)-2-(2',3', 4'-trihydroxyphenyl)propane, tris(4-hydroxyphenyl)methane, bis(4-hydroxy-3,5-dimethylphenyl)-2-hydroxyphenylmethane, bis(4-hydroxy-2,5-dimethylphenyl)-2-hydroxyphenylmethane, bis(4-hydroxy-3,5-dimethylphenyl)-3,4-dihydroxyphenylmethane, bis(4-hydroxy-2,5-dimethylphenyl)-3,4-dihydroxyphenylmethane, bis(4-hydroxy-3-methylphenyl)-3,4-dihydroxyphenylmethane, bis(3-cyclohexyl-4-hydroxy-6-methylphenyl)-4-hydroxyphenylmethane, bis(3-cyclohexyl-4-hydroxy-6-methylphenyl)-3,4-dihydroxyphenylmethane, 1-[1-(4-hydroxyphenyl)isopropyl]-4-[1,1-bis(4-hydroxyphenyl)ethyl]benzene, and dimers, trimers and tetramers of formalin condensation products of phenols such as phenol, m-cresol, p-cresol and xylenol. Needless to say, the low molecular weight phenol compound is not limited to these examples.

Also, there are no particular limitations on the acid dissociable, dissolution inhibiting group, and suitable examples include the groups described above.

As the component (A), one type may be used, or two or more types may be used in combination.

In the resist composition of the present invention, the amount of the component (A) can be appropriately adjusted depending on the thickness of the resist film to be formed, and the like.

<Component (B)>

The component (B) includes an acid generator (B1) (hereafter, referred to as "component (B1)") consisting of a compound represented by general formula (b1-1) above. The component (B1) is the same as the aforementioned compound (B1) of the present invention.

As the component (B1), one type may be used, or two or more types may be used in combination.

In the resist composition of the present invention, the amount of the component (B1) within the component (B) is preferably 40% by weight or more, more preferably 70% by weight or more, and may be even 100% by weight. It is particularly desirable that the amount of the component (B1) within the component (B) be 100% by weight. By making the amount of the component (B1) at least as large as the lower limit of the above-mentioned range, lithography properties such as resolution, mask reproducibility, line width roughness (LWR), pattern shape, exposure margin (EL margin) and depth of focus (DOF) are improved when a resist pattern is formed using the resist composition.

In the component (B), an acid generator (B2) other than the aforementioned component (B1) (hereafter, referred to as "component (B2)") may be used in combination with the component (B1).

As the component (B2), there is no particular limitation as long as it is an acid generator other than the component (B1), and any of the known acid generators used in conventional chemically amplified resist compositions can be used.

Examples of these acid generators are numerous, and include onium salt-based acid generators such as iodonium salts and sulfonium salts; oxime sulfonate-based acid generators; diazomethane-based acid generators such as bisalkyl or bisaryl sulfonyl diazomethanes and poly(bis-sulfonyl)diazomethanes; nitrobenzylsulfonate-based acid generators; iminosulfonate-based acid generators; and disulfone-based acid generators.

As an onium salt-based acid generator a compound represented by general formula (b-1) or (b-2) shown below can be preferably used.

[Chemical Formula 69]

wherein $R^{1\prime\prime}$ to $R^{3\prime\prime}$, $R^{5\prime\prime}$ and $R^{6\prime\prime}$ each independently represents an aryl group or alkyl group, wherein two of $R^{1\prime\prime}$ to $R^{3\prime\prime}$ in formula (b-1) may be bonded to each other to form a ring with the sulfur atom; and $R^{4\prime\prime}$ represents a linear, branched or cyclic alkyl group or fluorinated alkyl group, with the proviso that at least one of $R^{1\prime\prime}$ to $R^{3\prime\prime}$ represents an aryl group, and at least one of $R^{5\prime\prime}$ and $R^{6\prime\prime}$ represents an aryl group.

In general formula (b-1), $R^{1\prime\prime}$ to $R^{3\prime\prime}$ are respectively as defined for $R^{1\prime\prime}$ to $R^{3\prime\prime}$ in general formula (b'-1) above.

$R^{4\prime\prime}$ represents a linear, branched or cyclic alkyl or fluorinated alkyl group.

The linear or branched alkyl group preferably has 1 to 10 carbon atoms, more preferably 1 to 8 carbon atoms, and most preferably 1 to 4 carbon atoms.

The cyclic alkyl group is preferably a cyclic group, as described for $R^{1\prime\prime}$, having 4 to 15 carbon atoms, more preferably 4 to 10 carbon atoms, and most preferably 6 to 10 carbon atoms.

The fluorinated alkyl group preferably has 1 to 10 carbon atoms, more preferably 1 to 8 carbon atoms, and most preferably 1 to 4 carbon atoms. Further, the fluorination ratio of the fluorinated alkyl group (percentage of fluorine atoms within the alkyl group) is preferably from 10 to 100%, more preferably from 50 to 100%, and a fluorinated alkyl group in which all hydrogen atoms are substituted with fluorine atoms (i.e., a perfluoroalkyl group) is particularly desirable because the acid strength increases.

$R^{4\prime\prime}$ is most preferably a linear or cyclic alkyl group or fluorinated alkyl group.

In general formula (b-2), $R^{5\prime\prime}$ and $R^{6\prime\prime}$ are respectively as defined for $R^{5\prime\prime}$ and $R^{6\prime\prime}$ in general formula (b'-2) above.

As $R^{4'''}$ in formula (b-2), the same groups as those for $R^{4'''}$ in formula (b-1) can be mentioned.

Specific examples of suitable onium salt-based acid generators represented by formula (b-1) or (b-2) include diphenyliodonium trifluoromethanesulfonate or nonafluorobutanesulfonate, bis(4-tert-butylphenyl)iodonium trifluoromethanesulfonate or nonafluorobutanesulfonate; triphenylsulfonium trifluoromethanesulfonate, heptafluoropropanesulfonate or nonafluorobutanesulfonate; tri(4-methylphenyl)sulfonium trifluoromethanesulfonate, heptafluoropropanesulfonate or nonafluorobutanesulfonate; dimethyl(4-hydroxynaphthyl)sulfonium trifluoromethanesulfonate, heptafluoropropanesulfonate or nonafluorobutanesulfonate; monophenyldimethylsulfonium trifluoromethanesulfonate, heptafluoropropanesulfonate or nonafluorobutanesulfonate; diphenylmonomethylsulfonium trifluoromethanesulfonate, heptafluoropropanesulfonate or nonafluorobutanesulfonate; (4-methylphenyl)diphenylsulfonium trifluoromethanesulfonate, heptafluoropropanesulfonate or nonafluorobutanesulfonate; (4-methoxyphenyl)diphenylsulfonium trifluoromethanesulfonate, heptafluoropropanesulfonate or nonafluorobutanesulfonate; tri(4-tert-butyl)phenylsulfonium trifluoromethanesulfonate, heptafluoropropanesulfonate or nonafluorobutanesulfonate; diphenyl(1-(4-methoxy)naphthyl)sulfonium trifluoromethanesulfonate, heptafluoropropanesulfonate or nonafluorobutanesulfonate; di(1-naphthyl)phenylsulfonium trifluoromethanesulfonate, heptafluoropropanesulfonate or nonafluorobutanesulfonate; 1-phenyltetrahydrothiophenium trifluoromethanesulfonate, heptafluoropropanesulfonate or nonafluorobutanesulfonate; 1-(4-methylphenyl)tetrahydrothiophenium trifluoromethanesulfonate, heptafluoropropanesulfonate or nonafluorobutanesulfonate; 1-(3,5-dimethyl-4-hydroxyphenyl)tetrahydrothiophenium trifluoromethanesulfonate, heptafluoropropanesulfonate or nonafluorobutanesulfonate; 1-(4-methoxynaphthalene-1-yl)tetrahydrothiophenium trifluoromethanesulfonate, heptafluoropropanesulfonate or nonafluorobutanesulfonate; 1-(4-ethoxynaphthalene-1-yl)tetrahydrothiophenium trifluoromethanesulfonate, heptafluoropropanesulfonate or nonafluorobutanesulfonate; 1-(4-n-butoxynaphthalene-1-yl)tetrahydrothiophenium trifluoromethanesulfonate, heptafluoropropanesulfonate or nonafluorobutanesulfonate; 1-phenyltetrahydrothiopyranium trifluorormethanesulfonate, heptafluoropropanesulfonate or nonafluorobutanesulfonate; 1-(4-hydroxyphenyl)tetrahydrothiopyranium trifluoromethanesulfonate, heptafluoropropanesulfonate or nonafluorobutanesulfonate; 1-(3,5-dimethyl-4-hydroxyphenyl)tetrahydrothiopyranium trifluoromethanesulfonate, heptafluoropropanesulfonate or nonafluorobutanesulfonate; and 1-(4-methylphenyl)tetrahydrothiopyranium trifluoromethanesulfonate, heptafluoropropanesulfonate or nonafluorobutanesulfonate. It is also possible to use onium salts in which the anion moiety of these onium salts are replaced by methanesulfonate, n-propanesulfonate, n-butanesulfonate, or n-octanesulfonate.

Further, onium salt-based acid generators in which the anion moiety in general formula (b-1) or (b-2) is replaced by an anion moiety represented by general formula (b-3) or (b-4) shown below (the cation moiety is the same as (b-1) or (b-2)) may be used.

[Chemical Formula 70]

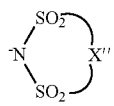
(b-3)

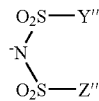
(b-4)

wherein X" represents an alkylene group of 2 to 6 carbon atoms in which at least one hydrogen atom has been substituted with a fluorine atom; and Y" and Z" each independently represents an alkyl group of 1 to 10 carbon atoms in which at least one hydrogen atom has been substituted with a fluorine atom.

X" represents a linear or branched alkylene group in which at least one hydrogen atom has been substituted with a fluorine atom, and the alkylene group has 2 to 6 carbon atoms, preferably 3 to 5 carbon atoms, and most preferably 3 carbon atoms.

Each of Y" and Z" independently represents a linear or branched alkyl group in which at least one hydrogen atom has been substituted with a fluorine atom, and the alkyl group has 1 to 10 carbon atoms, preferably 1 to 7 carbon atoms, and most preferably 1 to 3 carbon atoms.

The smaller the number of carbon atoms of the alkylene group for X" or those of the alkyl group for Y" and Z" within the above-mentioned range of the number of carbon atoms, the more the solubility in a resist solvent is improved.

Further, in the alkylene group for X" or the alkyl group for Y" and Z", it is preferable that the number of hydrogen atoms substituted with fluorine atoms is as large as possible because the acid strength increases and the transparency to high energy radiation of 200 nm or less or electron beam is improved. The amount of fluorine atoms within the alkylene group or alkyl group, i.e., fluorination ratio, is preferably from 70 to 100%, more preferably from 90 to 100%, and it is particularly desirable that the alkylene group or alkyl group be a perfluoroalkylene or perfluoroalkyl group in which all hydrogen atoms are substituted with fluorine atoms.

Further, a sulfonium salt having a cation moiety represented by general formula (b-5) or (b-6) above and an anion moiety other than the anion moiety of the aforementioned component (B1) can be used as an onium salt-based acid generator.

As the anion moiety other than the anion moiety of the aforementioned component (B1), any anion moiety which has been conventionally proposed as an anion moiety for an onium salt-based acid generator can be used. Examples of such anion moieties include fluorinated alkylsulfonic acid ions such as anion moieties ($R^{4'''}SO_3^-$) for onium salt-based acid generators represented by general formula (b-1) or (b-2) shown above; and anion moieties represented by general formula (b-3) or (b-4) shown above.

Among these, a fluorinated alkylsulfonic acid ion is preferable a fluorinated alkylsulfonic acid ion of 1 to 4 carbon atoms is more preferable, and a linear perfluoroalkylsulfonic acid ion of 1 to 4 carbon atoms is particularly desirable. Specific examples include a trifluoromethylsulfonic acid ion, a heptafluoro-n-propylsulfonic acid ion and a nonafluoro-n-butylsulfonic acid ion.

In the present description, an oximesulfonate-based acid generator is a compound having at least one group represented by general formula (B-1) shown below, and has a feature of generating acid by irradiation. Such oximesulfonate-based acid generators are widely used for a chemically amplified resist composition, and can be appropriately selected.

[Chemical Formula 71]

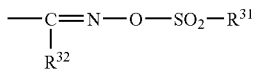
(B-1)

wherein $R^{31}$ and $R^{32}$ each independently represents an organic group.

The organic group for $R^{31}$ and $R^{32}$ refers to a group containing a carbon atom, and may include atoms other than carbon atoms (e.g., a hydrogen atom, an oxygen atom, a nitrogen atom, a sulfa atom, a halogen atom (such as a fluorine atom and a chlorine atom) and the like).

As the organic group for $R^{31}$, a linear, branched, or cyclic alkyl group or aryl group is preferable. The alkyl group or the aryl group may have a substituent. The substituent is not particularly limited, and examples thereof include a fluorine atom and a linear, branched, or cyclic alkyl group having 1 to 6 carbon atoms. The expression "having a substituent" means that some or all of the hydrogen atoms of the alkyl group or the aryl group are substituted with substituents.

The alkyl group preferably has 1 to 20 carbon atoms, more preferably 1 to 10 carbon atoms, still more preferably 1 to 8 carbon atoms, still more preferably 1 to 6 carbon atoms, and most preferably 1 to 4 carbon atoms. As the alkyl group, a partially or completely halogenated alkyl group (hereinafter, sometimes referred to as a "halogenated alkyl groups") is particularly desirable. The "partially halogenated alkyl group" refers to an alkyl group in which some of the hydrogen atoms are substituted with halogen atoms, and the "completely halogenated alkyl group" refers to an alkyl group in which all of the hydrogen atoms are substituted with halogen atoms. Examples of the halogen atom include a fluorine atom, a chlorine atom, a bromine atom and an iodine atom, and a fluorine atom is particularly desirable. In other words, the halogenated alkyl group is preferably a fluorinated alkyl group.

The aryl group preferably has 4 to 20 carbon atoms, more preferably 4 to 10 carbon atoms, and most preferably 6 to 10 carbon atoms. As the aryl group, partially or completely halogenated aryl group is particularly desirable. The "partially halogenated aryl group" refers to an aryl group in which some of the hydrogen atoms are substituted with halogen atoms, and the "completely halogenated aryl group" refers to an aryl group in which all of hydrogen atoms are substituted with halogen atoms.

As $R^{31}$, an alkyl group of 1 to 4 carbon atoms which has no substituent or a fluorinated alkyl group of 1 to 4 carbon atoms is particularly desirable.

As the organic group for $R^{32}$, a linear, branched, or cyclic alkyl group, aryl group, or cyano group is preferable. Examples of the alkyl group and the aryl group for $R^{32}$ are the same as those of the alkyl group and the aryl group for $R^{31}$.

As $R^{32}$, a cyano group, an alkyl group of 1 to 8 carbon atoms having no substituent or a fluorinated alkyl group of 1 to 8 carbon atoms is particularly desirable.

Preferred examples of the oxime sulfonate-based acid generator include compounds represented by general formula (B-2) or (B-3) shown below.

[Chemical Formula 72]

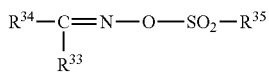
(B-2)

wherein $R^{33}$ represents a cyano group, an alkyl group having no substituent or a halogenated alkyl group; $R^{34}$ represents an aryl group; and $R^{35}$ represents an alkyl group having no substituent or a halogenated alkyl group.

[Chemical Formula 73]

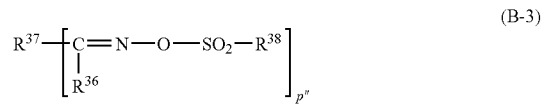
(B-3)

wherein $R^{36}$ represents a cyano group, an alkyl group having no substituent or a halogenated alkyl group; $R^{37}$ represents a divalent or trivalent aromatic hydrocarbon group; $R^{38}$ represents an alkyl group having no substituent or a halogenated alkyl group; and p" represents 2 or 3.

In general formula (B-2), the alkyl group having no substituent or the halogenated alkyl group for $R^{33}$ preferably has 1 to 10 carbon atoms, more preferably 1 to 8 carbon atoms, and most preferably 1 to 6 carbon atoms.

As $R^{33}$, a halogenated alkyl group is preferable, and a fluorinated alkyl group is more preferable.

The fluorinated alkyl group for $R^{33}$ preferably has 50% or more of the hydrogen atoms thereof fluorinated, more preferably 70% or more, and most preferably 90% or more.

Examples of the aryl group for $R^{34}$ include groups in which one hydrogen atom has been removed from an aromatic hydrocarbon ring, such as a phenyl group, a biphenyl group, a fluorenyl group, a naphthyl group, an anthryl group, and a phenantryl group, and heteroaryl groups in which some of the carbon atoms constituting the ring(s) of these groups are substituted with hetero atoms such as an oxygen atom, a sulfur atom, and a nitrogen atom. Of these, a fluorenyl group is preferable.

The aryl group for $R^{34}$ may have a substituent such as an alkyl group of 1 to 10 carbon atoms, a halogenated alkyl group, or an alkoxy group. The alkyl group and halogenated alkyl group as the substituent preferably has 1 to 8 carbon atoms, and more preferably 1 to 4 carbon atoms. The halogenated alkyl group is preferably a fluorinated alkyl group.

The alkyl group having no substituent or the halogenated alkyl group for $R^{35}$ preferably has 1 to 10 carbon atoms, more preferably 1 to 8 carbon atoms, and most preferably 1 to 6 carbon atoms.

As $R^{35}$, a halogenated alkyl group is preferable, and a fluorinated alkyl group is more preferable.

In terms of enhancing the strength of the acid generated, the fluorinated alkyl group for $R^{35}$ preferably has 50% or more of the hydrogen atoms fluorinated, more preferably 70% or more, still more preferably 90% or more. A completely fluorinated alkyl group in which 100% of the hydrogen atoms are substituted with fluorine atoms is particularly desirable.

In general formula (B-3), the alkyl group having no substituent and the halogenated alkyl group for $R^{36}$ are the same as the alkyl group having no substituent and the halogenated alkyl group for $R^{33}$.

Examples of the divalent or trivalent aromatic hydrocarbon group for $R^{37}$ include groups in which one or two hydrogen atoms have been removed from the aryl group for $R^{34}$.

As the alkyl group having no substituent or the halogenated alkyl group for $R^{38}$, the same one as the alkyl group having no substituent or the halogenated alkyl group for $R^{35}$ can be used.

p" is preferably 2.

Specific examples of suitable oxime sulfonate-based acid generators include
α-p-toluenesulfonyloxyimino)-benzyl cyanide,
α-p-chlorobenzenesulfonyloxyimino)-bezyl cyanide,
α-(4-nitrobenzenesulfonyloxyimino)-benzyl cyanide,
α-(4-nitro-2-trifluoromethylbenzenesulfonyloxyimino)-benzyl cyanide,
α-(benzenesulfonyloxyimino)-4-chlorobenzyl cyanide,
α-(benzenesulfonyloxyimino)-2,4-dichlorobenzyl cyanide,
α-(benzenesulfonyloxyimino)-2,6-dichlorobenzyl cyanide,
α-(benzenesulfonyloxyimino)-4-methoxybenzyl cyanide,
α-(2-chlorobenzenesulfonyloxyimino)-4-methoxybenzyl cyanide,
α-(benzenesulfonyloxyimino)-thien-2-yl acetonitrile,
α-(4-dodecylbenzenesulfonytoxyimino)benzyl cyanide,
α-[(p-toluenesulfonyloxyimino)-4-methoxyphenyl]acetonitrile,
α-[(dodecylbenzenesulfonyloxyimino)-4-methoxyphenyl] acetonitrile,
α-(tosyloxyimino)-4-thienyl cyanide, α-(methylsulfonyloxyimino)-1-cyclopentenyl acetonitrile, α-(methylsulfonyloxyimino)-1-cyclohexenyl acetonitrile,
α-(methylsulfonyloxyimino)-1-cycloheptenyl acetonitrile,
α-(methylsulfonyloxyimino)-1-cyclooctenyl acetonitrile,
α-(trifluoromethylsulfonyloxyimino)-1-cyclopentenyl acetonitrile,
α-(trifluoromethylsulfonyloxyimino)-cyclohexyl acetonitrile,
α-(ethylsulfonyloxyimnino)-ethyl acetonitrile, α-(propylsulfonyloxyimino)-propyl acetonitrile, α-(cyclohexylsulfonyloxyimino)-cyclopentyl acetonitrile,
α-(cyclohexylsulfonyloxyimino)-cyclohexyl acetonitrile,
α-(cyclohexylsulfonyloxyimino)-1-cyclopentenyl acetonitrile,
α-(ethylsulfonyloxyimino)-1-cyclopentenyl acetonitrile,
α-(isopropylsulfonyloxyimino)-1-cyclopentenyl acetonitrile,
α-(n-butylsulfonyloxyimino)-1-cyclopentenyl acetonitrile,
α-(ethylsulfonyloxyimino)-1-cyclohexenyl acetonitrile,
α-(isopropylsulfonyloxyimino)-1-cyclohexenyl acetonitrile,
α-(n-butylsulfonyloxyimino)-1-cyclohexenyl acetonitrile,
α-(methylsulfonyloxyimino)-phenyl acetonitrile,
α-(methylsulfonyloxyimino)-p-methoxyphenyl acetonitrile,
α-(trifluoromethylsulfonyloxyimino)-phenyl acetonitrile,
α-(trifluoromethylsulfonyloxyimino)-p-methoxyphenyl acetonitrile,
α-(ethylsulfonyloxyimino)-p-methoxyphenyl acetonitrile,
α-(propylsulfonyloxyimino)-p-methylphenyl acetonitrile, and
α-(methylsulfonyloxyimino)-p-bromophenyl acetonitrile.

Further, oxime sulfonate-based acid generators disclosed in Japanese Unexamined Patent Application, First Publication No. Hei 9-208554 (Chemical Formulas 18 and 19 shown in paragraphs [0012] to [0014]) and oxime sulfonate-based acid generators disclosed in WO 2004/074242A2 (Examples 1 to 40 described at pages 65 to 85) may be preferably used.

Furthermore, as preferable examples, the following can be mentioned.

[Chemical Formula 74]

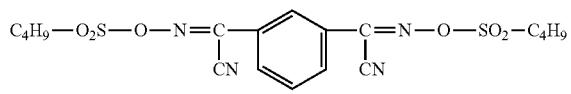

-continued

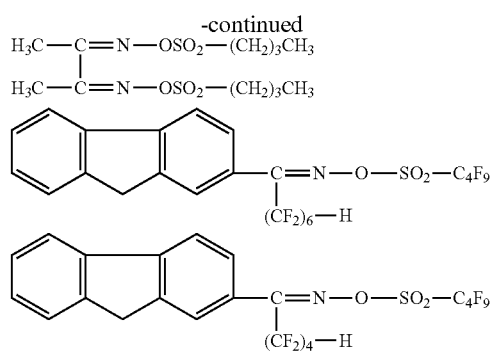

Of the aforementioned diazomethane-based acid generators, specific examples of suitable bisalkyl or bisaryl salfonyl diazomethanes include bis(isopropylsulfonyl)diazomethane, bis(p-toluenesulfonyl)diazomethane, bis(1,1-dimethylethylsulfonyl)diazomethane, bis(cyclohexylsulfonyl)diazomethane, and bis(2,4-dimethylphenylsulfonyl)diazomethane.

Further, diazomethane-based acid generators disclosed in Japanese Unexamined Patent Application, First Publication No. Hei 11-035551, Japanese Unexamined Patent Application, First Publication No. Hei 11-035552 and Japanese Unexamined Patent Application, First Publication No. Hei 11-035573 may be preferably used.

Furthermore, as poly(bis-sulfonyl)diazomethanes, those disclosed in Japanese Unexamined Patent Application, First Publication No. Hei 11-322707, including
1,3-bis(phenylsulfonyldiazomethylsulfonyl)propane,
1,4-bis(phenylsulfonyldiazomethylsulfonyl)butane,
1,6-bis(phenylsulfonyldiazomethylsulfonyl)hexane,
1,10-bis(phenylsulfonyldiazomethylsulfonyl)decane,
1,2-bis(cyclohexylsulfonyldiazomethylsulfonyl)ethane,
1,3-bis(cyclohexylsulfonyldiazomethylsulfonyl)propane,
1,6-bis(cyclohexylsulfonyldiazomethylsulfonyl)hexane, and
1,10-bis(cyclohexylsulfonyldiazomethylsulfonyl)decane,
may be mentioned.

As the component (B2), one type of acid generator may be used, or two or more types may be used in combination.

The total amount of the component (B) within the resist composition of the present invention is typically 0.5 to 30 parts by weight, and preferably 1 to 20 parts by weight, relative to 100 parts by weight of the component (A). When the amount of the component (B) is within the above-mentioned range, formation of a resist pattern can be satisfactorily performed. Further, by virtue of the above-mentioned range, a uniform solution can be obtained and the storage stability becomes satisfactory.

<Optional Components>

In the resist composition of the present invention, for improving the resist pattern shape and the post exposure stability of the latent image formed by the pattern-wise exposure of the resist layer, it is preferable to add a nitrogen-containing organic compound (D) (hereafter referred to as the component (D)).

A multitude of these components (D) have already been proposed, and any of these known compounds may be used, although an aliphatic amine, and particularly a secondary aliphatic amine or tertiary aliphatic amine is preferable. An aliphatic amine is an amine having one or more aliphatic groups, and the aliphatic groups preferably have 1 to 12 carbon atoms.

Examples of these aliphatic amines include amines in which at least one hydrogen atom of ammonia ($NH_3$) has been substituted with an alkyl group or hydroxyalkyl group of no more than 12 carbon atoms (i.e., alkylamines or alkylalcoholamines), and cyclic amines.

Specific examples of alkylamines and alkylalcoholamines include monoalkylamines such as n-hexylamine, n-heptylamine, n-octylamine, n-nonylamine, and n-decylamine; dialkylamines such as diethylamine, di-n-propylamine, di-n-heptylamine, di-n-octylamine, and dicyclohexylamine; trialkylamines such as trimethylamine, triethylamine, tri-n-propylamine, tri-n-butylamine, tri-n-hexylamine, tri-n-pentylamine, tri-n-heptylamine, tri-n-octylamine, tri-n-nonylamine, tri-n-decanylamine, and tri-n-dodecylamine; and alkyl alcohol amines such as diethanolamine, triethanolamine, diisopropanolamine, triisopropanolamine, di-n-octanolamine, and tri-n-octanolamine. Among these, trialkylamines in which three alkyl groups of 5 to 10 carbon atoms are bonded to the nitrogen atom are preferable, and tri-n-pentylamine is particularly desirable.

Examples of the cyclic amine include heterocyclic compounds containing a nitrogen atom as a hetero atom. The heterocyclic compound may be a monocyclic compound (aliphatic monocyclic amine), or a polycyclic compound (aliphatic polycyclic amine).

Specific examples of the aliphatic monocyclic amine include piperidine, and piperazine.

The aliphatic polycyclic amine preferably has 6 to 10 carbon atoms, and specific examples thereof include 1,5-diazabicyclo[4.3.0]-5-nonene, 1,8-diazabicyclo[5.4.0]-7-undecene, hexamethylenetetramine, and 1,4-diazabicyclo[2.2.2]octane.

Apart from the nitrogen-containing organic compounds mentioned above, stearyldiethanolamine can also be preferably used.

These compounds can be used either alone, or in combinations of two or more different compounds.

The component (D) is typically used in an amount within a range from 0.01 to 5.0 parts by weight, relative to 100 parts by weight of the component (A).

Furthermore, in the resist composition of the present invention, for preventing any deterioration in sensitivity, and improving the resist pattern shape and the post exposure stability of the latent image formed by the pattern-wise exposure of the resist layer, at least one compound (E) (hereafter referred to as the component (B)) selected from the group consisting of an organic carboxylic acid, or a phosphorus oxo acid or derivative thereof can be added.

Examples of suitable organic carboxylic acids include acetic acid, malonic acid, citric acid, malic acid, succinic acid, benzoic acid, and salicylic acid.

Examples of phosphorus oxo acids or derivatives thereof include phosphoric acid, phosphonic acid and phosphinic acid. Among these, phosphonic acid is particularly desirable.

Examples of oxo acid derivatives include esters in which a hydrogen atom within the above-mentioned oxo acids is substituted with a hydrocarbon group. Examples of the hydrocarbon group include an alkyl group of 1 to 5 carbon atoms and an aryl group of 6 to 15 carbon atoms.

Examples of phosphoric acid derivatives include phosphoric acid esters such as di-n-butyl phosphate and diphenyl phosphate.

Examples of phosphonic acid derivatives include phosphonic acid esters such as dimethyl phosphonate, di-n-butyl phosphonate, phenylphosphonic acid, diphenl phosphonate and dibenzyl phosphonate.

Examples of phosphinic acid derivatives include phosphinic acid esters such as phenylphosphinic acid.

As the component (E), one type may be used alone, or two or more types may be used in combination.

As the component (E), an organic carboxylic acid is preferable, and salicylic acid is particularly desirable.

The component (E) is typically used in an amount within a range from 0.01 to 5.0 parts by weight, relative to 100 parts by weight of the component (A).

If desired, other miscible additives can also be added to the resist composition of the present invention. Examples of such miscible additives include additive resins for improving the performance of the resist film, surfactants for improving the applicability, dissolution inhibitors, plasticizers, stabilizers, colorants, halation prevention agents, and dyes.

[Component (S)]

The resist composition of the present invention can be prepared by dissolving the materials for the resist composition in an organic solvent (S) (hereafter, frequently referred to as "component (S)").

The component (S) may be any organic solvent which can dissolve the respective components to give a uniform solution, and any one or more kinds of organic solvents can be appropriately selected from those which have been conventionally known as solvents for a chemically amplified resist.

Examples thereof include lactones such as γ-butyrolactone; ketones such as acetone, methyl ethyl ketone, cyclohexanone, methyl-n-pentyl ketone, methyl isopentyl ketone, and 2-heptanone; polyhydric alcohols, such as ethylene glycol, diethylene glycol, propylene glycol and dipropylene glycol; compounds having an ester bond, such as ethylene glycol monoacetate, diethylene glycol monoacetate, propylene glycol monoacetate, and dipropylene glycol monoacetate; polyhydric alcohol derivatives including compounds having an ether bond, such as a monoalkylether (e.g., monomethylether, monoethylether, monopropylether or monobutylether) or monophenylether of any of these polyhydric alcohols or compounds having an ester bond (among these, propylene glycol monomethyl ether acetate (PGMEA) and propylene glycol monomethyl ether (PGME) are preferable); cyclic ethers such as dioxane; esters such as methyl lactate, ethyl lactate (EL), methyl acetate, ethyl acetate, butyl acetate, methyl pyruvate, ethyl pyruvate, methyl methoxypropionate, and ethyl ethoxypropionate; and aromatic organic solvents such as anisole, ethylbenzylether, cresylmethylether, diphenylether, dibenzylether, phenetole, butylphenylether, ethylbenzene, diethylbenzene, pentylbenzene, isopropylbenzene, toluene, xylene, cymene and mesitylene.

These solvents can be used individually, or in combination as a mixed solvent.

Among these, propylene glycol monomethyl ether acetate (PGMEA), propylene glycol monomethyl ether (PGME), and ethyl lactate (EL) are preferable.

Further, among the mixed solvents, a mixed solvent obtained by mixing PGMEA with a polar solvent is preferable. The mixing ratio (weight ratio) of the mixed solvent can be appropriately determined, taking into consideration the compatibility of the PGMEA with the polar solvent, but is preferably in the range of 1:9 to 9:1, more preferably from 2:8 to 8:2.

Specifically, when EL is mixed as the polar solvent, the PGMEA:EL weight ratio is preferably from 1:9 to 9:1, and more preferably from 2:8 to 8:2. Alternatively, when PGME is mixed as the polar solvent, the PGMEA:PGME is preferably from 1:9 to 9:1, more preferably from 2:8 to 8:2, and still more preferably 3:7 to 7:3.

Further, as the component (S), a mixed solvent of at least one of PGMEA and EL with γ-butyrolactone is also preferable. The mixing ratio (former:latter) of such a mixed solvent is preferably from 70:30 to 95:5.

The amount of the organic solvent is not particularly limited, and is appropriately adjusted to a concentration which enables coating of a coating solution to a substrate, depending on the thickness of the coating film. In general, the organic solvent is used in an amount such that the solid content of the resist composition becomes within the range from 2 to 20% by weight, and preferably from 5 to 15% by weight.

The resist composition of the present invention is novel, and was conventionally uknown.

As the resist composition of the present invention contains the compound (b1-1) of the present invention as an acid generator, various lithography properties are improved. For example, when a resist pattern is formed from such a resist composition, resolution, mask reproducibility (e.g., mask linearity or the like), exposure margin (EL margin), pattern shape, depth of focus (DOF), and the like are improved.

The EL margin is the range of the exposure dose at which a resist pattern can be formed with a size within a predetermined range of variation from a target size, when exposure is conducted by changing the exposure dose, i.e., the range of the exposure dose at which a resist pattern faithful to the mask pattern can be formed. The larger the exposure margin, the smaller the variation in the pattern size depending on the change in the exposure dose, thereby resulting in favorable improvement in the process margin.

The reason why the aforementioned effects can be achieved is presumed as follows. The compound (b1-1) has a structure in which the skeleton "$Y^1$—$SO_3^-$" within the anion moiety has $R^x$-$Q^3$-O-$Q^2$- bonded thereto. As a result, the anion moiety of such a component exhibits a high polarity and has a three-dimensionally bulky structure, as compared to a fluorinated alkylsulfonic ion which has been conventionally used as an anion moiety. By virtue of the intermolecular force due to the high polarity, and the three-dimensionally bulky structure, it is presumed that diffusion of the anion moiety within the resist film is chemically and physically suppressed, as compared to the anion moiety of a conventional acid generator such as nonafluorobutanesulfonate. Therefore, by using such a compound, diffusion of the acid generated in the exposed regions to the unexposed regions can be suppressed, and hence, the difference in alkali solubility between the exposed regions and the unexposed regions (i.e., dissolution contrast) can be improved, and it is presumed that resolution and resist pattern shapes can be improved.

Furthermore, the alkyl chain of the alkylene group or fluorinated alkyl group for $Y^1$ which may have a substituent exhibits an excellent decomposability, as compared to, for example, a perfluoroalkyl chain of 6 to 10 carbon atoms. Therefore, the effect of minimizing bioaccumulation to improve ease of handling can be achieved.

<<Method of Forming a Resist Pattern>>

The method of forming a resist pattern according to the second aspect of the present invention includes: applying a resist composition according to the first aspect of the present invention to a substrate to form a resist film on the substrate; conducting exposure of the resist film; and alkali-developing the resist film to form a resist pattern.

More specifically, the method for forming a resist pattern according to the present invention can be performed, for example, as follows. Firstly, a resist composition of the present invention is applied onto a substrate using a spinner or the like, and a prebake (post applied bake (PAB)) is conducted under temperature conditions of 80 to 150° C. for 40 to 120 seconds, preferably 60 to 90 seconds to form a resist film. Then, for example, using an ArF exposure apparatus or the likes the resist film is selectively exposed to an ArF excimer laser beam through a desired mask pattern, followed by post exposure bake (PEB) under temperature conditions of 80 to 150° C. for 40 to 120 seconds, preferably 60 to 90 seconds. Subsequently, alkali developing is conducted using an alkali developing solution such as a 0.1 to 10% by weight aqueous solution of tetramethylammonium hydroxide (TMAH), preferably followed by rinsing with pure water, and drying. If desired, bake treatment (post bake) can be conducted following the alkali developing. In this manner, a resist pattern that is faithful to the mask pattern can be obtained.

The substrate is not specifically limited and a conventionally known substrate can be used. For example, substrates for electronic components, and such substrates having wiring patterns formed thereon can be mentioned. Specific examples of the material of the substrate include metals such as silicon wafer, copper, chromium iron and aluminum; and glass. Suitable materials for the wiring pattern include copper, aluminum, nickel, and gold.

Further, as the substrate, any one of the above-mentioned substrates provided with an inorganic and/or organic film on the surface thereof may be used. As the inorganic film, an inorganic antireflection film (inorganic BARC) can be mentioned. As the organic films an organic antireflection film (organic BARC) can be mentioned.

The wavelength to be used for exposure is not particularly limited and the exposure can be conducted using radiations such as ArF excimer laser, KrF excimer laser, $F_2$ excimer laser, extreme ultraviolet rays (EUV), vacuum ultraviolet rays (VUV), electron beam (EB), X-rays, and soft X-rays. The positive resist composition of the present invention is effective to KrF excimer laser, ArF excimer laser, EB and EUV, and particularly effective to ArF excimer laser.

The exposure of the resist film can be either a general exposure (dry exposure) conducted in air or an inert gas such as nitrogen, or immersion exposure (immersion lithography).

In immersion lithography, exposure (immersion exposure) is conducted in a state where the region between the lens and the resist layer formed on a wafer (which was conventionally filled with air or an inert gas such as nitrogen) is filled with a solvent (a immersion medium) that has a larger refractive index than the refractive index of air.

More specifically, in immersion lithography, the region between the resist film formed in the above-described manner and lens at the lowermost portion of the exposure apparatus is filled with a solvent (a immersion medium) that has a larger refractive index than the refractive index of air, and in this state, the resist film is subjected to exposure (immersion exposure) through a desired mask pattern.

The immersion medium preferably exhibits a refractive index larger than the refractive index of air but smaller than the refractive index of the resist film to be subjected to immersion exposure. The refractive index of the immersion medium is not particularly limited as long at it satisfies the above-mentioned requirements.

Examples of this immersion medium which exhibits a refractive index that is larger than the refractive index of air but smaller than the refractive index of the resist film include water, fluorine-based inert liquids, silicon-based solvents and hydrocarbon-based solvents.

Specific examples of the fluorine-based inert liquids include liquids containing a fluorine-based compound such as $C_3HCl_2F_5$, $C_4F_9OCH_3$, $C_4F_9OC_2H_5$ or $C_5H_3F_7$ as the main component which have a boiling point within a range from 70 to 180° C. and preferably from 80 to 160° C. A fluorine-based inert liquid having a boiling point within the above-mentioned range is advantageous in that the removal of the immersion medium after the exposure can be conducted by a simple method.

As a fluorine-based inert liquid, a perfluoroalkyl compound in which all of the hydrogen atoms of the alkyl group are substituted with fluorine atoms is particularly desirable. Examples of these perfluoroalkyl compounds include perfluoroalkylether compounds and perfluoroalkylamine compounds.

Specifically, one example of a suitable perfluoroalkylether compound is perfluoro(2-butyl-tetrahydrofuran) (boiling point 102° C.), and an example of a suitable perfluoroalkylamine compound is perfluorotributylamine (boiling point 174° C.).

EXAMPLES

As follows is a description of examples of the present invention, although the scope of the present invention is by no way limited by these examples.

In the following examples, compounds represented by chemical formulas are designated as corresponding compounds, for example, a compound represented by chemical formula (II) is designated as "compound (II)".

Synthesis Example 1

4.34 g of a compound (II) (purity: 94.1%), 3.14 g of 2-benzyloxyethanol and 43.4 g of toluene were prepared, 0.47 g of p-toluenesulfonic acid hydrate was added thereto, and the resultant was refluxed at 105° C. for 20 hours. Then, the reaction liquid was filtered, and 20 g of hexane was added to the residue and stirred. Thereafter, the resultant was filtered, and the residue was dried, thereby obtaining 1.41 g of a compound (III) (yield: 43.1%).

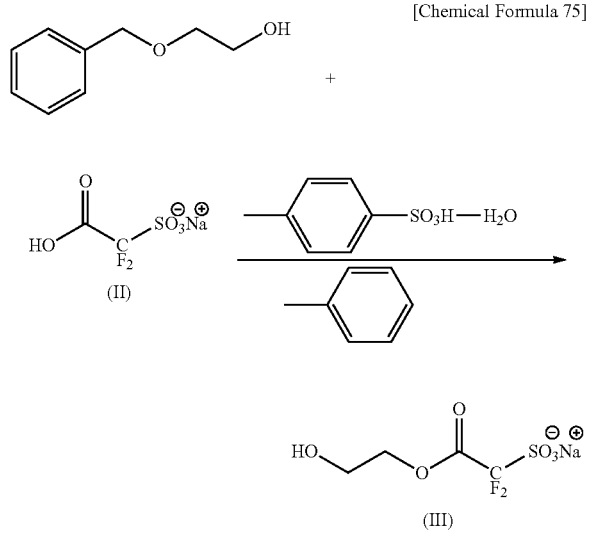

The obtained compound (III) was analyzed by NMR.

$^1$H-NMR(DMSO-d6, 400 MHz): δ(ppm)=4.74-4.83 (t, 1H,OH), 4.18-4.22 (t, 2H,H$^a$), 3.59-3.64 (q, 2H,H$^b$).

$^{19}$F-NMR(DMSO-d6, 376 MHz): δ(ppm)=−106.6.

From the results above, it was confirmed that the compound (III) had a structure shown below.

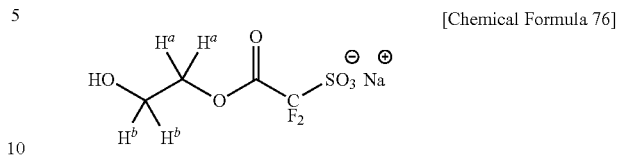

Example 1

To 1.00 g of the compound (III) and 3.00 g of acetonitrile were dropwise added 0.82 g of 1-adamantanecarbonyl chloride and 0.397 g of triethylamine while cooling with ice. Then, the resultant was stirred at room temperature for 20 hours, followed by filtration. The filtrate was concentrated and dried, and dissolved in 30 g of dichloromethane, followed by washing with water three times. Thereafter, the organic phase was concentrated and dried, thereby obtaining 0.82 g of a compound (IV) (yield: 41%).

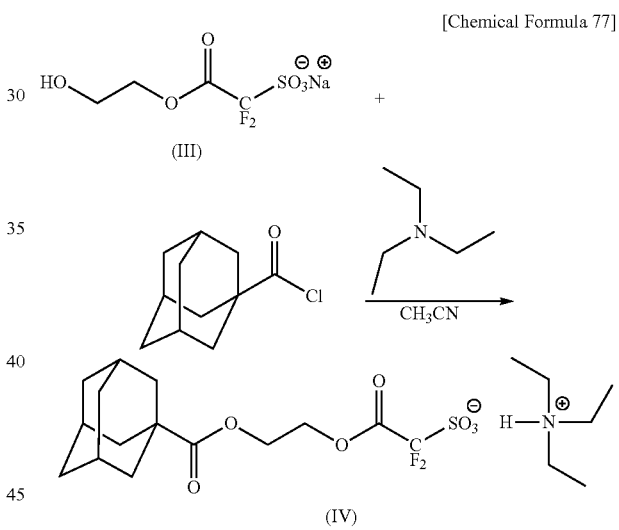

The obtained compound (IV) was analyzed by NMR.

$^1$H-NMR(DMSO-d6, 400 MHz): δ(ppm)=8.81 (s, 1H,H$^c$), 4.37-4.44 (t, 2H,H$^d$), 4.17-4.26 (t, 2H,H$^e$), 3.03-3.15 (q, 6H,H$^b$), 1.61-1.98 (m, 15H,Adamantane), 1.10-1.24 (t, 9H,H$^a$).

$^{19}$F-NMR(DMSO-d6, 376 MHz): δ(ppm)=−106.6.

From the results above, it was confirmed that the compound (IV) had a structure shown below.

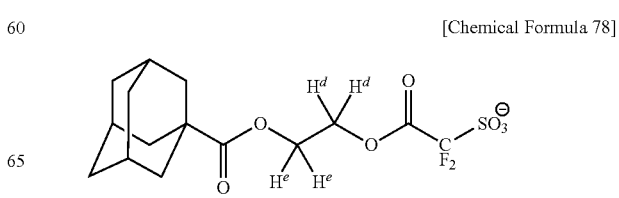

-continued

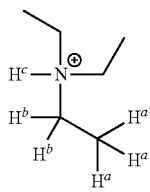

Example 2

4.34 g of a compound (II) (purity: 94.1%), 3.14 g of 2-benzyloxyethanol and 43.4 g of toluene were prepared, 0.47 g of p-toluenesulfonic acid hydrate was added thereto, and the resultant was refluxed at 105° C. for 20 hours. Then, the reaction liquid was cooled, and 3.18 g of triethylamine hydrochloride was added thereto and stirred at room temperature for 3 hours. Thereafter, 31.4 g of dichloromethane was added to the reaction liquid, followed by filtration. The filtrate was concentrated and dried, thereby obtaining 1.31 g of a compound (VII) (yield: 19.8%).

[Chemical Formula 79]

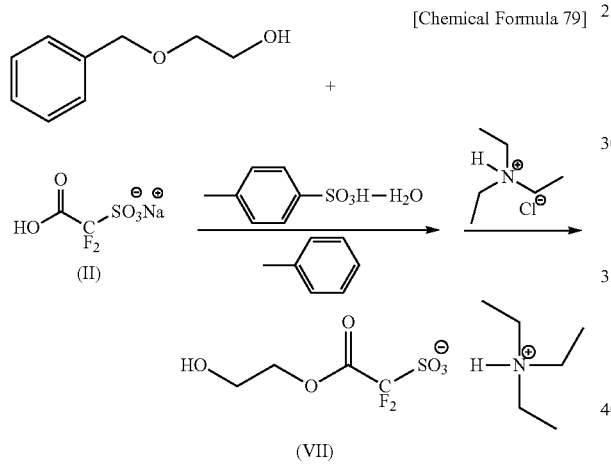

The obtained compound (VII) was analyzed by NMR.
$^1$H-NMR(DMSO-d6, 400 MHz): δ(ppm)=9.20 (s, 1H,$H^c$), 4.80 (s, 1H,$H^f$), 4.19-4.21 (t, 2H,$H^d$), 3.58-3.59 (m, 2H,$H^e$), 3.04-3.10 (q, 6H,$H^b$), 1.13-1.21 (t, 9H,$H^a$).
$^{19}$F-NMR(DMSO-d6, 376 MHz): δ(ppm)=−106.7.

From the results above, it was confirmed that the compound (VII) had a structure shown below.

[Chemical Formula 80]

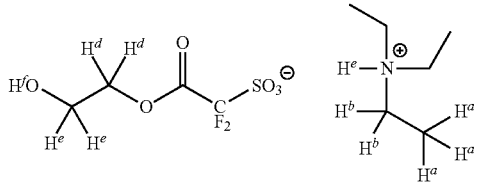

Example 3

To 1.33 g of the compound (VII) and 3.00 g of acetonitrile were dropwise added 0.82 g of 1-adamantanecarbonyl chloride and 0.397 g of triethylamine while cooling with ice. Then, the resultant was stirred at room temperature for 20 hours, followed by filtration. The filtrate was concentrated and dried, and dissolved in 30 g of dichloromethane, followed by washing with water three times. Thereafter, the organic phase was concentrated and dried, thereby obtaining 0.86 g of a compound (IV') (yield: 43.1%).

[Chemical Formula 81]

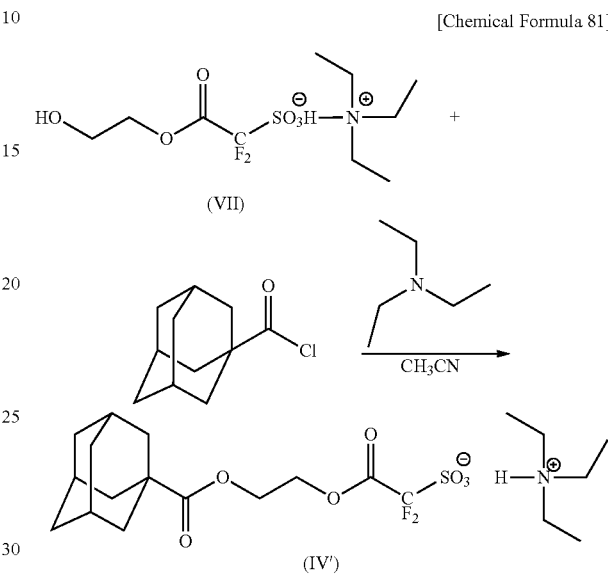

The obtained compound (IV') was analyzed by NMR. As a result, the same spectra as that obtained in Example 1 for the compound (IV) was obtained.

Example 4

0.384 g of a compound (V) was dissolved in 3.84 g of dichloromethane and 3.84 g of water, and 0.40 g of the compound (IV) was added thereto. The resultant was stirred for 1 hour, followed by liquid separation to collect the organic phase. The organic phase was washed with 3.84 g of water three times. Thereafter, the resulting organic phase was concentrated and dried, thereby obtaining 0.44 g of a compound (VI) (yield: 81.5%).

[Chemical Formula 82]

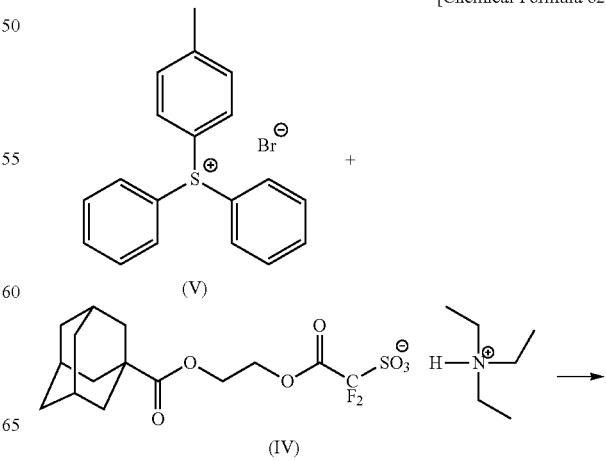

121

-continued (VI)

The obtained compound (VI) was analyzed by NMR.

$^1$H-NMR(DMSO-d6, 400 MHz): δ(ppm)=7.57-7.87 (m, 14H,Phenyl), 4.40-4.42 (t, 2H,H$^b$), 4.15-4.22 (t, 2H,H$^a$), 2.43 (s, 3H,H$^c$), 1.60-1.93 (m, 15H,Adamantane).

$^{19}$F-NMR(DMSO-d6, 376 MHz): δ(ppm)=−106.7.

From the results above, it was confirmed that the compound (VI) had a structure shown below.

[Chemical Formula 83]

Example 5

(i)

To 60.75 g of methanesulfonic acid controlled to 20° C. or lower was added 8.53 g of phosphorus oxide, 8.81 g of 2,5-dimethylphenol and 12.2 g of diphenylsulfoxide in small amounts. The resultant was matured for 30 minutes while maintaining the temperature at 15 to 20° C., followed by elevating the temperature to 40° C. and maturing for 2 hours. Then, the reaction liquid was dropwise added to 109.35 g of pure water cooled to 15° C. or lower. Thereafter, 54.68 g of dichloromethane was added and stirred, and the dichloromethane phase was collected. 386.86 g of hexane at a temperature of 20 to 25° C. was charged into a separate vessel, and the dichloromethane phase was dropwise added thereto. Then, the resultant was matured at 20 to 25° C. for 30 minutes, followed by filtration, thereby obtaining 17.14 g of an objective compound (i) (yield: 70.9%).

The obtained compound (i) was analyzed by NMR.

$^1$H-NMR(DMSO-d6, 600 MHz): δ(ppm)=7.61-7.72 (m, 10H,phenyl), 7.14 (s, 2H,H$^c$), 3.12 (s, 3H,H$^b$), 2.22 (s, 6H,H$^a$).

122

From the results shown above, it was confirmed that the compound (i) had a structure shown below.

[Chemical Formula 84]

(ii)

4 g of the compound (i) was dissolved in 79.8 g of dichloromethane. After confirming that the compound (i) had dissolved in dichloromethane, 6.87 g of potassium carbonate was added thereto, and 3.42 g of bromoacetic acid methyl adamantane was further added. A reaction was effected under reflux for 24 hours, followed by filtration, washing with water, and crystallization with hexane. The resulting powder was dried under reduced pressure, thereby obtaining 3.98 g of an objective compound (ii) (yield: 66%).

The obtained compound (ii) was analyzed by NMR.

$^1$H-NMR(CDCl$_3$, 400 MHz): δ(ppm)=7.83-7.86 (m, 4H,Phenyl), 7.69-7.78 (m, 6H,Phenyl), 7.51 (s, 2H,H$^d$), 4.46 (s, 2H,H$^c$), 2.39 (s, 6H,H$^a$), 2.33 (s, 2H,Adamantane), 2.17 (s, 2H,Adamantane), 1.71-1.976 (m, 11H,Adamantane), 1.68 (s, 3H,H$^b$), 1.57-1.61 (m, 2H,Adamantane).

From the results shown above, it was confirmed that the compound (ii) had a structure shown below.

[Chemical Formula 85]

(iii)

4.77 g of the compound (ii) was dissolved in 23.83 g of dichloromethane and 23.83 g of water, and 3.22 g of the compound (IV) was added thereto. The resultant was stirred for 1 hour, followed by liquid separation to collect the organic phase. The organic phase was washed with 3.84 g of water three times. Thereafter, the resulting organic phase was concentrated and dried, thereby obtaining 4.98 g of a compound (X) (yield: 87%).

[Chemical Formula 86]

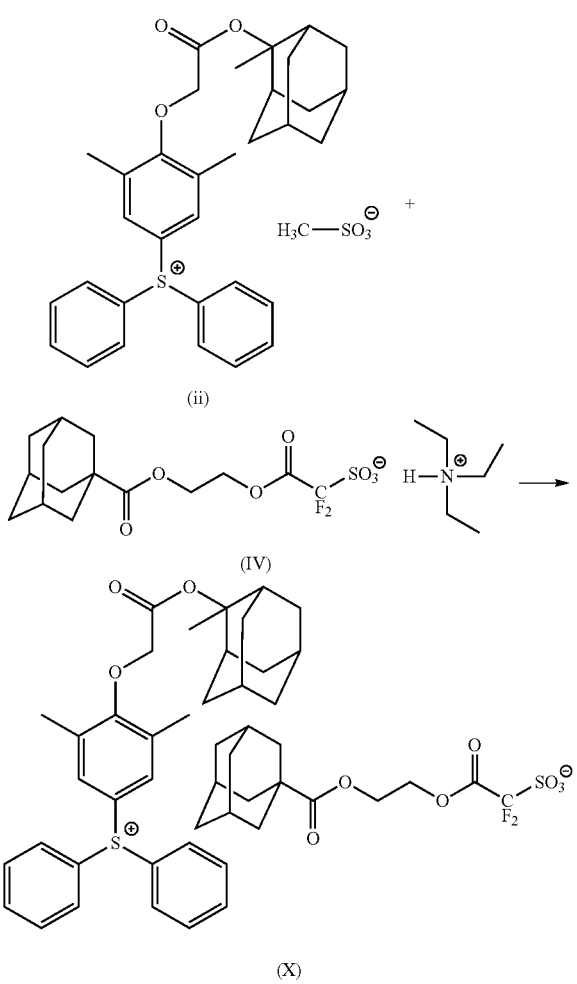

The obtained compound (X) was analyzed by NMR.
$^1$H-NMR(DMSO-d6, 400 MHz): δ(ppm)=7.76-7.88 (m, 10H,Phenyl), 7.62 (s, 2H,Phenyl), 4.64 (s, 2H,H$^b$), 4.43-4.44 (t, 2H,H$^c$), 4.22-4.23 (t, 2H,H$^d$), 1.51-2.36 (m, 38H,Adamantane+H$^a$+H$^e$).
$^{19}$F-NMR(DMSO-d6, 376 MHz): δ(ppm)=−106.7.
From the results above, it was confirmed that the compound (X) had a structure shown below.

[Chemical Formula 87]

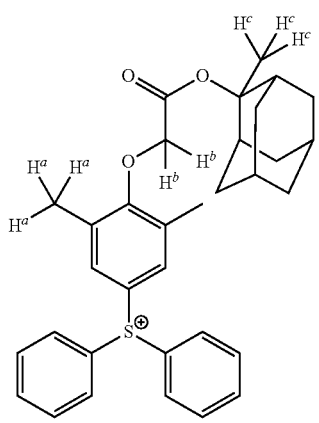

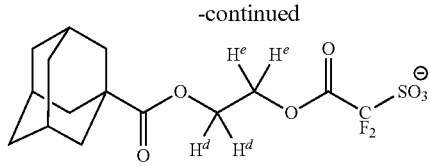

Example 6

1.99 g of triethylamine hydrochloride and 25.00 g of acetonitrile were charged into a reaction vessel, and 5.00 g of a compound (VIII) was added thereto. The content of the reaction vessel was stirred at room temperature for 15 hours. Then, the reaction liquid was subjected to filtration, and the solvent was distilled off the filtrate under reduced pressure. The resultant was dissolved in dichloromethane (29 g), followed by washing with pure water (5.8 g) twice. Thereafter, the organic phase was separated, and the organic phase was dropwise added to hexane (435 g), thereby obtaining 1.2 g of an objective compound (IX) (yield: 20%).

[Chemical Formula 88]

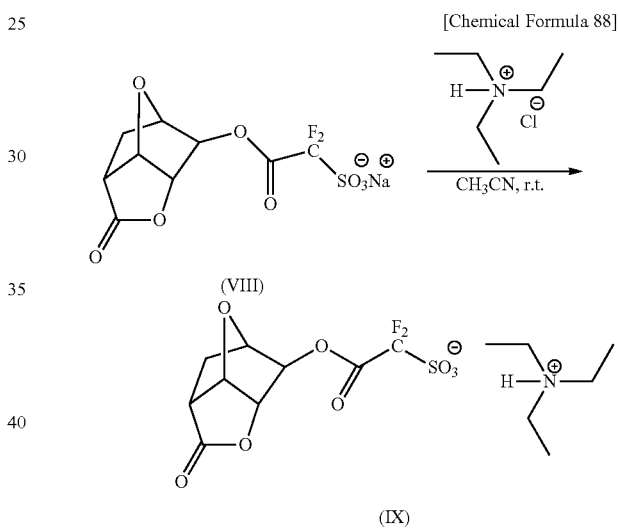

The obtained compound (IX) was analyzed by NMR.
$^1$H-NMR(DMSO-d6, 400 MHz): δ(ppm)=8.81 (brs, 1H,NH), 5.46 (t, 1H,oxo-norbornene), 4.97 (s, 1H,oxo-norbornene), 4.71 (d, 1H,oxo-norbornene), 4.57 (d, 1H,oxo-norbornene), 3.09 (q, 6H,NCH$_2$), 2.69-2.73 (m, 1H,oxo-norbornene), 2.06-2.16 (m, 2H,oxo-norbornene), 1.15 (t, 9H,CH$_3$),
$^{19}$F-NMR(DMSO-d6, 376 MHz): δ(ppm)=−107.1.
From the results above, it was confirmed that the compound (IX) had a structure shown above.

Example 7

To 2.42 g of the compound (III) and 7.26 g of acetonitrile were dropwise added 2.19 g of undecanoylcarbonyl chloride and 1.01 g of triethylamine while cooling with ice. Then, the resultant was stirred at room temperature for 20 hours, followed by filtration. The filtrate was concentrated and dried, and dissolved in 20 g of dichloromethane, followed by washing with water three times. Thereafter, the organic phase was concentrated and dried, thereby obtaining 3.41 g of a compound (XI) (yield: 80.4%).

[Chemical Formula 89]

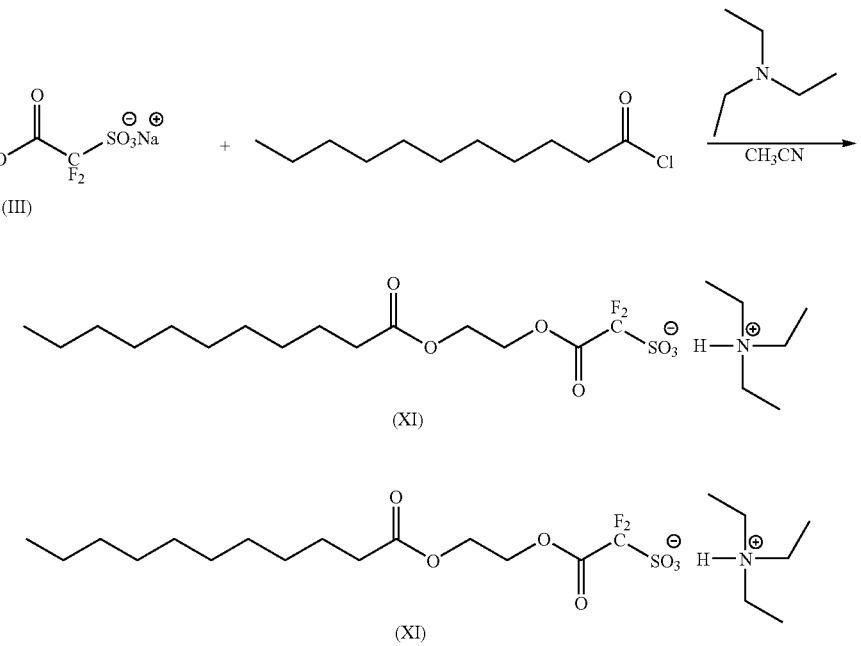

The obtained compound (XI) was analyzed by NMR.
$^1$H-NMR(DMSO-d6, 400 MHz): δ(ppm)=8.81 (s, 1H,H$^f$), 4.39-4.41 (t, 2H,H$^d$), 4.23-4.39 (t, 2H,H$^e$), 3.06-3.10 (q, 6H,H$^h$), 2.24-2.29 (t, 2H,H$^c$), 1.09-1.51 (m, 25H,H$^b$+H$^g$), 0.83-0.89 (t, 3H,H$^a$).
$^{19}$F-NMR(DMSO-d6, 376 MHz): δ(ppm)=−106.8.

From the results above, it was confirmed that the compound (XI) had a structure shown below.

[Chemical Formula 90]

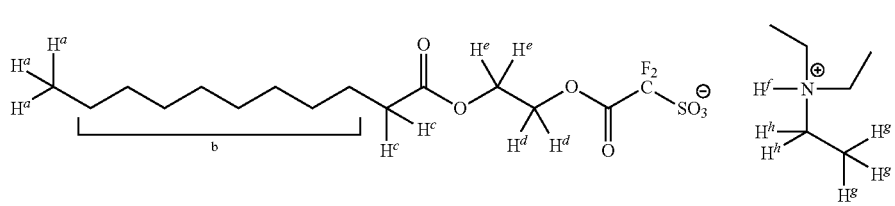

Example 8

1.68 g of a compound (XII') was dissolved in 8.41 g of dichloromethane and 8.41 g of water, and 2.00 g of the compound (XI) was added thereto. The resultant was stirred for 1 hour, followed by liquid separation to collect the organic phase. The organic phase was washed with 3.84 g of water three times. Thereafter, the resulting organic phase was concentrated and dried, thereby obtaining 2.20 g of a compound (XII)

[Chemical Formula 91]

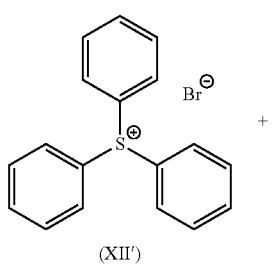

(XII')

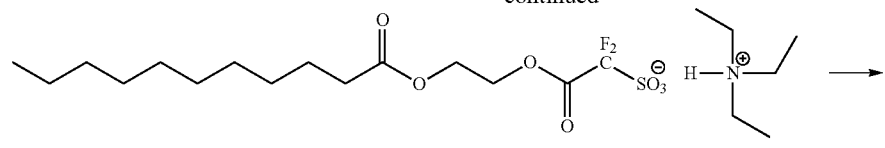

(XI)

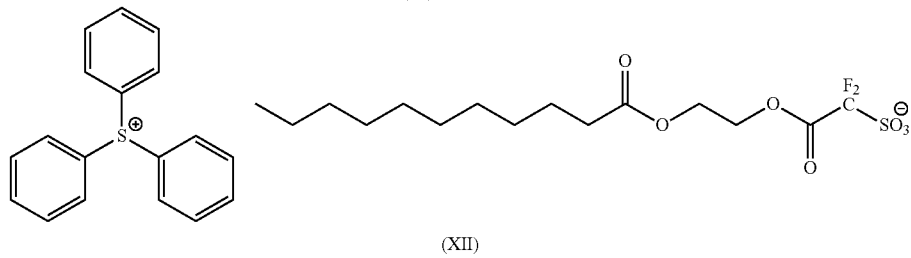

(XII)

The obtained compound (XII) was analyzed by NMR.

$^1$H-NMR(DMSO-d6, 400 MHz): δ(ppm)=7.74-7.90 (m, 15H,Phenyl), 4.39-4.42 (t, 2H,$H^c$), 4.21-4.24 (t, 2H,$H^d$), 2.25-2.89 (t, 3H,$H^e$), 1.17-1.50 (m, 15H,$H^b$), 0.79-0.88 (t, 3H,$H^a$).

$^{19}$F-NMR(DMSO-d6, 376 MHz): δ(ppm)=−106.8.

From the results above, it was confirmed that the compound (XII) had a structure shown below.

[Chemical Formula 92]

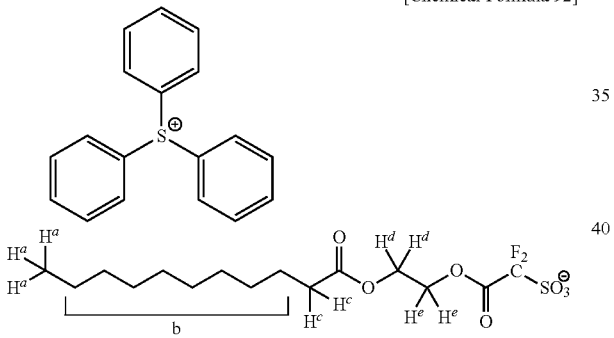

Example 9

2.50 g of triethylamine hydrochloride, 3.19 g of a compound (XIII) and 15.00 g of acetonitrile were stirred at room temperature for 15 hours. Then, the reaction liquid was subjected to filtration, and the solvent was distilled off the filtrate under reduced pressure, thereby obtaining 4.01 g of a compound (XIV) (yield: 95.6%).

[Chemical Formula 93]

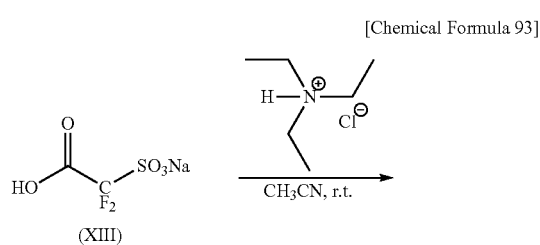

(XIII)

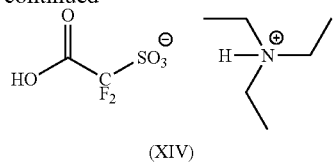

(XIV)

The obtained compound (XIV) was analyzed by NMR.

$^1$H-NMR(DMSO-d6, 400 MHz): δ(ppm)=9.20 (s, 1H,$H^c$), 3.02-3.13 (q, 6H,$H^b$), 1.11-124 (t, 9H,$H^a$).

$^{19}$F-NMR(DMSO-d6, 376 MHz): δ (ppm)=−106.7.

From the results above, it was confirmed that the compound (XIV) had a structure shown below.

[Chemical Formula 94]

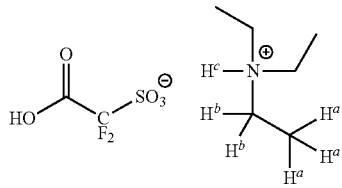

Example 10

Comparative Example 1

The components shown in Table 1 were mixed together and dissolved to obtain positive resist compositions.

TABLE 1

| | Component (A) | Component (B) | Component (D) | Component (E) | Component (S) | |
|---|---|---|---|---|---|---|
| Ex. 10 | (A)-1 [100] | (B)-1 [9.14] | (D)-1 [1.2] | (E)-1 [1.32] | (S)-1 [10] | (S)-2 [2200] |
| Comp. Ex. 1 | (A)-1 [100] | (B')-1 [8.0] | (D)-1 [1.2] | (E)-1 [1.32] | (S)-1 [10] | (S)-2 [2200] |

In Table 1, the reference characters indicate the following. Further, the values in brackets [ ] indicate the mount (in terms of parts by weight) of the component added.

In Table 1, it is noted that 9.14 parts by weight of (B)-1 is an equimolar amount of 8.0 parts by weight of (B')-1.

(A)-1: a copolymer represented by chemical formula (A)-1 shown below (wherein l/m/n=45/35/20 (molar ratio)) with Mw=7,000 and Mw/Mn=1.8

(B)-1: a compound represented by chemical formula (B)-1 shown below (the aforementioned compound (VI))

(B')-1: a compound represented by chemical formula (B')-1 shown below (D)-1: tri-n-pentylamine (E)-1: salicylic acid (S)-1: γ-butyrolactone (S)-2: a mixed solvent of PGMEA/PGME=6/4 (weight ratio)

[Chemical Formula 95]

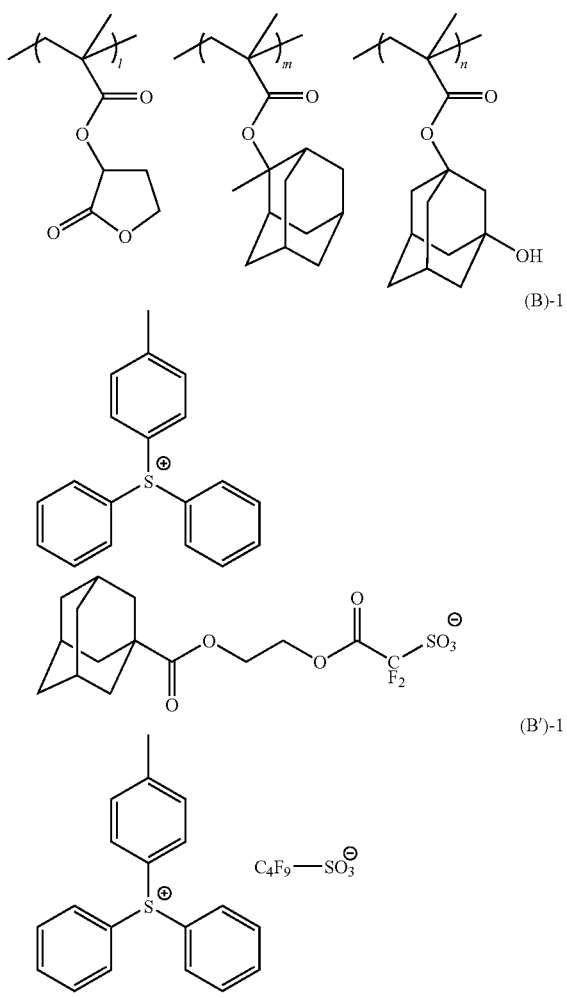

Using the obtained resist compositions, evaluations were performed as follows.

[Formation of Resist Pattern]

M organic anti-reflection film composition (product name: ARC29A, manufactured by Brewer Science Ltd.) was applied onto an 8-inch silicon wafer using a spinner, and the composition was then baked at 205° C. for 60 seconds, thereby forming an organic anti-reflection film having a film thickness of 82 nm. Then, each of the positive resist composition obtained above was applied onto the anti-reflection film using a spinner, and was then prebaked (PAD) on a hotplate at 110° C. for 60 seconds and dried, thereby forming a resist film having a film thickness of 150 nm.

Subsequently, the resist film was selectively irradiated with an ArF excimer laser (193 nm) through a mask pattern, using an ArF exposure apparatus NSR-S302 (manufactured by Nikon Corporation, NA (numerical aperture)=0.60, ⅔ annular illumination).

Thereafter, a post exposure bake (PEB) treatment was conducted at 110° C. for 60 seconds, followed by development for 30 seconds at 23° C. in a 2.38% by weight aqueous solution of tetramethylammonium hydroxide (TMAH). Then, the resist was washed for 30 seconds with pure water, followed by drying by shaking, thereby forming a resist pattern.

As a result, in each of the examples, a line and space pattern (hereafter, referred to as "L/S pattern") with a line width of 120 nm and a pitch of 240 nm was formed on the resist film.

The optimum exposure dose (Eop; $mJ/cm^2$) with which a L/S pattern having a line width of 120 nm and a pitch of 240 nm was formed was determined. Further, the resolution was determined as the critical resolution with the above Eop. The results are shown in Table 2.

Furthermore, the cross-sectional shape of the formed L/S patterns having a line width of 120 nm and a pitch of 240 nm was observed using a scanning electron microscope (product name: S-9220, manufactured by Hitachi, Ltd.). As a result, it was found that the shape of the resist pattern of Example 10 was superior to that of the resist pattern of Comparative Example 1 in that perpendicularity of the side walls of the line was high, occurrence of footing at the substrate interface was suppressed, and hence, the rectangularity was high.

[Evaluation of Line Width Roughness (LWR)]

With respect to each of the L/S patterns formed with the above Eop and having a line width of 120 nm and a pitch of 240 nm, the line width at 5 points in the lengthwise direction of the line were measured using a measuring scanning electron microscope (SEM) (product name: S-9220, manufactured by Hitachi, Ltd.; acceleration voltage: 800V), and from the results, the value of 3 times the standard deviation s (i.e., 3s) was calculated as a yardstick of LWR. The results are shown in Table 2. The smaller this 3s value is, the lower the level of roughness of the line width, indicating that a L/S pattern with a uniform width was obtained.

[Evaluation of EL Margin]

L/S patterns having a target size of 120 nm in line width and 240 nm in pitch were formed in the same manner as described above, except that the exposure dose was changed for each of the L/S patterns.

The exposure dose with which a L/S pattern having a dimension of the target dimension (line width: 120 nm)±5% (i.e., 114 nm and 126 nm) was determined, and the EL margin (unit: %) was determined by the following formula. The results are shown in Table 2.

EL margin (%)=(|E1−E2|/Eop)×100 wherein E1 represents the exposure dose ($mJ/cm^2$) for forming a L/S pattern having a line width of 114 nm, and E2 represents the exposure dose ($mJ/cm^2$) for forming a L/S pattern having a line width of 126 nm.

TABLE 2

|  | Ex. 10 | Comp. Ex. 1 |
| --- | --- | --- |
| Eop ($mJ/cm^2$) | 36.0 | 31.5 |
| Resolution (nm) | 110 | 110 |
| LWR (nm) | 8.1 | 10.4 |
| EL margin (%) | 7.37 | 5.70 |

[Evaluation of Mask Error Factor (MEF)]

With the above-mentioned Eop, L/S patterns were formed using a mask pattern targeting a L/S pattern having a line width of 130 nm and a pitch of 260 nm and a mask pattern targeting a L/S pattern having a line width of 120 nm and a pitch of 260 nm. With respect to the formed L/S patterns, the MEF was determined by the following formula.

$$MEF = |CD_{130} - CD_{120}|/|MD_{130} - MD_{120}|$$

In this formula, $CD_{130}$ and $CD_{120}$ represent the respective line widths (nm) of the actual L/S patterns respectively formed using the mask pattern targeting a line width of 130 nm and the mask pattern targeting a line width of 120 nm, and $MD_{130}$ and $MD_{120}$ represent the respective target line widths (nm), meaning $MD_{130}=130$ and $MD_{120}=120$, The closer the MEF value is to 1, the better the mask reproducibility of the resist pattern formed.

As a result, it was found that the MEF value was 2.0 in both of Example 10 and Comparative Example 1, meaning that the MEF was about the same.

[Evaluation of Mask Linearity]

With the above Eop, the L/S ratio (ratio of the line width to the space width) of the mask pattern was fixed to 1:1, and the mask size (line width) was changed by 10 nm within the range of 110 to 150 nm to form L/S patterns. The size (line width) of the formed L/S patterns was measured. The results are shown in Table 3.

As seen from Table 3, in Example 10, L/S patterns more faithful to the mask size than those in Comparative Example 1 could be formed, even when the Eop for forming a line width of 120 nm was used and the line width departed from 120 nm. Thus, it was confirmed that the resist composition of Example 10 exhibited excellent mask reproducibility when compared to the resist composition of Comparative Example 1.

TABLE 3

|        | Ex. 10 | Comp. Ex. 1 |
|--------|--------|-------------|
| 110 nm | 93.5   | 89.5        |
| 120 nm | 121.9  | 119.9       |
| 130 nm | 118.8  | 139.1       |
| 140 nm | 147.4  | 153.1       |
| 150 nm | 163.2  | 167.0       |

As seen from the results above, the resist composition of Example 10 exhibited excellent lithography properties.

Examples 11 to 13

Comparative Example 2

The components shown in Table 4 were mixed together and dissolved to obtain positive resist compositions.

TABLE 4

| | Component (A) | Component (B) | | Component (D) | Component (S) | |
|---|---|---|---|---|---|---|
| Ex. 11 | (A)-1 [100] | (B)-2 [2.53] | (B')-2 [9.2] | (D)-1 [1.0] | (S)-1 [10] | (S)-2 [2200] |
| Ex. 12 | (A)-1 [100] | (B)-2 [6.33] | (B')-2 [5.75] | (D)-1 [1.0] | (S)-1 [10] | (S)-2 [2200] |
| Ex. 13 | (A)-1 [100] | (B)-2 [13.0] | — | (D)-1 [1.0] | (S)-1 [10] | (S)-2 [2200] |

TABLE 4-continued

| | Component (A) | Component (B) | Component (D) | Component (S) | |
|---|---|---|---|---|---|
| Comp. Ex. 2 | (A)-1 [100] | — | (B')-2 [11.5] | (D)-1 [1.0] | (S)-1 [10] | (S)-2 [2200] |

In Table 4, (A)-1, (D)-1, (S)-1 and (S)-2 are respectively the same as (A)-1), (D)-1, (S)-1 and (S)-2 in Table 1, and the other reference characters indicate the following. Further, the values in brackets [ ] indicate the amount (in terms of parts by weight) of the component added.

The amounts (total amounts) of the component (B) in Examples 11 to 13 and Comparative Example 2 are in equimolar amounts.

(B)-2: a compound represented by chemical formula (B)-2 shown below (the aforementioned compound (X))

(B')-2: a compound represented by chemical formula (B')-2 shown below

[Chemical Formula 96]

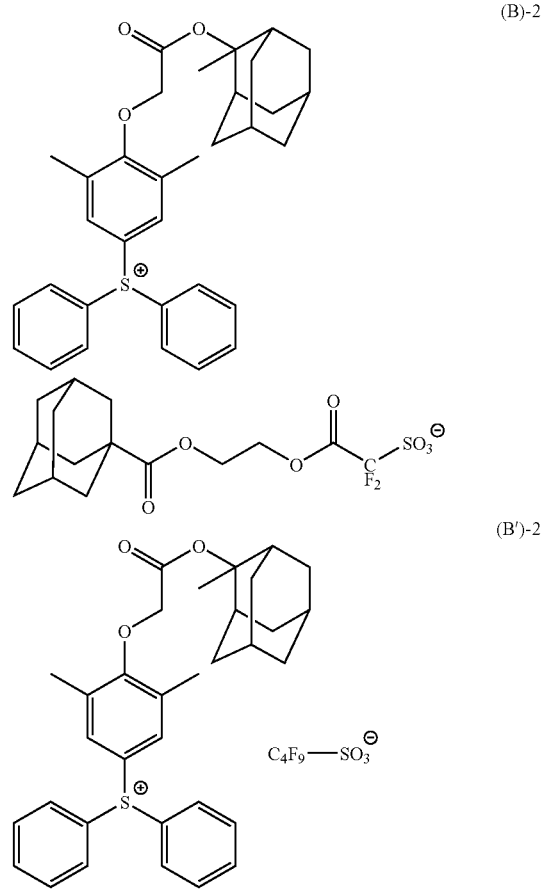

Using the obtained resist compositions, evaluations were performed as follows.

[Formation of Resist Pattern]

An organic anti-reflection film composition (product name: ARC29A, manufactured by Brewer Science Ltd.) was applied onto an 8-inch silicon wafer using a spinner, and the composition was then baked at 205° C. for 60 seconds, thereby forming an organic anti-reflection film having a film thickness of 89 nm. Then, each of the resist compositions obtained above was applied onto the anti-reflection film using a spinner, and was then prebaked (PAB) on a hotplate at 110° C. for 60 seconds and dried, thereby forming a resist film having a film thickness of 150 nm.

Subsequently, a coating solution for forming a protection film product name: TILC-035; manufactured by Tokyo Ohka Kogyo Co., Ltd.) was applied onto the resist film using a spinner, and then heated at 90° C. for 60 seconds, thereby forming a top coat with a film thickness of 90 nm.

Thereafter, using an ArF exposure apparatus for immersion lithography (product name: NSR-S609B, manufactured by Nikon Corporation, NA (numerical aperture)=1.07, σ0.97), the resist film having a top coat formed thereon was selectively irradiated with an ArF excimer laser (193 nm) through a mask having a hole pattern.

Next, a post exposure bake (PEB) treatment was conducted at 105° C. for 60 seconds, followed by development for 30 seconds at 23° C. in a 2.38% by weight aqueous solution of tetramethylammonium hydroxide (TMAH). Then, the resist film was rinsed for 30 seconds with pure water, followed by drying by shaking.

As a result, in each of the examples, a contact hole pattern (hereafter, referred to as "Dense CH pattern") in which holes having a hole diameter of 90 nm were equally spaced (pitch: 180 nm) was formed on the resist film.

Thereafter, using the optimum exposure dose (Eop; $mJ/cm^2$) with which the above Dense CH patterns were formed, a contact hole pattern (hereafter, referred to as "Iso CH pattern") in which holes having a hole diameter of 90 nm were equally spaced (pitch: 570 nm) was formed in each of the examples.

With respect to the Iso CH patterns having a hole diameter of 90 nm, various lithography properties were evaluated. The results are shown in Table 5.

[Evaluation of Depth of Focus (DOP)]

With the above-mentioned Eop, the focus was appropriately shifted up and down and resist patterns were formed in the same manner as in the evaluation of "formation of resist pattern", and the depth of focus (DOF; unit: nm) with which an Iso CH pattern was formed within the range where the variation in the target size of the Iso CH pattern was ±5% (i.e., 85.5 to 94.5 nm) was determined. The results are shown in Table 5.

[Evaluation of Mask Error Factor (MEF)]

With the above-mentioned Eop, Iso CH patterns were formed by fixing the pitch at 570 nm and changing the target size of the hole diameter to 61 nm, 63 nm, 65 nm, 67 nm and 69 nm. The value of the mask error factor was determined as the gradient of a graph obtained by plotting the target size (nm) on the horizontal axis, and the actual hole diameter (nm) of the formed CH patterns on the vertical axis. A MEF value (gradient of the plotted line) closer to 1 indicates that a resist pattern faithful to the mask pattern was formed. The results are shown in Table 5.

[EL Margin]

The exposure dose with which an Iso Dense CH pattern having a dimension of the target dimension (hole diameter: 90 nm)±5% (i.e., 85.5 and 94.5 nm) was determined, and the EL margin (unit: %) was determined by the following formula. The results are shown in Table 5.

EL margin (%)=(|E1−E2|/Eop)×100 wherein E1 represents the exposure dose ($mJ/cm^2$) for forming a CH pattern having a hole diameter of 85.5 nm, and E2 represents the exposure dose ($mJ/cm^2$) for forming a CH pattern having a hole diameter of 94.5 nm.

TABLE 5

|  | Ex. 11 | Ex. 12 | Ex. 13 | Comp. Ex. 2 |
|---|---|---|---|---|
| Eop ($mJ/cm^2$) | 37.1 | 39.4 | 42.1 | 41.7 |
| Resolution (nm) | 0.15 | 0.14 | 0.15 | 0.14 |
| LWR (nm) | 3.03 | 3.32 | 2.98 | 3.52 |
| EL margin (%) | 9.5 | 9.46 | 9.27 | 8.58 |

As seen from Table 5, the resist compositions of Examples 11 to 13 exhibited excellent MEB and EL margin as compared to the resist composition of Comparative Example 2. Further, the DOF of the resist compositions of Examples 11 to 13 was at about the same level as that of the resist composition of Comparative Example 2.

From the results shown above, it was confirmed that the compound (b0-1) according to the sixth aspect of the present invention is useful as an intermediate in the production of a compound useful as an acid generator, and the compound (b1-1) according to the third aspect of the present invention is useful as an acid generator.

Examples 14 to 20

The components shown in Table 6 were mixed together and dissolved to obtain positive resist compositions.

TABLE 6

|  | Component (A) | | Component (B) | Component (D) | Component (S) |
|---|---|---|---|---|---|
| Ex. 14 | (A)-2 | (A)-3 | (B)-1 | (D)-1 | (S)-2 |
|  | [50] | [50] | [5.0] | [0.25] | [1800] |
| Ex. 15 | (A)-2 | (A)-3 | (B)-1 | (D)-1 | (S)-2 |
|  | [50] | [50] | [7.5] | [0.25] | [1800] |
| Ex. 16 | (A)-2 | (A)-3 | (B)-1 | (D)-1 | (S)-2 |
|  | [50] | [50] | [7.5] | [0.40] | [1800] |
| Ex. 17 | (A)-2 | (A)-3 | (B)-1 | (D)-1 | (S)-2 |
|  | [50] | [50] | [7.5] | [0.55] | [1800] |
| Ex. 18 | (A)-2 | (A)-3 | (B)-1 | (D)-1 | (S)-2 |
|  | [50] | [50] | [10.0] | [0.40] | [1800] |
| Ex. 19 | (A)-2 | (A)-3 | (B)-1 | (D)-1 | (S)-2 |
|  | [50] | [50] | [10.0] | [0.55] | [1800] |
| Ex. 20 | (A)-2 | (A)-3 | (B)-1 | (D)-1 | (S)-2 |
|  | [50] | [50] | [10.0] | [1.2] | [1800] |

In Table 6, (B)-1, (D)-1 and (S)-2 are respectively the same as (B)-1, (D)-1 and (S)-2 in Table 1 and the other reference characters indicate the following. Further, the values in brackets [ ] indicate the amount (in terms of parts by weight) of the component added.

The amounts (total amounts) of the component (B) in Examples 14 to 20 are in equimolar amounts.

(A)-2: a copolymer represented by chemical formula (A)-2 shown below (wherein l/m/n=30/50/20 (molar ratio)) with Mw=10,000 and Mw/Mn=2.0

(A)-3: a copolymer represented by chemical formula (A)-3 shown below (wherein l/m/n=40/40/20 (molar ratio)) with Mw=10,000 and Mw/Mn=2.0

[Chemical Formula 97]

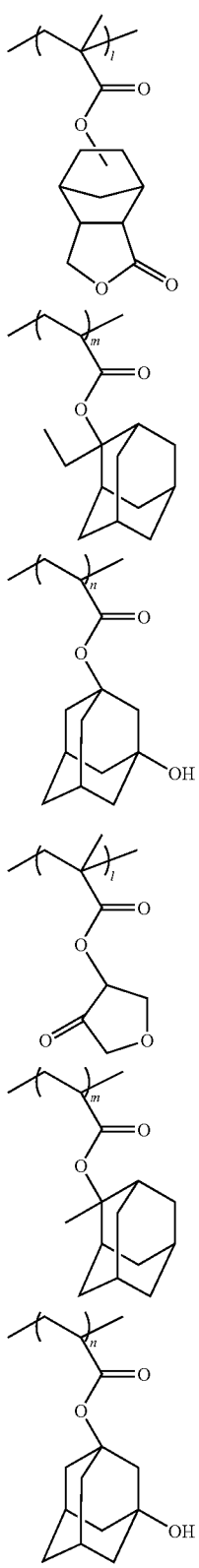

Using the obtained resist compositions, evaluations were performed as follows.

[Formation of Resist Pattern]

An organic anti-reflection film composition (product name: ARC29A, manufactured by Brewer Science Ltd.) was applied onto an 12-inch silicon wafer using a spinner, and the composition was then baked at 205° C. for 60 seconds, thereby forming an organic anti-reflection film having a film thickness of 70 nm. Then, each of the positive resist composition obtained above was applied onto the anti-reflection film using a spinner, and was then prebaked (PAB) on a hotplate at 110° C. for 60 seconds and dried, thereby forming a resist film having a film thickness of 170 nm.

Subsequently, the resist film was selectively irradiated with an ArF excimer laser (193 nm) through a mask patterned using an ArF exposure apparatus NSR-S308F (manufactured by Nikon Corporation, NA (numerical aperture)=0.85, σ=0.95).

Thereafter, a post exposure bake (PEB) treatment was conducted at 90° C. for 60 seconds, followed by development for 30 seconds at 23° C. in a 2.38% by weight aqueous solution of tetramethylammonium hydroxide (TMAH). Then, the resist was washed for 30 seconds with pure water, followed by drying by shaking, thereby forming a resist pattern.

As a result, in each of the examples, a Dense CH pattern in which holes having a hole diameter of 110 nm were equally spaced (pitch: 210 nm) was formed on the resist film.

Thereafter, using the optimum exposure dose (Eop; $mJ/cm^2$) with which the above Dense CH patterns were formed, an Iso CH pattern in which holes having a hole diameter of 110 nm were equally spaced (pitch: 780 nm) was formed in each of the examples.

With respect to the Dense CH patterns and Iso CH patters having a hole diameter of 110 nm, various lithography properties were evaluated. The results are shown in Table 7.

[Evaluation of Depth of Focus (DOF)]

With the above-mentioned Eop, the focus was appropriately shifted up and down and resist patterns were formed in the same manner as in the evaluation of "formation of resist pattern", and the depth of focus (DOF; unit: nm) with which a CH pattern was formed within the range where the variation in the target size of the CH pattern was ±5% (i.e., 104.5 to 115.5 nm) was determined.

[Evaluation of Mask Error Factor (MEF)]

By using a mask pattern in which the target size was changed by 1 nm in the range of 110 nm±5 nm, CH patterns were formed with the above Eop (wherein the pitch was 210 nm for Dense CH patterns and 780 nm for Iso CH patterns). The value of the mask error factor was determined as the gradient of a graph obtained by plotting the target size (nm) on the horizontal axis, and the actual hole diameter (nm) of the formed CH patterns on the vertical axis. A MEF value (gradient of the plotted line) closer to 1 indicates that a resist pattern faithful to the mask pattern was formed.

[Evaluation of CD Uniformity (CDU)]

With respect to each of the CH patterns formed, the hole diameter (CD) of 54 holes were measured for a Dense CH pattern, and the hole diameter of 26 holes were measured for an Iso CH pattern. From the results, the value of 3 times the standard deviation a (i.e., 3σ) was calculated as a yardstick of CD uniformity (CDU). The smaller this 3σ value is, the higher the level of CDU of the holes formed in the resist film, meaning that the variation in the hole diameter of holes present in a predetermined range is small.

[Evaluation of Circularity]

With respect to each of the CH patterns, the shape of the holes was observed using a measuring SEM (product name: S-9220, manufactured by Hitachi, Ltd.), and evaluated with the following criteria.

A: extremely high circularity (no unevenness was observed at the circumferential portions of the hole pattern when the hole pattern was observed from the upper side thereof, and the shape of the pattern was excellent)

B: high circularity (although slight unevenness was observed at the circumferential portions of the hole pattern when the hole pattern was observed from the upper side thereof, the pattern as a whole had a high level of circularity)

TABLE 7

|  |  | Ex. 14 | Ex. 15 | Ex. 16 | Ex. 17 | Ex. 18 | Ex. 19 | Ex. 20 |
|---|---|---|---|---|---|---|---|---|
| Eop (mJ/cm$^2$) | | 53 | 31.5 | 36.3 | 42.2 | 26.4 | 29.8 | 46.5 |
| DOF (nm) | Dense | 0.21 | 0.14 | 0.16 | 0.13 | 0.13 | 0.12 | 0.11 |
|  | Iso | 0.13 | 0.12 | 0.12 | 0.12 | 0.14 | 0.11 | 0.12 |
| MEF | Dense | 2.46 | 2.65 | 2.68 | 2.5 | 2.8 | 2.82 | 2.98 |
|  | Iso | 1.79 | 2.16 | 1.91 | 1.96 | 2.31 | 2.65 | 3.06 |
| CDU | Dense | 6.23 | 4.73 | 4.32 | 4.61 | 5.33 | 4.06 | 5.35 |
|  | Iso | 8.03 | 4.84 | 5.78 | 4.96 | 5.11 | 4.87 | 5.9 |
| Circularity | Dense | B | A | A | A | A | A | B |
|  | Iso | B | A | A | A | A | A | A |

As seen from Table 7, the resist compositions of Examples 14 to 20 exhibited excellent lithography properties (DOF, MEF, CDU, circularity) for both of a Dense CH pattern and an Iso CH pattern. Especially, it was found that the resist compositions of Examples 15 to 19 exhibited excellent properties with respect to the shape of the holes (CDU and circularity).

From the results shown above, it was confirmed that the compound (b0-1) according to the sixth aspect of the present invention is useful as an intermediate in the production of a compound useful as an acid generator, and the compound (b1-1) according to the third aspect of the present invention is useful as an acid generator.

Example 21

To 8.00 of a compound (III) and 150.00 g of dichloromethane were dropwise added 7.02 g of 1-adamantaneacetyl chloride and 3.18 g of triethylamine while cooling with ice. Then, the resultant was stirred at room temperature for 20 hours, followed by filtration. Thereafter, the filtrate was washed with 54.6 g of pure water three times, and the organic phase was concentrated and dried, thereby obtaining 14.90 g of a compound (XV) (yield: 88.0%).

[Chemical Formula 98]

The obtained compound (XV) was analyzed by NMR.

$^1$H-NMR(DMSO, 400 MHz): δ (ppm)=8.81 (br s, 1H,H$^c$), 4.40 (t, 2H,H$^d$), 4.20 (t, 2H,H$^e$), 3.08 (q, 6H,H$^b$), 2.05 (s, 2H,H$^f$), 1.53-1.95 (m, 15H,Adamantane), 1.17 (t, 9H,H$^a$)

$^{19}$F-NMR(DMSO, 376 MHz): δ (ppm)=−106.9.

From the results above, it was confirmed that the compound (XV) had a structure shown below.

[Chemical Formula 99]

Example 22

7.04 g of a compound (V) was dissolved in 70.4 g of dichloromethane and 70.4 g of water, and 9.27 g of the compound (XV) was added thereto. The resultant was stirred for 1 hour, followed by liquid separation to collect the organic phase. The organic phase was washed once with 70.4 g of 1% aqueous solution of HCl, and four times with 70.4 g of pure water. Thereafter, the resulting organic phase was concentrated and dried, thereby obtaining 11.59 g of a compound (XVI) (yield: 90.6%).

[Chemical Formula 100]

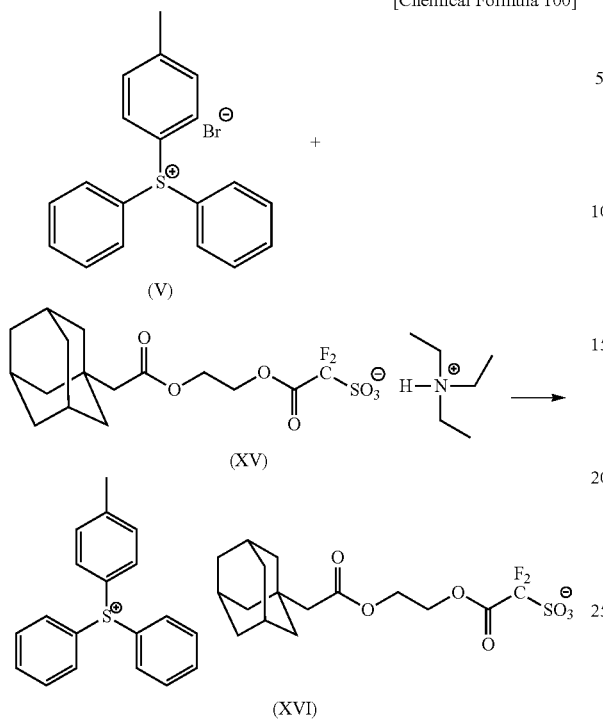

The obtained compound (XVI) was analyzed by NMR.
$^{1}$H-NMR(DMSO, 400 MHz): δ (ppm)=7.50-7.87 (m, 14H, Phenyl), 4.42 (s, 2H,H$^c$), 4.23 (s, 2H,H$^b$), 2.43 (s, 3H,H$^a$), 2.01 (s, 2H,H$^f$), 1.94 (s, 2H,Adamantane), 1.52-1.61 (m, 13H, Adamantane)
$^{19}$F-NMR(DMSO, 376 MHz): δ (ppn)=−106.49

From the results above, it was confirmed that the compound (XVI) had a structure shown below.

[Chemical Formula 101]

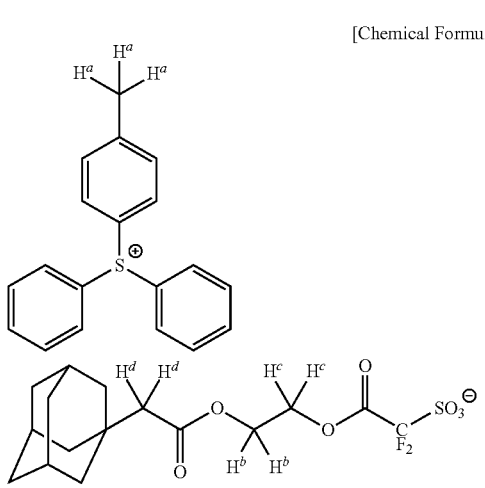

Example 23

21.6 g of a compound (XX), 53.0 g of water and 69.7 g of dichloromethane were stirred at room temperature, and 12.9 g of a compound (IV) was added thereto. The resultant was stirred for 1 hour, followed by liquid separation to collect the organic phase. The organic phase was washed once with 34.9 g of 1% aqueous solution of HCl, and twice with 69.7 g of pure water. Thereafter, the resulting organic phase was concentrated and dried, thereby obtaining 9.94 g of a compound (XXI) (yield: 61.4%).

[Chemical Formula 102]

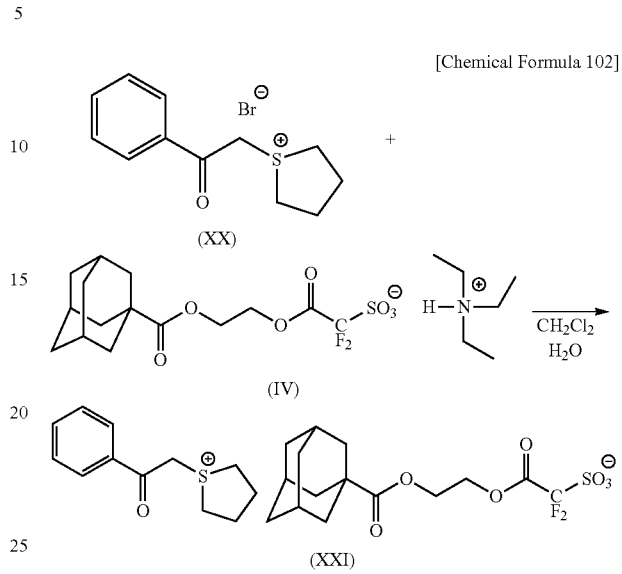

The obtained compound (XXI) was analyzed by NMR.
$^{1}$H-NMR(DMSO, 400 MHz): δ (ppm)=8.00 (d, 2H,H$^f$), 7.75 (t, 1H,H$^i$), 7.58 (t, 2H,H$^g$), 5.30 (s, 2H,H$^e$), 4.37-4.44 (t, 2H, H$^a$), 4.17-4.26 (t, 2H,H$^b$), 3.54 (m, 4H,H$^d$), 2.49-2.18 (m, 4H,H$^c$), 1.93-1.60 (m, 15H, -Adamantane)
$^{19}$F-NMR(DMSO, 376 MHz): δ (ppm)=−106.2

From the results above, it was confirmed that the compound (XXI) had a structure shown below.

[Chemical Formula 103]

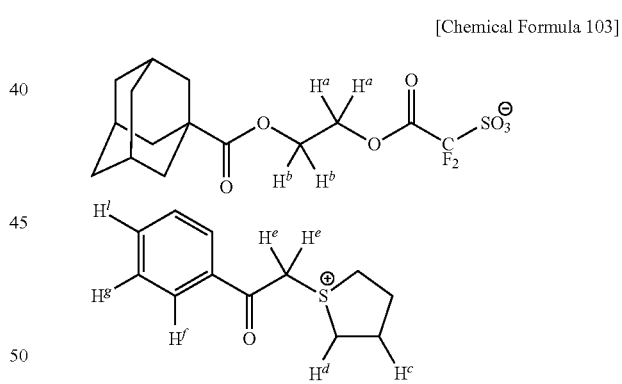

Examples 24 to 26

The components shown in Table 8 were mixed together and dissolved to obtain positive resist compositions.

TABLE 8

| | Composition [parts by weight] | | | | |
|---|---|---|---|---|---|
| | Component (A) | Component (B) | Component (D) | Component (S) | PEB (° C./sec) |
| Ex. 24 | (A)-4 [100] | (B)-3 [11.2] | — | (D)-2 [0.5] | (S)-1 [2200] | 80/60 |

TABLE 8-continued

| | Composition [parts by weight] | | | | |
|---|---|---|---|---|---|
| | Component (A) | Component (B) | Component (D) | Component (S) | PEB (°C./sec) |
| Ex. 25 | (A)-5 [100] | (B)-3 [11.2] | — | (D)-2 [0.5] | (S)-1 [2200] | 90/60 |
| Ex. 26 | (A)-6 [100] | (B)-1 [6.0] | (B)-4 [5.83] | (D)-2 [0.3] | (S)-1 [2200] | 90/60 |

In Table 8, (B)-1 and (S)-2 are respectively the same as (B)-1 and (S)-2 in Table 1, and the other reference characters indicate the following. Further, the values in brackets [ ] indicate the amount (in terms of parts by weight) of the component added.

The amounts (total amounts) of the component (B) in Examples 24 to 26 are in equimolar amounts.

(A)-4: a copolymer represented by chemical formula (A)-4 shown below (wherein l/m/n=30/50/20 (molar ratio)) with Mw=10,000 and Mw/Mn=2.0

(A)-5: a copolyrmer represented by chemical formula (A)-5 shown below (wherein l/m/n=30/50/20 (molar ratio)) with Mw=10,000 and Mw/Mn=2.0

(A)-6: a polymeric compound (A)-6 (synthesized in Reference Example 3 described below)

(B)-3: a compound represented by chemical formula (B)-3 shown below (the aforementioned compound (XVI))

(B)-4: a compound represented by chemical formula (B)-4 shown below (the aforementioned compound (XXI))

(D)-2: stearyldiethanolamine

[Chemical Formula 104]

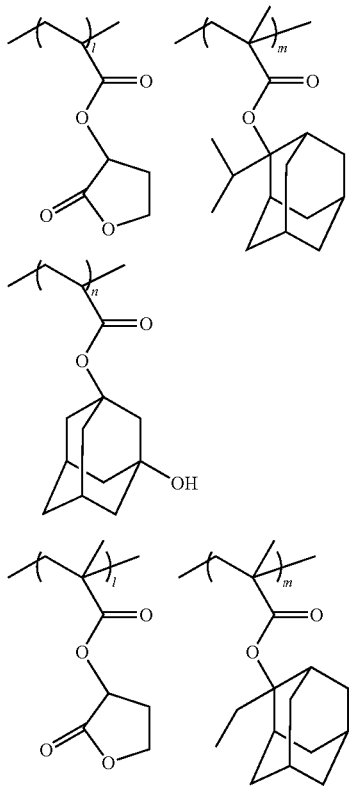

(A)-4

(A)-5

[Chemical Formula 105]

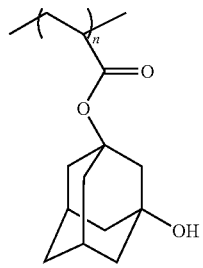

(B)-3

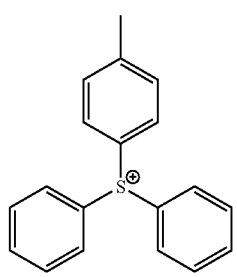

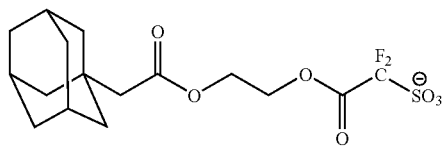

(B)-4

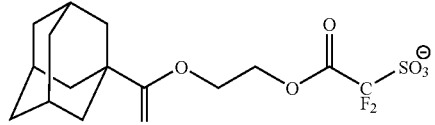

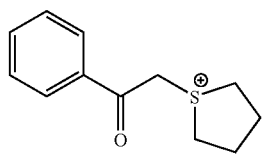

Synthesis Example of Polymeric Compound (A)-6

Reference Example 1

4.8 g of sodium hydride (NaH) was charged into a 1 L three-necked flask. While maintaining the temperature of the three-necked flask at 0° C. in an ice bath, 300 g of tetrahydrofuran (THF) was added, 124 g of a compound (1) was further added while stirring, and stirring was continued for 10 minutes. Then, 30 g of a compound (2) was added while stirring, and a reaction was effected for 12 hours. After the completion of the reaction, the reaction liquid was subjected to suction filtration, and THF was removed from the obtained filtrate by concentration under reduced pressure. Then, water and ethyl acetate was added to the concentrated liquid, and extraction was conducted. The resulting ethyl acetate solution was concentrated under reduced pressure, and purified by column chromatography (SiO$_2$, heptane:ethyl acetate=8:2). The obtained fraction was concentrated and dried under reduced pressure, thereby obtaining 12 g of a compound (3).

[Chemical Formula 106]

1) NaH
2) Br-CH2-C(=O)-O-[methyladamantyl] (2)

HO-CH2-CH2-OH (1)

→

HO-CH2-CH2-O-CH2-C(=O)-O-[methyladamantyl] (3)

The obtained compound (3) was analyzed by $^1$H-NMR. The results are shown below.

$^1$H-NMR (solvent: CDCl$_3$, 400 MHz): δ (ppm)=4.09 (s, 2H(H$^a$)), 3.75 (t, 2H(H$^b$)), 3.68 (t, 2H(H$^c$)), 3.03 (brs, 2H(H$^d$)), 1.51-2.35 (m, 17H(H$^e$)).

From the results shown above, it was confirmed that the compound (3) had a structure shown below.

[Chemical Formula 107]

H$^d$O-CH$_2$(H$^b$)-CH$_2$(H$^a$)-O-CH$_2$-C(=O)-O-[methyl(H$^e$)adamantyl]
     H$^c$

Reference Example 2

5 g of the compound (3), 3.04 g of triethylamine (Et$_3$N) and 10 g of THF were charged into a 300 mL three-necked flask, and stirred for 10 minutes. Then, 2.09 g of a compound (4) and 10 g of THF were added to the three-necked flask, and a reaction was effected at room temperature for 12 hours. After the completion of the reaction, the reaction liquid was subjected to suction filtration, and THF was removed from the obtained filtrate by concentration under reduced pressure. Then, water and ethyl acetate was added to the concentrated liquid, and extraction was conducted. The resulting ethyl acetate solution was concentrated under reduced pressure, and purified by column chromatography (SiO$_2$, heptane:ethyl acetate=8:2). The obtained fraction was concentrated and dried under reduced pressure, thereby obtaining 4.9 g of a compound (5).

[Chemical Formula 108]

1) Et$_3$N
2) CH$_2$=C(CH$_3$)-C(=O)-Cl (4)

HO-CH$_2$-CH$_2$-O-CH$_2$-C(=O)-O-[methyladamantyl] (3)

→

-continued

CH$_2$=C(CH$_3$)-C(=O)-O-CH$_2$-CH$_2$-O-CH$_2$-C(=O)-O-[methyladamantyl] (5)

The obtained compound (5) was analyzed by $^1$H-NMR. The results are shown below.

$^1$H-NMR (solvent: CDCl$_3$, 400 MHz): δ(ppm)=6.15 (s, 1H(H$^a$)), 5.58 (s, 1H(H$^b$)), 4.35 (t, 2H(H$^c$)), 4.08 (s, 2H(H$^d$)), 3.80 (t, 2H(H$^e$)), 1.51-2.35 (m, 20H(H$^f$)).

From the results shown above, it was confirmed that the compound (5) had a structure shown below.

[Chemical Formula 109]

H$^a$H$^b$C=C(H$^f$)-C(=O)-O-CH$_2$(H$^e$)-CH$_2$(H$^d$)-O-CH$_2$(H$^c$)-C(=O)-O-[methyl(H$^f$)adamantyl]

Reference Example 3

Synthesis of Polymeric Compound (A)-6

6.30 g (30.30 mmol) of a compound (6) shown below, 7.00 g (20.83 mmol) of the compound (5) and 2.83 g (11.99 mmol) of a compound (7) shown below were dissolved in 64.52 g of methyl ethyl ketone to obtain a solution. Then, 11.68 mmol of a polymerization initiator (product name: V-601, manufactured by Wako Pure Chemical Industries, Ltd.) was added and dissolved in the obtained solution. The resultant was dropwise added to 26.88 g of methyl ethyl ketone heated to 75° C. in a nitrogen atmosphere over 6 hours. The resulting reaction liquid was heated while stirring for 1 hour, and then cooled to room temperature.

Subsequently, the resulting polymerization liquid was concentrated to a solid content of 30% by weight, and dropwise added to 320 ml of n-heptane at room temperature to deposit a copolymer. Then, 54 g of a THF solution of the obtained copolymer was prepared, and the THF solution was dropwise added to 320 ml of n-heptane to deposit a copolymer.

The obtained copolymer was dispersed in a methanol/water=60/40 (weight ratio) mixed solution to wash the copolymer, and then the copolymer was dispersed in a methanol/water=70/30 (weight ratio) mixed solution to wash the copolymer, followed by filtration to collect the copolymer.

The thus obtained copolymer was dried at 40° C. for 3 days, thereby obtaining 12.0 g of a white powder (yield: 74%).

The obtained copolymer was designated as "polymeric compound (A)-6". The structure of the polymeric compound (A)-6 is shown below.

The polymeric compound (A)-6 was analyzed by $^{13}$C-NMR (600 MHz). As a result, it was found that the composition of the polymer (ratio (molar ratio) of the respective structural units within the structural formula) was l/m/n=52.6/27.5/19.9. Further, with respect to the polymeric compound (A)-6, the weight average molecular weight and the dispersity were determined by the polystyrene equivalent value as measured by gel permeation chromatography (GPC). As a result, it was found that the weight average molecular weight was 5,300, and the dispersity was 1.97. From the results above, it was found that the polymeric compound (A)-6 was a copolymer of the compound (6), the compound (5) and the compound (7).

[Chemical Formula 110]

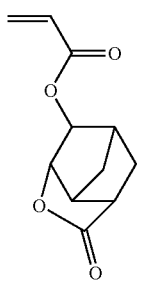

(6)

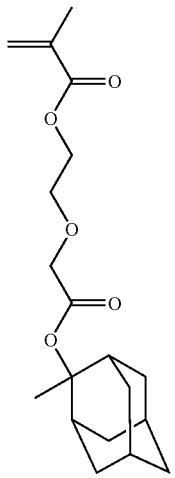

(5)

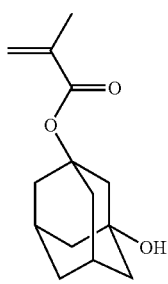

(7)

[Chemical Formula 111]

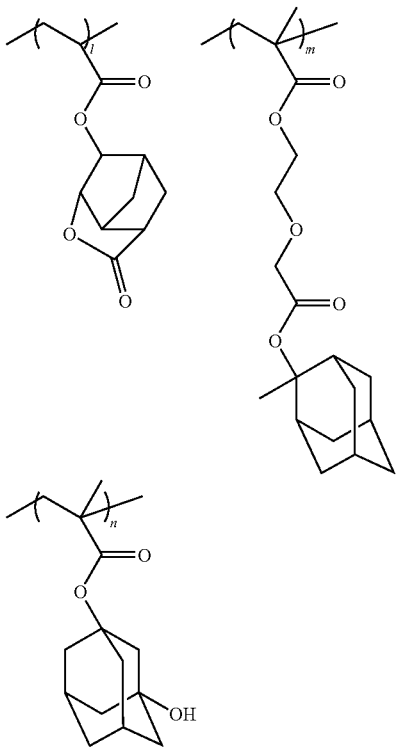

(A)-6

Using the obtained resist compositions, evaluations were performed as follows.

[Formation of Resist Pattern]

An organic anti-reflection film composition product name: ARC29A, manufactured by Brewer Science Ltd.) was applied onto an 12-inch silicon wafer using a spinner, and the composition was then baked at 205° C. for 60 seconds, thereby forming an organic anti-reflection film having a film thickness of 89 nm. Then, each of the positive resist compositions obtained in Examples 24 to 26 was applied onto the anti-reflection film using a spinner, and was then prebaked (PAB) on a hotplate at 90° C. for 60 seconds and dried, thereby forming a resist film having a film thickness of 120 nm.

Subsequently, a coating solution for forming a protection film (product name: TSRC-002; manufactured by Tokyo Ohka Kogyo Co., Ltd.) was applied onto the resist film using a spinner, and then heated at 90° C. for 60 seconds, thereby forming a top coat with a film thickness of 28 nm.

Thereafter, using an ArF exposure apparatus for immersion lithography (product name: NSR-S609B, manufactured by Nikon Corporation, NA (numerical aperture)=1.07, 2/3 annular illumination, reduction ratio: 1/4, immersion medium: water), the resist film having a top coat formed thereon was selectively irradiated with an ArF excimer laser (193 nm) through a mask pattern (6% halftone).

Next, the top coat was removed using a protection-film removing solution (product name: TS-Rememover-S; manufactured by Tokyo Ohka Kogyo Co., Ltd.). Then, a post exposure bake (PEB) treatment was conducted under the conditions indicated in Table 8, followed by alkali development for 30 seconds at 23° C. in a 2.38% by weight aqueous solution of tetramethylammonium hydroxide (product name: NMD-W, manufactured by Tokyo Ohka Kogyo Co., Ltd.). Then, the resist film was rinsed for 25 seconds with pure water, followed by drying by shaking.

As a result, in each of the examples, a CH pattern having a hole diameter of 70 nm and a pitch of 131 nm was formed. The optimum exposure dose (Eop; mJ/cm$^2$) with which the CH pattern was formed, i.e., sensitivity, is indicated in Table 9.

[Evaluation of Circularity]

With respect to each of the CH patterns, the shape of the holes was observed using a measuring SEM (product name: S-9220, manufactured by Hitachi, Ltd.), and evaluated with the same criteria as those used in Examples 14 to 20. The results are shown in Table 9.

TABLE 9

|  | Ex. 24 | Ex. 25 | Ex. 26 |
|---|---|---|---|
| Eop (mJ/cm$^2$) | 31 | 28 | 20 |
| Circularity | A | B | B |

From the results shown in Table 9, it was confirmed that the compound (b0-1) according to the sixth aspect of the present invention is useful as an intermediate in the production of a compound useful as an acid generator, and the compound (b1-1) according to the third aspect of the present invention is useful as an acid generator.

The invention claimed is:

1. A resist composition comprising a base component (A) which exhibits changed solubility in an alkali developing solution under action of acid and an acid-generator component (B) which generates acid upon exposure, said acid-generator component (B) comprising an acid generator (B1) consisting of a monomeric compound represented by general formula (b1-1-1) shown below:

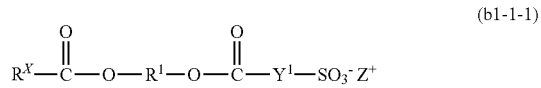

(b1-1-1)

wherein R$^x$ represents a saturated hydrocarbon group with or without a substituent exclusive of a nitrogen atom; Y$^1$ represents an alkylene group or fluorinated alkyl group of 1 to 4 carbon atoms; R$^1$ represents an alkylene group; and Z$^+$ represents an organic cation exclusive of an ion represented by general formula (w-1) shown below:

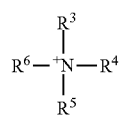

(w-1)

wherein each of R$^3$ to R$^6$ independently represents a hydrogen atom or a hydrocarbon group with or without a substituent, with the proviso that at least one of R$^3$ to R$^6$ represents a hydrocarbon group; and at least two of R$^3$ to R$^6$ may be mutually bonded to form a ring.

2. The resist composition according to claim 1, wherein said base component (A) is a base component which exhibits increased solubility in an alkali developing solution under action of acid.

3. The resist composition according to claim 2, wherein said base component (A) comprises a resin component (A1) which exhibits increased solubility in an alkali developing solution under action of acid, and said resin component (A1) comprises a structural unit (a1) derived from an acrylate ester containing an acid dissociable, dissolution inhibiting group.

4. The resist composition according to claim 3, wherein said resin component (A1) further comprises a structural unit (a2) derived from an acrylate ester containing a lactone-containing cyclic group.

5. The resist composition according to claim 3, wherein said resin component (A1) further comprises a structural unit (a3) derived from an acrylate ester containing a polar group-containing aliphatic hydrocarbon group.

6. The resist composition according to claim 1, which further comprises a nitrogen-containing organic compound (D).

7. A method of forming a resist pattern, comprising: applying a resist composition of any one of claims 1 and 2 to 6 to a substrate to form a resist film on the substrate;

conducting exposure of said resist film; and alkali-developing said resist film to form a resist pattern.

8. A monomeric compound represented by general formula (b1-1-1) shown below:

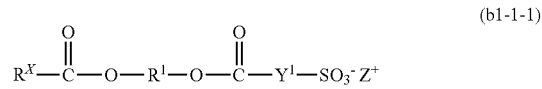

(b1-1-1)

wherein R$^x$ represents a group in which one or more hydrogen atoms have been removed from a monocycloalkane with or without an alkyl group, an alkoxy group, a halogen atom, a halogenated alkyl group, a hydroxyl group, or a group containing at least one atom selected from the group consisting of a halogen atom, an oxygen atom and a sulfur atom as a substituent, or a group in which one or more hydrogen atoms have been removed from a polycycloalkane with or without an alkyl group, an alkoxy group, a halogen atom, a halogenated alkyl group, a hydroxyl group, or a group containing at least one atom selected from the group consisting of a halogen atom, an oxygen atom and a sulfur atom as a substituent; Y$^1$ represents an alkylene group or fluorinated alkyl group of 1 to 4 carbon atoms; R$^1$ represents an alkylene group; and Z$^+$ represents an organic cation exclusive of an ion represented by general formula (w-1) shown below:

(w-1)

wherein each of R$^3$ to R$^6$ independently represents a hydrogen atom or a hydrocarbon group with or without a substituent, with the proviso that at least one of R$^3$ to R$^6$ represents a hydrocarbon group; and at least two of R$^3$ to R$^6$ may be mutually bonded to form a ring.

9. A method of producing the monomeric compound (b1-1-1) of claim 8, comprising reacting a compound (b0-01) represented by general formula (b0-01) shown below with a compound (b0-02) represented by general formula (b0-02) shown below:

(b0-01)

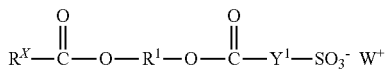

(b0-02)

wherein $R^x$ $R^1$ and $Y^1$ are as defined in claim 8; $W^+$ represents an alkali metal ion or an ion represented by general formula (w-1) shown below; $Z^+$ represents an organic cation exclusive of an ion represented by general formula (w-1) shown below; and $A^-$ represents a non-nucleophilic ion:

(w-1)

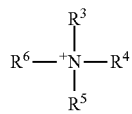

wherein each of $R^3$ to $R^6$ independently represents a hydrogen atom or a hydrocarbon group with or without a substituent, with the proviso that at least one of $R^3$ to $R^6$ represents a hydrocarbon group; and at least two of $R^3$ to $R^6$ may be mutually bonded to form a ring.

10. An acid generator consisting of the compound of claim 8.

11. A monomeric compound represented by general formula (b0-1-11) shown below:

(b0-1-11)

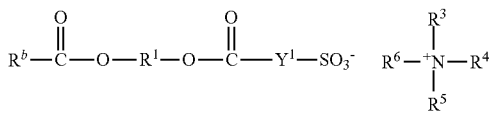

wherein $R^1$ represents an alkylene group; $R^b$ represents a group in which one or more hydrogen atoms have been removed from a monocycloalkane with or without an alkyl group, an alkoxy group, a halogen atom, a halogenated alkyl group, a hydroxyl group, or a group containing at least one atom selected from the group consisting of a halogen atom, an oxygen atom and a sulfur atom as a substituent, or a group in which one or more hydrogen atoms have been removed from a polycycloalkane with or without an alkyl group, an alkoxy group, a halogen atom, a halogenated alkyl group, a hydroxyl group, or a group containing at least one atom selected from the group consisting of a halogen atom, an oxygen atom and a sulfur atom as a substituent, provided that the substituent does not include a nitrogen atom; $Y^1$ represents an alkylene group or fluorinated alkyl group of 1 to 4 carbon atoms; each of $R^3$ to $R^6$ independently represents a hydrogen atom or a hydrocarbon group with or without a substituent, with the proviso that at least one of $R^3$ to $R^6$ represents a hydrocarbon group; and at least two of $R^3$ to $R^6$ may be mutually bonded to form a ring.

* * * * *